US011607458B2

(12) United States Patent
Wang et al.

(10) Patent No.: US 11,607,458 B2
(45) Date of Patent: Mar. 21, 2023

(54) ENRICHMENT-TRIGGERED CHEMICAL DELIVERY SYSTEM

(71) Applicant: Georgia State University Research Foundation, Inc, Atlanta, GA (US)

(72) Inventors: Binghe Wang, Atlanta, GA (US); Yueqin Zheng, Atlanta, GA (US); Xingyue Ji, Atlanta, GA (US); Robert Emuobonuvie Aghoghovbia, Atlanta, GA (US)

(73) Assignee: GEORGIA STATE UNIVERSITY RESEARCH FOUNDATION, INC., Atlanta, GA (US)

( * ) Notice: Subject to any disclaimer, the term of this patent is extended or adjusted under 35 U.S.C. 154(b) by 0 days.

(21) Appl. No.: 16/758,833

(22) PCT Filed: Oct. 25, 2018

(86) PCT No.: PCT/US2018/057591
§ 371 (c)(1),
(2) Date: Apr. 23, 2020

(87) PCT Pub. No.: WO2019/084323
PCT Pub. Date: May 2, 2019

(65) Prior Publication Data
US 2021/0000965 A1 Jan. 7, 2021

Related U.S. Application Data

(60) Provisional application No. 62/577,058, filed on Oct. 25, 2017.

(51) Int. Cl.
*A61K 47/55* (2017.01)
*A61K 47/54* (2017.01)
*A61K 31/675* (2006.01)
*A61K 31/704* (2006.01)

(52) U.S. Cl.
CPC ............ *A61K 47/55* (2017.08); *A61K 31/675* (2013.01); *A61K 31/704* (2013.01); *A61K 47/548* (2017.08); *A61K 47/549* (2017.08)

(58) Field of Classification Search
CPC .................................................... A61K 47/55
See application file for complete search history.

(56) References Cited

U.S. PATENT DOCUMENTS

| 6,316,652 | B1 | 11/2001 | Steliou |
| 6,331,532 | B1 | 12/2001 | Murphy et al. |
| 7,799,782 | B2* | 9/2010 | Munson .................. A61P 19/10 514/234.5 |
| 8,552,183 | B2 | 10/2013 | Wiessler et al. |
| 10,300,069 | B2 | 5/2019 | Wang et al. |
| 10,751,344 | B2 | 8/2020 | Wang et al. |
| 10,806,807 | B2* | 10/2020 | Mejia Oneto .......... C07H 15/24 |
| 2017/0128456 | A1* | 5/2017 | Wang ........................ A61P 1/04 |
| 2020/0115360 | A1 | 4/2020 | Wang et al. |
| 2020/0283382 | A1 | 9/2020 | De La Cruz et al. |
| 2021/0221835 | A1 | 7/2021 | Wang et al. |

FOREIGN PATENT DOCUMENTS

| WO | 2004069159 A2 | 8/2004 |
| WO | 2010051530 A2 | 5/2010 |
| WO | 2012156919 A1 | 11/2012 |
| WO | 2014065860 A1 | 5/2014 |
| WO | 2014138186 | 9/2014 |
| WO | 2015191616 A1 | 12/2015 |
| WO | 2017046602 A1 | 3/2017 |

OTHER PUBLICATIONS

Kern et al., "Discovery of Pyrophosphate Diesters as Tunable, Soluble, and Bioorthogonal Linkers for Site-Specific Antibody-Drug Conjugates," J. Am. Chem. Soc., vol. 138, Issue No. 4, 2016, pp. 1430-1445.
McKay et al., "Click Chemistry in Complex Mixtures: Bioorthogonal Bioconjugation," Chemistry and Biology, vol. 21, Issue No. 9, 2014, pp. 1075-1101.
PCT/US2018/057591 , "International Preliminary Report on Patentability," dated May 7, 2020, 7 pages.
PCT/US2018/057591 , "International Search Report and Written Opinion," dated Jan. 4, 2019, 9 pages.
Rossin et al., "Triggered Drug Release from an Antibody-Drug Conjugate Using Fast 'Click-to-Release' Chemistry in Mice," Bioconjugate Chem., vol. 27, Issue No. 7, 2016, pp. 1697-1706.
Agarwal et al. "Site-Specific Antibody—Drug Conjugates: The Nexus of Bioorthogonal Chemistry, Protein Engineering, and Drug Development." *Bioconjug Chem* 2015, 26(2): 176-192.
Ahmed et al. "Carbohydrate-based materials for targeted delivery of drugs and genes to the liver." *Nanomedicine* (London, England) 2015, 10(14): 2263-2288.
Akhtar, et al. "Prostate Specific Membrane Antigen-Based Therapeutics" *Hindawi Publishing Corporation, Advances in Urology* vol. 2012, Article ID 973820, 9 pages doi:10.1155/2012/973820.

(Continued)

*Primary Examiner* — Rei Tsang Shiao
(74) *Attorney, Agent, or Firm* — Kilpatrick Townsend & Stockton LLP

(57) ABSTRACT

Disclosed herein is a chemical delivery system having: i) a cargo compound comprising a first reactive moiety covalently bonded to a first enrichment moiety and a tethered cargo moiety, wherein the first reactive moiety is bonded to the tethered cargo moiety via a cleavable linker; and ii) a trigger compound comprising a second reactive moiety covalently bonded to a second enrichment moiety and a cargo-releasing moiety. The first enrichment moiety and the second enrichment moiety cause an increase in concentration of the cargo compound and the concentration of the trigger compound at a target site, causing a bimolecular reaction between the first reactive moiety and the second reactive moiety to form a cyclization precursor compound. The cargo moiety is then released from the cyclization precursor compound in a unimolecular cyclization reaction. Methods for treating conditions such as cancer, inflammatory conditions, and infections with the chemical delivery systems are also described.

11 Claims, 3 Drawing Sheets
Specification includes a Sequence Listing.

(56) References Cited

OTHER PUBLICATIONS

Blackman et al. "Tetrazine Ligation: Fast Bioconjugation Based on Inverse-Electron-Demand Diels-Alder Reactivity." *J Am Chem Soc* 2008, 130(41): 13518-13519.
Calvaresi and Hergenrother, "Glucose conjugation for the specific targeting and treatment of cancer" *Chem Sci* Jun. 2013; 4(6): 2319-2333. Doi: 10.1039/C3SC22205E.
Chudasama et al. "Recent advances in the construction of antibody-drug conjugates." *Nat Chem* 2016, 8(2): 114-119.
Dassie et al. "Targeted Inhibition of Prostate Cancer Metastases with an RNA Aptamer to Prostate-specific Membrane Antigen." *Mol Ther* 2014, 22(11): 1910-1922.
Devaraj et al. "Tetrazine-based cycloadditions: application to pretargeted live cell imaging." *Bioconjug Chem* 2008, 19(12): 2297-2299.
DiPippo et al. "Efficacy studies of an antibody-drug conjugate PSMA-ADC in patient-derived prostate cancer xenografts." *Prostate* 2015, 75(3): 303-313.
Gomes, et al. "Cyclization-activated Pro Drugs" Molecules 2007, 12, 2484-2506.2.
Ji, et al. "Click and Release: Bioorthogonal Approaches to the "on-demand" Activation of Prodrugs" Chem. Soc. Rev. 2019, 48, 1077-1094. PMID: 30724944.
Ji and Wang, "Strategies toward Organic Carbon Monoxide Prodrugs" *Acc. Chem. Res.* 2018, 51, 13-77-1385.
Jin et al. "Discovery of PSMA-specific peptide ligands for targeted drug delivery." *Int J Pharm* 2016, 513(1-2): 138-147.
Kislukhin, et al. "Degradable Conjugates from Oxanorbornadiene Regents" Journal of the American Chemical Society *Am. Chem. Soc.* 2012, 134, 6491-6497.
Matikonda, et al. "*Bioorthogonal prodrug activation driven by a strain-promoted 1,3-dipolar cycloaddition*" Chem. Sci., 2015, 6, 1212.
Murphy et al. "Targeting Antioxidants to Mitochondria by Conjugation to Lipophilic Cations." *Ann Rev Pharmacol Toxicol* 2007, 47: 629-656.
Philip et al. "Colon Targeted Drug Delivery Systems: A Review on Primary and Novel Approaches." Oman Med J 2010, 25(2): 79-87.
Sakhrani and Padh, "Organelle targeting: third level of drug targeting" Drug Design Development and Therapy Jul. 15, 2013.
Shan et al. "Prodrug Strategies Based on Intramolecular Cyclization Reactions." *J Pharm Sci* 1997, 86: 765-767.
Sletten, and Bertozzi "Bioorthogonal Chemistry: Fishing for Selectivity in a Sea of Functionality" *Angew Chem Int Ed Engl.* 2009; 48(38): 6974-6998. Doi: 10.1002/anie.200999942.
Smith et al. "Delivery of bioactive molecules to mitochondria in vivo." *Proc Natl Acad Sci USA* 2003, 100(9): 5407-5412.
Tripodo, et al. "New Perspectives in Cancer Therapy: The Biotin-Antitumor Molecule Conjugates." Medicinal Chemistry *Med Chem.* 2014, S1 http://dx.doi.org/10.4172/2161-0444.S1-004.
Wang et al. "3,6-Substituted-1,2,4,5-tetrazines: Tuning Reaction Rates for Staged Labeling Applications." *Org Biomol Chem* 2014, 12: 3950-3955.
Wu, et al. "Selective Sensing of Saccharides using simple boronic acids and their aggregates" Chem. Soc. Rev., 2013, 42, 8032.
Yang, et al. "Making smart drugs smarter: The importance of linker chemistry in targeted drug delivery" Med. Res. Rev. 2020, manuscript accepted, doi.org/10.1002/med.21720.
Zhao et al. "Targeted drug delivery via folate receptors." *Expert Opin Drug Deliv* 2008, 5(3): 309-319.
Zwicke et al. "Utilizing the folate receptor for active targeting of cancer nanotherapeutics." *Nano Rev* 2012, 3: 18496-18507.

\* cited by examiner

ENRICHMENT-TRIGGERED CHEMICAL DELIVERY SYSTEM

CROSS-REFERENCES TO RELATED APPLICATIONS

The present application claims priority to U.S. Provisional Pat. Appl. No. 62/577,058, filed on Oct. 25, 2017, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Aug. 24, 2020, is named 056777-000810US-1188993_SL.txt and is 4,398 bytes in size.

BACKGROUND OF THE INVENTION

Prodrug strategies have been widely used to address delivery problems associated with pharmaceuticals. Essentially all such approaches have one goal, i.e., to deliver a drug to a desired location at a sufficiently high concentration. Prodrug efforts focused on improving physicochemical properties allow for enhanced permeability and solubility. Site-selective activation allows for targeting based on environmental factors such as pH; unique redox chemistry including levels of $H_2O_2$, glutathione, and other thiol species; and elevated levels of enzymes such as esterases, proteases, and phosphatases. In addition, gut bacteria also present unique redox chemistry and an active enzymatic environment for site-selective targeting. In recent years, targeted drug delivery has quickly gained attention with some remarkable success, especially in the field of cancer with the goal being minimizing toxicity. For example, antibody-drug conjugates allow for targeted delivery of drugs to the desired site. See, e.g., Rossin et al. *Bioconjug Chem* 2016, 27(7): 1697-1706; Agarwal et al. *Bioconjug Chem* 2015, 26(2): 176-192; Kern et al. *J Am Chem Soc* 2016, 138(4): 1430-1445; and Chudasama et al. *Nat Chem* 2016, 8(2): 114-119. Other targeting molecules can be used to hone in on biomarkers such as the high affinity folate receptor, carbohydrate biomarkers, and prostate-specific membrane antigen (PSMA). These targeted approaches can increase the concentration of the drug conjugates and prodrugs at the desired site, but achieving controlled release after enrichment is still a significant challenge. See, e.g., Zwicke et al. *Nano Rev* 2012, 3: 18496-18507; Zhao et al. *Expert Opin Drug Deliv* 2008, 5(3): 309-319; Ahmed et al. *Nanomedicine* 2015, 10(14): 2263-2288; DiPippo et al. *Prostate* 2015, 75(3): 303-313; Jin et al. *Int J Pharm* 2016, 513(1-2): 138-147; Dassie et al. *Mol Ther* 2014, 22(11): 1910-1922. Improved delivery systems for pharmaceuticals and other cargo are therefore needed, and systems that are not limited to delivery at cell surfaces—as in the case of antibody-drug conjugates—are particularly desired. The present invention addresses this and other needs.

BRIEF SUMMARY OF THE INVENTION

In one aspect, the invention provides a chemical delivery system having:
i) a cargo compound comprising a first reactive moiety covalently bonded to a first enrichment moiety and a tethered cargo moiety, wherein the first reactive moiety is bonded to the tethered cargo moiety via a cleavable linker; and
ii) a trigger compound comprising a second reactive moiety covalently bonded to a second enrichment moiety and a cargo-releasing moiety;
wherein:
the first enrichment moiety and the second enrichment moiety cause an increase in concentration of the cargo compound and the concentration of the trigger compound at a target site;
the first reactive moiety and the second reactive moiety are substantially unreactive toward one another without the increase in concentration of the cargo compound and the increase in concentration of the trigger compound at the target site;
the increase in concentration of the cargo compound and the increase in concentration of the trigger compound at the target site cause a bimolecular reaction between the first reactive moiety and the second reactive moiety to form a cyclization precursor compound; and
the cargo moiety is released from the cyclization precursor compound in a unimolecular cyclization reaction.

In some embodiments, the first reactive moiety is a tetrazine and the second reactive moiety is a cyclooctyne. In some embodiments, the enrichment moieties are mitochondrion-targeting moieties. In some embodiments, the unimolecular cyclization reaction results in the formation of a lactone. In some embodiments, the cargo moiety is a drug moiety.

In another aspect, the invention provides a pharmaceutical composition containing a chemical delivery system as described herein and a pharmaceutically acceptable excipient.

In another aspect, the invention provides a method for treating a disease or condition in a subject. The method includes administering an effective amount of a chemical delivery system as described herein to the subject. In some embodiments, the disease or condition is cancer, inflammation, and/or a bacterial infection.

DETAILED DESCRIPTION OF THE INVENTION

I. General

Figure 1:
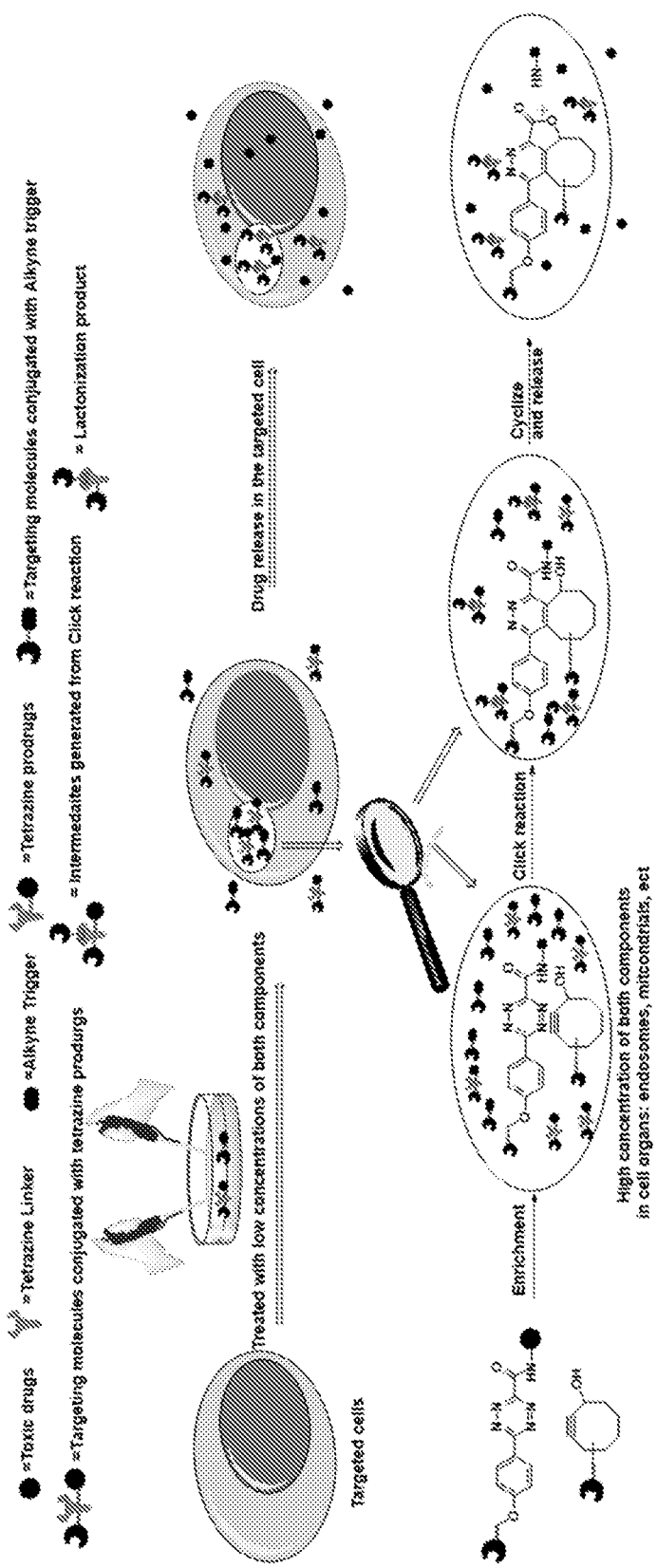
FIG. 1 shows the general approach for drug release based on reaction kinetics, leading to enrichment triggered release.

Targeted delivery to a desired site in a patient and controlled drug release at that site are important components of prodrug-based therapies. Through the use of targeting molecules such as antibodies, selective delivery of a drug to a desired site can be achieved. However, achieving triggered drug release only at the site of action while ensuring prodrug stability in the general circulation is a major challenge. Currently available methods including pH-, enzyme-, and redox-sensitive methods are applicable in unique situations. Disclosed herein is a concentration-sensitive platform approach for biorthogonal prodrug activation which takes advantage of reaction kinetics. Using a "click and release" system, wherein both cargo compounds and trigger compound contain targeted enrichment moieties, drug enrichment in target sites such as mitochondria can be achieved. A payload such as doxorubicin can be released inside the mitochondrial matrix upon the enrichment-initiated click reaction. Importantly, targeted delivery upon enrichment yields substantial augmentation of functional biological and therapeutic effects in vitro and in vivo, as compared to those without enrichment. Furthermore, the system described herein is not limited to cell-surface delivery as in the case of certain protein conjugates. The system can reduce the toxicity of anti-cancer drugs and other compounds, providing safer therapeutic agents and improved therapeutic methods.

II. Definitions

As used herein, the term "enrichment moiety" refers to a functional group that provides an increase in the concentration of a compound containing the enrichment moiety at a target site.

As used herein, the term "target site" refers to a location at which chemical concentration is desired or otherwise intended. For example, a target site can be a subcellular location in a subject to whom a compound is administered, such as a mitochondrion or other organelle. The target site can also be an organ or tissue.

As used herein, the term "substantially unreactive" indicates that a particular compound has not reacted in a way that provides an observable effect (e.g., a compound has not released a detectable amount of free cargo). In certain instances, cargo compounds and trigger compounds are considered substantially unreactive when they have not reacted with each other so as to release a drug cargo and cause a therapeutic effect or other medical effect, such as an adverse event. In certain instances, "substantially unreactive" indicates that a particular compound (e.g., a cargo compound as described herein) remains in its unreacted step prior to being subjected to particular conditions (e.g., contact with another compound such as a trigger compound as disclosed herein) or prior to undergoing a particular process (e.g., enrichment as described herein). In general, greater than 50% (weight % or mole %) of a substantially unreactive cargo compound or a substantially unreactive trigger compound will remain in its unreacted state prior to enrichment at a target site. For example, at least 51%, 55%, 60%, 65%, 70%, 75%, 80%, 85%, 90%, 91%, 92%, 93%, 94%, 95%, 96%, 97%, 98%, or 99% of the substantially unreactive compound may remain in its unreacted state prior to enrichment at the target site. In certain embodiments, all of the substantially unreactive compound remains in its unreacted state prior to enrichment at the target site.

As used herein, the term "bimolecular reaction" refers to a reaction involving two separate reactant compounds (e.g., a cargo compound and a trigger compound). A "unimolecular reaction" refers to a reaction involving two functional groups in the same compound (e.g., a cyclization reaction involving reaction of a cargo-releasing moiety with a cleavable linker).

As used herein, the term "tethered" refers to a molecular fragment that is covalently bonded to a compound such as a cargo compound disclosed herein. In general, the tethered fragment remains covalently bonded to the compound prior to enrichment at a target site.

As used herein, the term "cleavable linker" refers to a divalent functional group that covalently connects a tethered molecular fragment to a compound such a cargo compound disclosed herein. The cleavable linker is sufficiently labile for disruption of at least one covalent bond in the linker and release of the tethered cargo. Examples of cleavable linkers include, but are not limited to, esters, amides, carbonates, carbamates, disulfides, and sulfonates.

As used herein, the term "cargo-releasing moiety" refers to a functional group that is sufficiently reactive to form a covalent bond with a cleavable linker and displace a cargo moiety bonded to the cleavable linker. Examples of cargo-releasing moieties include, but are not limited to, hydroxyl groups, amino groups, and sulfhydryl groups.

As used herein, the term "alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. Unless otherwise specified, "substituted alkyl" groups can be substituted with one or more groups selected from halo, hydroxy, amino, alkylamino, amido, acyl, nitro, cyano, and alkoxy.

As used herein, the term "alkoxy," by itself or as part of another substituent, refers to a group having the formula —OR, wherein R is alkyl as described above.

As used herein, the term "cycloalkyl," by itself or as part of another substituent, refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. Unless otherwise specified, "substituted cycloalkyl" groups can be substituted with one or more groups selected from halo, hydroxy, amino, alkylamino, amido, acyl, nitro, cyano, and alkoxy.

As used herein, the term "alkylene" refers to an alkyl group, as defined above, linking at least two other groups (i.e., a divalent alkyl radical). The two moieties linked to the alkylene group can be linked to the same carbon atom or different carbon atoms of the alkylene group.

As used herein, the terms "halo" and "halogen," by themselves or as part of another substituent, refer to a fluorine, chlorine, bromine, or iodine atom.

As used herein, the term "haloalkyl," by itself or as part of another substituent, refers to an alkyl group where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

As used herein, the term "aryl," by itself or as part of another substituent, refers to an aromatic ring system having any suitable number of carbon ring atoms and any suitable number of rings. Aryl groups can include any suitable number of carbon ring atoms, such as $C_6$, $C_7$, $C_8$, $C_9$, $C_{10}$, $C_{11}$, $C_{12}$, $C_{13}$, $C_{14}$, $C_{15}$ or $C_{16}$, as well as $C_{6-10}$, $C_{6-12}$, or $C_{6-14}$. Aryl groups can be monocyclic, fused to form bicyclic (e.g., benzocyclohexyl) or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. Unless otherwise specified, "substituted aryl" groups can be substituted with one or more groups selected from halo, hydroxy, amino, alkylamino, amido, acyl, nitro, cyano, and alkoxy.

As used herein, the term "heteroaryl," by itself or as part of another substituent, refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can be oxidized to form moieties such as, but not limited to, —S(O)— and —S(O)$_2$—. Heteroaryl groups can include any number of ring atoms, such as $C_{5-6}$, $C_{3-8}$, $C_{4-8}$, $C_{5-8}$, $C_{6-8}$, $C_{3-9}$, $C_{3-10}$, $C_{3-11}$, or $C_{3-12}$, wherein at least one of the carbon atoms is replaced by a heteroatom. Any suitable number of heteroatoms can be included in the heteroaryl groups, such as 1, 2, 3, 4; or 5, or 1 to 2, 1 to 3, 1 to 4, 1 to 5, 2 to 3, 2 to 4, 2 to 5, 3 to 4, or 3 to 5. For example, heteroaryl groups can be $C_{5-8}$ heteroaryl, wherein 1 to 4 carbon ring atoms are replaced with heteroatoms; or $C_{5-8}$ heteroaryl, wherein 1 to 3 carbon ring atoms are replaced with heteroatoms; or $C_{5-6}$ heteroaryl, wherein 1 to 4 carbon ring atoms are replaced with heteroatoms; or $C_{5-6}$ heteroaryl, wherein 1 to 3 carbon ring atoms are replaced with heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. Unless otherwise specified, "substituted heteroaryl" groups can be substituted with one or more groups selected from halo, hydroxy, amino, alkylamino, amido, acyl, nitro, cyano, and alkoxy.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

As used herein, the term "heterocyclyl," by itself or as part of another substituent, refers to a saturated ring system having from 3 to 12 ring members and from 1 to 4 heteroatoms of N, O and S. Additional heteroatoms can also be useful, including, but not limited to, B, Al, Si and P. The heteroatoms can be oxidized to form moieties such as, but not limited to, —S(O)— and —S(O)$_2$—. Heterocyclyl groups can include any number of ring atoms, such as, $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, or $C_{3-12}$, wherein at least one of the carbon atoms is replaced by a heteroatom. Any suitable number of carbon ring atoms can be replaced with heteroatoms in the heterocyclyl groups, such as 1, 2, 3, or 4, or 1 to 2, 1 to 3, 1 to 4, 2 to 3, 2 to 4, or 3 to 4. The heterocyclyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocyclyl groups can also be fused to aromatic or non-aromatic ring systems to form members including, but not limited to, indoline. Heterocyclyl groups can be unsubstituted or substituted. Unless otherwise specified, "substituted heterocyclyl" groups can be substituted with one or more groups selected from halo, hydroxy, amino, oxo, alkylamino, amido, acyl, nitro, cyano, and alkoxy.

The heterocyclyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocyclyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocyclyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

As used herein, the term "amino" refers to a moiety —$NR_2$, wherein each R group is H or alkyl. An amino moiety can be ionized to form the corresponding ammonium cation. "Dialkylamino" refers to an amino moiety wherein each R group is alkyl.

As used herein, the term "sulfonyl" refers to a moiety —$SO_2R$, wherein the R group is alkyl, haloalkyl, or aryl. An amino moiety can be ionized to form the corresponding ammonium cation. "Alkylsulfonyl" refers to an amino moiety wherein the R group is alkyl.

As used herein, the term "hydroxy" refers to the moiety —OH.

As used herein, the term "cyano" refers to a carbon atom triple-bonded to a nitrogen atom (i.e., the moiety —C≡N).

As used herein, the term "carboxy" refers to the moiety —C(O)OH. A carboxy moiety can be ionized to form the corresponding carboxylate anion.

As used herein, the term "amido" refers to a moiety —NRC(O)R or —C(O)$NR_2$, wherein each R group is H or alkyl.

As used herein, the term "nitro" refers to the moiety —$NO_2$.

As used herein, the term "oxo" refers to an oxygen atom that is double-bonded to a compound (i.e., O=).

As used herein, the term "salt" refers to acid or base salts of the compounds of the invention. Illustrative examples of pharmaceutically acceptable salts include mineral acid salts (salts of hydrochloric acid, hydrobromic acid, phosphoric acid, and the like), organic acid salts (salts of acetic acid, propionic acid, glutamic acid, citric acid and the like) salts, and quaternary ammonium salts (salts of methyl iodide, ethyl iodide, and the like). It is understood that the pharmaceutically acceptable salts are non-toxic. Additional information on suitable pharmaceutically acceptable salts can be found in *Remington: The Science & Practice of Pharmacy*, 20th ed., Lippincott Williams & Wilkins, Philadelphia, Pa., 2000, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Compounds of the present invention include all tautomers and stereoisomers thereof, either in admixture or in pure or substantially pure form. The compounds of the present invention can have asymmetric centers at the carbon atoms, and therefore the compounds of the present invention can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Any compound or formula given herein, is intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I and $^{125}$I, respectively. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes deuterated analogs of compounds described herein in which from 1 to n hydrogens attached to a carbon atom is/are replaced by deuterium, in which n is the number of hydrogens in the molecule. Such compounds exhibit increased resistance to metabolism and are thus useful for increasing the half-life of any compound when administered to a mammal, particularly a human. See, for example, Foster, "Deuterium Isotope Effects in Studies of Drug Metabolism," *Trends Pharmacol. Sci.* 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F, $^3$H, $^{11}$C labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

As used herein, the term "pharmaceutical composition" is intended to encompass a product comprising the specified ingredients in the specified amounts, as well as any product, which results, directly or indirectly, from combination of the specified ingredients in the specified amounts.

As used herein, the term "pharmaceutically acceptable excipient" refers to a substance that aids the administration of an active agent to a subject. By "pharmaceutically acceptable," it is meant that the excipient is compatible with the other ingredients of the formulation and is not deleterious to the recipient thereof. Pharmaceutical excipients useful in the present invention include, but are not limited to, binders, fillers, disintegrants, lubricants, glidants, coatings, sweeteners, flavors and colors.

As used herein, the terms "treat", "treating," and "treatment" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom. The treatment or amelioration of symptoms can be based on any objective or subjective parameter, including, e.g., the result of a physical examination.

As used herein, the terms "effective amount" and "therapeutically effective amount" refer to a dose of a compound, such as a cargo compound and/or a trigger compound as disclosed herein, that brings about a result, e.g., a therapeutic effect, for which the compound was administered. When "effective amount" is used to describe an in vivo method, the desired result can refer to a therapeutic effect. When "effective amount" is used to describe an ex vivo method the desired results can refer to a detectable level of released drug cargo. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); *Goodman & Gilman's The Pharmacological Basis of Therapeutics*, 11$^{th}$ Edition, 2006, Brunton, Ed., McGraw-Hill; and *Remington: The Science and Practice of Pharmacy*, 21$^{st}$ Edition, 2005, Hendrickson, Ed., Lippincott, Williams & Wilkins).

The terms "about" and "around," as used herein to modify a numerical value, indicate a close range surrounding that explicit value. If "X" were the value, "about X" or "around X" would indicate a value from 0.9X to 1.1X. "About X" thus includes, for example, a value from 0.95X to 1.05X, or from 0.98X to 1.02X, or from 0.99X to 1.01X. Any reference to "about X" or "around X" specifically indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.07X, 1.08X, 1.09X, and 1.10X. Accordingly, "about X" and "around X" are intended to teach and provide written description support for a claim limitation of, e.g., "0.98X."

III. Enrichment-Triggered Chemical Delivery Compounds

Disclosed herein is a concentration-sensitive platform for prodrug activation, wherein the reaction kinetics of bioorthogonal "click chemistry" is used to control the activation process. Linker chemistry is used to tether a cargo (e.g., a drug or other active agent) to a targeting molecule in a stable fashion, and to allow for selective cleavage at the desired site of action upon administration to a subject.

Accordingly, one aspect of the invention provides a chemical delivery system having:
i) a cargo compound comprising a first reactive moiety covalently bonded to a first enrichment moiety and a tethered cargo moiety, wherein the first reactive moiety is bonded to the tethered cargo moiety via a cleavable linker; and ii) a trigger compound comprising a second reactive moiety covalently bonded to a second enrichment moiety and a cargo-releasing moiety;
wherein:
the first enrichment moiety and the second enrichment moiety cause an increase in concentration of the cargo compound and the concentration of the trigger compound at a target site;
the first reactive moiety and the second reactive moiety are substantially unreactive toward one another without the increase in concentration of the cargo compound and the increase in concentration of the trigger compound at the target site;
the increase in concentration of the cargo compound and the increase in concentration of the trigger compound at the target site cause a bimolecular reaction between the first reactive moiety and the second reactive moiety to form a cyclization precursor compound; and
the cargo moiety is released from the cyclization precursor compound in a unimolecular cyclization reaction.

The chemical delivery systems of the invention contain reactive partners (i.e., cargo compounds and trigger compounds) that undergo bioorthogonal reactions with tunable release rates, setting the stage for the subsequent release of a drugs or other chemical cargo. The rate of reaction can be tuned over several orders of magnitude. Tetrazines, for example, are known to react with trans-cyclooctenes and strained cyclooctynes with second order rate constants ranging from 0.0001 $M^{-1}s^{-1}$ to more than 1000 $M^{-1}s^{-1}$. The reaction rate of the trigger compound with the cargo compound can therefore be matched with a cargo property (e.g., drug activity) to achieve cargo delivery with a desired parameter (e.g., therapeutic efficacy). For example, the chemical delivery systems can be used for delivery of active agents having $IC_{50}$ values ranging from low micromolar concentrations to subnanomolar concentrations. A non-limiting scenario includes the use of a trigger compound and a cargo compound at a concentration of 10 µM in cell culture, without cytotoxicity until kinetically-controlled release is triggered. In this scenario, a second order rate constant around 0.25 $M^{-1}s^{-1}$ would provide a first half-life over 100 h without enrichment (i.e., at 10 µM). The enrichment moieties present in the trigger compound and the cargo compound cause an increase in concentration at a target site. Increasing the concentration of the trigger compound and the cargo compound by around 50 fold, to 500 µM, would lead to a decrease in its first half-life to about 2.2 h. As such, the chemical delivery system is essentially non-toxic to cells until enrichment-triggered release. The concept is presented in FIG. 1, which depicts the delivery system going through targeted enrichment (e.g., mitochondrion-targeted enrichment), a kinetically-controlled click reaction (e.g., tetrazine/cyclooctyne reaction), and spontaneous cyclization-based release (e.g., lactonization-based release) of a drug cargo (e.g., doxorubicin).

As described above, the cargo compound and the trigger compound are substantially unreactive toward one another prior to enrichment at the target site, and the enrichment of the cargo compound and the trigger compound at the target site causes the reaction to form the cyclization precursor compound. The rate of the bimolecular reaction after the increase in concentration of the cargo compound and the concentration of the trigger compound at the target site is therefore higher than the rate of the bimolecular reaction without the increase in concentration.

In some embodiments, the concentration of the cargo compound and/or the concentration of the trigger compound at the target site will increase by 2-fold to about 1000-fold. The concentration of one or both compounds can increase, for example, by a factor ranging from about 2-fold to about 10-fold, or from about 10-fold to about 25-fold, or from about 25-fold to about 50-fold, or from about 50-fold to about 75-fold, or from about 75-fold to about 100-fold, or from about 100-fold to about 150-fold, or from about 150-fold to about 200-fold, or from about 200-fold to about 250-fold, or from about 250-fold to about 300-fold, or from about 300-fold to about 350-fold, or from about 350-fold to about 400-fold, or from about 400-fold to about-fold 450, or from about 450-fold to about 500-fold, or from about 500-fold to about 550-fold, or from about 550-fold to about 600-fold, or from about 600-fold to about 650-fold, or from about 650-fold to about 700-fold, or from about 700-fold to about 750-fold, or from about 750-fold to about 800-fold, or from about 800-fold to about-fold 850, or from about 850-fold to about 900-fold, or from about 900-fold to about-fold 950, or from about 950-fold to about 1000-fold. In some embodiments, the concentration of one or both compounds will increase by a factor ranging from about 5-fold to about 500-fold, or from about 50-fold to about 450-fold, or from about 100-fold to about 400-fold, or from about 150-fold to about 350-fold, or from about 200-fold to about 300-fold. In some embodiments, the concentration of one or both compounds will increase by a factor ranging from about 45-fold to about 55-fold, or from about 40-fold to about 60-fold, or from about 25-fold to about 75-fold, or from about 10-fold to about 90-fold, or from about 5-fold to about 100-fold.

In some embodiments, the rate of the bimolecular reaction after the increase in concentration of the cargo compound and the concentration of the trigger compound at the target site is at least 2-500 times the rate of the bimolecular reaction without the increase in concentration. The rate of the reaction upon enrichment can increase, for example, by a factor ranging from about 2 to about 10, with respect to the rate of the reaction without enrichment. The rate of the reaction upon enrichment can increase, for example, by a factor ranging from about 2 to about 10, or from about 10 to about 25, or from about 25 to about 50, or from about 50 to about 75, or from about 75 to about 100, or from about 100 to about 150, or from about 150 to about 200, or from about 200 to about 250, or from about 250 to about 300, or from about 300 to about 350, or from about 350 to about 400, or from about 400 to about 450, or from about 450 to about 500 with respect to the rate of the reaction without enrichment. The rate of the reaction upon enrichment can increase, for example, by a factor ranging from about 5 to about 500, or from about 50 to about 450, or from about 100 to about 400, or from about 150 to about 350, or from about 200 to about 300, with respect to the rate of the reaction without enrichment.

In some embodiments, the rate of the bimolecular reaction after the increase of concentration of the cargo compound and the concentration of the trigger compound at the target site is at least 20-50 times the rate of the bimolecular reaction without the increase in concentration. In some embodiments, the rate of the bimolecular reaction after the increase of concentration of the cargo compound and the concentration of the trigger compound at the target site is at least 20-50 times the rate of the bimolecular reaction without the increase in concentration, or at least 30-50 times the rate of the bimolecular reaction without the increase in concentration, or at least 40-50 times the rate of the bimolecular reaction without the increase in concentration.

The extent to which the bimolecular reaction increases upon enrichment will depend on factors including the level of enrichment and the second order rate constant of the reaction. In some embodiments, the second order rate constant for the bimolecular reaction ranges from about $10^{-5}$ $M^{-1}s^{-1}$ to about 120 $M^{-1}s^{-1}$. In some embodiments, the second order rate constant for the bimolecular reaction ranges from about $1.16 \times 10^{-5}$ $M^{-1}s^{-1}$ to about 116 $M^{-1}s^{-1}$. The second order rate constant for the bimolecular reaction can range, for example, from about $10^{-5}$ $M^{-1}s^{-1}$ to about $10^{-4}$ $M^{-1}s^{-1}$; or from about $10^{-4}$ $M^{-1}s^{-1}$ to about $10^{-3}$ $M^{-1}s^{-1}$; or from about $10^{-3}$ $M^{-1}s^{-1}$ to about $10^{-2}$ $M^{-1}s^{-1}$; or from about $10^{-2}$ $M^{-1}s^{-1}$ to about $10^{-1}$ $M^{-1}s^{-1}$; or from about $10^{-1}$ $M^{-1}s^{-1}$ to 1 $M^{-1}s^{-1}$, or from about 1 $M^{-1}s^{-1}$ to about 10 $M^{-1}s^{-1}$; or from about 10 $M^{-1}s^{-1}$ to about 100 $M^{-1}s^{-1}$; or from about 100 $M^{-1}s^{-1}$ to about 120 $M^{-1}s^{-1}$. The second order rate constant can range from about 0.15 $M^{-1}s^{-1}$ to about 0.35 $M^{-1}s^{-1}$; or from about 0.2 $M^{-1}s^{-1}$ to about 0.4 $M^{-1}s^{-1}$; or from about 0.1 $M^{-1}s^{-1}$ to about 0.5 $M^{-1}s^{-1}$; or from about 0.05 $M^{-1}s^{-1}$ to about 1 $M^{-1}s^{-1}$; or from about $10^{-2}$ $M^{-1}s^{-1}$ to about 10 $M^{-1}s^{-1}$; or from about $10^{-3}$ $M^{-1}s^{-1}$ to about 50 $M^{-1}s^{-1}$; or from about $10^{-4}$ $M^{-1}s^{-1}$ to about 100 $M^{-1}s^{-1}$. In some embodiments, the second order rate constant for the bimolecular reaction is about 0.1 $M^{-1}s^{-1}$, or about 0.2 $M^{-1}s^{-1}$, or about 0.3 $M^{-1}s^{-1}$, or about 0.4 $M^{-1}s^{-1}$, or about 0.5 $M^{-1}s^{-1}$. The second order rate constant can be tuned by tailoring the structure of elements including, but not limited to, the first reactive moiety, the second reactive moiety, and the cargo-releasing moiety as described in more detail below.

Enrichment Moieties

The enrichment moieties in the cargo compound and the trigger compound cause an increase in concentration of the compounds at a target site. In the case of drug delivery to a patient, the enrichment moieties provide enrichment at an organ, tissue, cell (e.g., a tumor cell or an infected cell), organelle, and/or other subcellular compartment/component. The enrichment can be modulated through the selection of a enrichment moieties with the appropriate affinity and specificity. Examples of enrichment moieties include, but are not limited to peptide moieties, nucleic acid moieties, lipid moieties, and saccharide moieties.

Enrichment moieties can contain B vitamins, such as folic acid/folate (vitamin B9) and biotin (vitamin B7). Folate moieties (i.e., N-(4-{[(2-amino-4-oxo-1,4-dihydropteridin-6-yl)methyl]amino}benzoyl)-L-glutamic acid and derivatives thereof, such as ester or amide derivatives) can be used to provide enrichment at tissues expressing folate receptors. It is estimated that folate receptors are overexpressed on around 40% of human cancers, so folate moieties are useful for providing compound enrichment at tumor tissue and treating cancer. Examples of cancers that can be treated include, but are not limited to, carcinomas, sarcomas, lymphomas, Hodgkin's disease, melanomas, mesotheliomas, Burkitt's lymphoma, nasopharyngeal carcinomas, leukemias, and myelomas. The cancer can affect oral tissues, the thyroid, the endocrine system, the skin, the gastric system, the esophagus, larynx, pancreas, colon, bladder, bone, ovaries, cervix, uterus, breast, testes, prostate, rectum, kidneys, liver, or lungs. The sodium-dependent multivitamin transporter (SMVT) has also been found to be overexpressed in a number of cancers including leukemia, ovarian cancer, colon cancer, mastocytoma, lung cancer, renal cancer, and breast cancer. SMVT is a transporter for biotin, so biotin moieties (i.e., 5-[(3aS,4S,6aR)-2-oxohexahydro-1H-thieno[3,4-d]imidazol-4-yl]pentanoic acid and derivatives thereof, such as ester or amide derivatives) can be used to provide enrichment at tissues expressing SMVT.

Peptides containing an arginine-glycine-aspartic acid (RGD) tripeptide sequence can be used to provide enrichment at tissues characterized by the presence of $\alpha v \beta 3$ integrins, which are expressed on the surface of various normal and cancer cell types and which are involved in multiple physiological processes including angiogenesis, apoptosis, and bone resorption. The cargo compound and/or the trigger compound can include enrichment moieties containing linear RGD peptides, cyclic RGD peptides (e.g., cilengitide), and derivatives thereof as described, for example in U.S. Pat. Nos. 6,001,961; 7,030,213; and 9,115,170.

Glucose moieties (i.e., (2R,3S,4R,5R)-2,3,4,5,6-pentahydroxyhexanal, and glycans containing glucose) can be used to provide enrichment in tissues expressing glucose transporters (GLUTs). GLUTs vary in terms of their kinetics and affinities towards glucose and other hexoses, and the expression level can depending on the metabolic consumption of glucose by the particular tissue type. A high rate of glucose uptake and increased glucose metabolism are frequently involved in maintaining proliferation of tumor cells, a phenomenon known as the Warburg effect. GLUT1 and GLUT3, in particular, have been observed to be present at higher levels in a wide variety of cancerous cells than in normal cells.

Boronic acid moieties (including phenylboronic acids, phenyl(diboronic acids), boroxoles, and bis(boroxoles), and the like) can provide enrichment at tissues expressing carbohydrate antigens such as Tn antigens (i.e., glycosides containing GalNAc), Thomsen-Friedenreich antigens (i.e., glycosides containing Gal-β1,3-GalNAc), and various sialosides (e.g., glycosides containing Neu5Ac or other sialic acids, including sialyl Lewis X). In such cases, non-covalent binding of boronic acids to diols present in the carbohydrates leads to the desired enrichment. Examples of suitable boronic acid moieties include, but are not limited to, those described in U.S. Pat. Nos. 559,411; 6,008,406; 6,031,117; and 9,234,048.

In certain cases, the enrichment moiety can include a suitable antibody or antibody fragment. For example, five human antibody classes (IgG, IgA, IgM, IgD and IgE), and within these classes, various subclasses, are recognized on the basis of structural differences, such as the number of immunoglobulin units in a single antibody molecule, the disulfide bridge structure of the individual units, and differences in chain length and sequence. An enrichment moiety may contain an antibody or antibody fragment from any of these classes. The enrichment moiety can contain an antigen-binding antibody fragment such as, for example, an Fab, an F(ab'), an F(ab')$_2$, an Fd chain, a single-chain Fv (scFv), a single-chain antibody, a disulfide-linked Fv (sdFv), a fragment comprising either a $V_L$ or $V_H$ domain, or fragments produced by a Fab expression library. Typically, the antibodies will be human, rodent (e.g., mouse and rat), donkey, sheep, rabbit, goat, guinea pig, camelid, horse, or chicken antibodies. As used herein, "human" antibodies include antibodies having the amino acid sequence of a human immunoglobulin and include antibodies isolated from human immunoglobulin libraries, from human B cells, or from animals transgenic for one or more human immunoglobulin. The antibodies may be monospecific, bispecific, trispecific, or of greater multispecificity.

The antibodies may be directed against antigens of medical and/or therapeutic interest, such as those associated with pathogens (such as but not limited to viruses, bacteria, fungi, and protozoa), parasites, tumor cells, or particular medical conditions. In some embodiments, the enrichment moiety can contain an antibody known for the treatment or prevention of cancer. Examples of antibodies for the treatment of cancer include, but are not limited to, trastuzumab (HERCEPTIN; Genentech; a humanized anti-HER2 monoclonal antibody for the treatment of patients with metastatic breast cancer); rituximab (RITUXAN; Genentech; a chimeric anti-CD20 monoclonal antibody for the treatment of patients with non-Hodgkin's lymphoma); bevacizumab (AVASTIN; Genentech; a humanized monoclonal IgG1 antibody that binds to human vascular endothelial growth factor (VEGF) for the treatment of colorectal cancer and other conditions); nivolumab (OPDIVO; Bristol-Meyers Squibb Co.; a human monoclonal antibody that blocks the interaction between PD-1 and its ligands, PD-L1 and PD-L2, for treatment of hepatocellular carcinoma and other conditions); pembrolizumab (KEYTRUDA; Merck & Co, Inc.; a humanized monoclonal antibody that blocks the interaction between PD-1 and its ligands, PD-L1 and PD-L2, for the treatment of gastric cancer and other conditions); and ipilimumab (YERVOY; Bristol-Meyers Squibb; a human monoclonal antibody that binds to the cytotoxic T-lymphocyte-associated antigen 4 (CTLA-4) for the treatment of melanoma and other conditions).

The enrichment moieties described herein can also contain aptamers, which are associated with a number of advantageous properties. For example, most aptamers bind to targets with high affinity, demonstrating typical dissociation constants in the pico- to nanomolar range. In addition, aptamers are structurally stable across a wide range of temperature and storage conditions, maintaining the ability to form their unique tertiary structures. Furthermore, aptamers can be chemically synthesized, in contrast to the expensive and work-intensive biological systems needed to produce monoclonal antibodies. Both RNA and DNA (or analog) aptamers are known, and aptamer binding is frequently depends on the secondary structure formed by the aptamer oligonucleotide. Methods for identifying, synthesizing, and using aptamers and aptamer-conjugate materials are described, for in example, in U.S. Pat Appl. Pub. Nos. 2017/0218369, US 2016/0355820, and US 2016/0003835, as well as U.S. Pat. Nos. 9,540,412; 9,243,024; 8,304,560; 7,803,931; 6,171,795; 6,127,119; 6,028,186; 5,773,598; 5,475,096; and 5,270,163.

Aptamer enrichment moieties will generally contain from about 10 nucleotides to about 150 nucleotides (i.e., ribonucleotides or deoxyribonucleotides). Aptamers can further include synthetic modifications to provide increased stability, such as increased resistance to cleavage by nucleases. Modified aptamers can include altered internucleotide linkages, altered sugars, altered bases, or combinations thereof. Such modifications include 2'-position sugar modifications; 5-position pyrimidine modifications; 8-position purine modifications; modifications at exocyclic amines; substitution of 4-thiouridine; substitution of 5-bromo or 5-iodouracil; backbone modifications; phosphorothioate or alkyl phosphate modifications; methylations; unusual base-pairing combinations such as the isobases isocytidine and isoguanosine; 3' and 5' modifications such as capping; conjugation to a high molecular weight, non-immunogenic compound (e.g., a polyalkylene glycol such as polyethylene glycol); conjugation to a lipophilic compound; and phosphate backbone modification (e.g., phosphorothioate incorporation). All of the foregoing can be incorporated into an aptamer using standard synthetic techniques.

The enrichment moieties disclosed herein can contain a prostate-specific membrane antigen ligand. Prostate-specific membrane antigen (PMSA, also referred to as glutamate carboxypeptidase II, N-acetyl-α-linked acidic dipeptidase I, and folate hydrolase) is expressed in prostate tumor epithelium as well as the neovasculature of many other solid tumor types. A number of synthetic PMSA ligands have been identified, including glutamate-derived hydroxyphosphinyl derivatives (e.g., phosphonomethylpentanedioic acid), phosphinic bisdicarboxylic acids (e.g., 4,4' phosphinicobis(butane-1,3-dicarboxylic acid)), glutamate-urea-glutamate dimers, and glutamate-urea heterodimers. Examples of PSMA-targeted compounds include, but are not limited to, those described in U.S. Pat. Nos. 9,776,977; 9,636,413; 8,487,129; and 6,479,470.

Accordingly, some embodiments of the invention provide chemical delivery systems wherein the first enrichment moiety and the second enrichment moiety are selected from the group consisting of a folic acid moiety, a biotin moiety, an RGD peptide, a glucose moiety, a boronic acid moiety, an antibody, an aptamer, and a prostate specific membrane antigen ligand moiety.

The first enrichment moiety and the second enrichment moiety may have the same chemical structure or difference chemical structures, provided that the different chemical structures lead to an increase in concentration of the cargo compound and the concentration of the trigger compound at the same target site. As a non-limiting example, the first enrichment moiety in some embodiments may be an integrin-targeting linear RGD peptide and the second enrichment moiety may be an integrin-targeting cyclic peptide such as cilengitide. Similarly, the first enrichment moiety in some embodiments may be a mitochondrion-targeting carnitine analog and the second enrichment moiety may be a mitochondrion-targeting triphenylphosphonium group.

As discussed above, the enrichment moieties can provide enrichment at a particular subcellular location such as an organelle or other compartment/component. For example, the enrichment moieties can include a cell penetrating peptide, a nucleus-targeting moiety, a mitochondrion-targeting moiety, a lysosome/endosome-targeting moiety, or a Golgi/endoplasmic reticulum-targeting moiety.

Examples of cell-penetrating peptides include, but are not limited to, synthetic peptides such as polyarginine as well as naturally-occurring sequences such as the HIV-1 Tat DNA binding domain and the HSV-1 VP22 protein. See, e.g., Li et al. *Biochem Biophys Res Commun.* 2002; 298(3): 439-449; Roeder, et al. *Biotechnol Appl Biochem.* 2004; 40(2): 157-165; and Futaki et al. *J Biol Chem.* 2001; 276(8); 5836-5840. Examples of nucleus-targeting moieties include, but are not limited to, peptides containing nuclear localization sequences such as KKKRKV (SEQ ID NO:1) and KRPAATKKAGQAKKKKL (SEQ ID NO:2) which are recognized by importins in the cytoplasm. Other nuclear localization sequences include PKKKRKV (SEQ ID NO:3); RRKRQR (SEQ ID NO:4); KRXXXXXXXXXXXXKKLR (SEQ ID NO:5); RKKRXXXXXXXXXXXXKKSK (SEQ ID NO:6); MNKIPIKDLLNPQ (SEQ ID NO:7); YLTQETNKVETYKEQPLKTPGKKKKGKP (SEQ ID NO:8); NQS SNFGPMKGGNFGGRS SGPYGGGGQYFAKPRNQGGY (SEQ ID NO: 9); SANKVTKNKSNSSPYLNKRKGKPGPDS (SEQ ID NO:10); VHSHKKKKIRTSPTFTTPKTLRLRRQPKYPRKSAPRRNKLDHY (SEQ ID NO:11); NAP-SAKATAAKKAVVKGTNGKKALKVRT- SATFRLPKTLKLAR (SEQ ID NO:12); and other sequences disclosed in U.S. Pat. Nos. 7,795,380 and 6,312,956.

The enrichment moieties can contain groups that provide enrichment in lysosomes. For example, lysosomal targeting can involve binding to the cation-independent M6P receptor which plays an important role in the trafficking of lysosomal enzymes through recognition of the M6P moiety on high mannose carbohydrate on lysosomal enzymes. The enrichment moieties can therefore include moieties that bind the cation-independent M6P receptor including, but not limited to, insulin-like growth factor 2 (IGF-II), retinoic acid, and urokinase-type plasminogen receptor (uPAR) as described in U.S. Pat. No. 7,396,811. Tyrosine-based motifs (e.g., YXXφ, wherein X is any amino acid and φ is a bulky hydrophobic amino acid) and leucine-based motifs (e.g., DEXXXLI (SEQ ID NO:13) or DXXLL (SEQ ID NO:14), wherein X is any amino acid) can also be used as lysosome-specific enrichment motifs. See, e.g., Behnke et al. *Biochem J.* 2011; 434(2):219-231 and Grubb et al. *Rejuvenation Res.* 2010; 13(2-3):229-236. Enrichment in the Golgi and/or endoplasmic reticulum can be provided by using a localization sequence from SV40, which binds to MHC class I receptors; cholera toxin, which binds to GM1 ganglioside molecules; or ricin, which binds to glycolipids and glycoproteins with terminal galactose on the surface of cells. The enrichment pathway may follow a variety of routes. For example, SV40 undergoes caveolar endocytosis and reaches the ER in a two-step process that bypasses the Golgi whereas cholera toxin undergoes caveolar endocytosis but traverses the Golgi before reaching the ER. Methods for reducing and/or limiting the toxicity of cholera toxin or ricin are advantageously employed, as described in U.S. Pat. No. 7,396,811.

In certain embodiments, the enrichment moiety is a mitochondrion-targeting moiety. Examples of mitochondrion-targeting moieties include positively-charged triphenylphosphonium groups (described, for example, in U.S. Pat. No. 6,331,532), tribenzylammonium and phosphonium groups (described, for example, in U.S. Pat. No. 7,888,334), and carnitine (γ-amino-(R)-β-hydroxybutyric acid trimethylbetaine) or carnitine analogs. Carnitine analogs include, but are not limited to (1S,2R,3R)-2-hydroxy-3-trimethyl-ammoniocyclohexane-carboxylate, (1S,2R,3S)-2-hydroxy-3-trimethylammoniocyclohexanecarboxylate, (1R,2R,3R)-2-hydroxy-3-trimethylammoniocyclohexanecarboxylate, (1R,2R,3S)-2-hydroxy-3-trimethylammoniocyclohexanecarboxylate, D-3'-deoxy-3'-trimethylammonioglucuronate, and D-3'-deoxy-3'-trimethylammonioalluronate (described, for example, in U.S. Pat. No. 6,316,652). Mitochondrion-specific enrichment moieties can also include peptidic mitochondrial targeting signals (MTS), which direct the transport of passenger polypeptides across the mitochondrial membranes and facilitate their anchoring in the mitochondrial membranes. Typically, MTS comprise charged, hydrophobic and hydroxylated amino acid residues. Examples of MTS include the N-terminal region of human cytochrome c oxidase subunit VIII, the N-terminal region of the P1 isoform of subunit c of human ATP synthase, or the N-terminal region of the aldehyde dehydrogenase targeting sequence. A number of MTS can be used, including those described in U.S. Pat. Nos. 9,260,495 and 9,139,628.

Accordingly, some embodiments of the invention provide a chemical delivery system wherein the first enrichment moiety and the second enrichment moiety are mitochondrion-targeting moieties. In some embodiments, the mitochondrion-targeting moiety is a positively charged phosphine (e.g., a triphenylphosphonium group).

Enrichment moieties can be covalently bonded to the cargo compounds and the trigger compounds using a variety of linker strategies. For example, an enrichment moiety can be bonded to a cargo compound or a trigger compound via a divalent linker -L-. In some embodiments, the divalent linker -L- has a structure -L$^1$-L$^2$-, wherein:

L$^1$ and L$^2$ are independently selected from a bond, a divalent polymer moiety, and linear or branched, saturated or unsaturated C$_{1-30}$ alkylene;

one or more carbon atoms in the C$_{1-30}$ alkylene are optionally and independently replaced by O, S, NR$^a$;

two or more groupings of adjacent carbon atoms in the C$_{1-30}$ alkylene are optionally and independently replaced by —NR$^a$(CO)— or —(CO)NR$^a$—; and two or more groupings of adjacent carbon atoms in the C$_{1-30}$ alkylene are optionally and independently replaced by a 4- to 8-membered, divalent carbocycle or a 4- to 8-membered, divalent heterocycle having one to four heteroatoms selected from O, S, and N;

and each R$^a$ is independently selected from H and C$_{1-6}$ alkyl.

Intermediate compounds containing azide groups (e.g., a cargo compound intermediate having an —N$_3$ group) can be reacted with a enrichment moiety reactant having a complementary functional group such as an alkyne or a phosphine. Reaction of azides and alkynes via [3+2] cycloaddition can be used to install a variety of enrichment moieties in the cargo compounds and/or trigger compounds of the invention. Accordingly, some embodiments of the invention provide compounds wherein linking moiety -L$^3$- is an optionally substituted triazolyl moiety according to the formula:

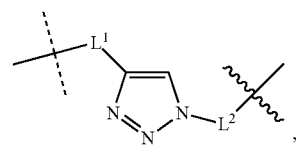

wherein L$^1$ and L$^2$ are as described above, and wherein the wavy line is point of connection to the enrichment moiety and the dashed line is the point of connection to the cargo compound or the trigger compound (e.g., the dashed line is the point of connection to the first reactive moiety or the second reactive moiety).

Reactive Moieties and Cargo-Releasing Moieties

In general, the cargo compound and the trigger compound contain reactive moieties which do not react with one another prior to enrichment and do not react with other substances in the environment where chemical delivery is targeted. In the case of drug delivery to a patient, the reactive moieties and unreactive (or reversibly reactive) with biological nucleophiles such as amines, thiols, and alcohols and other functional groups in the biological milieu. As discussed above, bioorthogonal "click" reactions are also characterized by tunable reaction kinetics that can be used to control release of cargo to a target site. A number of such bioorthogonal reactive pairs can be installed in the cargo compounds and trigger compounds disclosed herein. Examples of bioorthogonal reactive pairs include, but are not limited to: ketones/aldehydes and aminooxy compounds/hydrazides; azides and alkynes, including cyclooctynes; azides and phosphines, including triarylphosphines;

tetrazines and alkenes/alkynes, including trans-cyclooctenes, norbornenes, and cyclooctynes; cyclopentadienones and alkynes, including cyclooctynes; and thiophene 1,1-dioxides and alkenes.

The reactive pair is selected to provide a cyclization precursor compound upon reaction of the first reactive moiety and the second reactive moiety. In the cyclization precursor compound, the cargo-releasing moiety is positioned such that it can react with the cleavable linker to release the tethered cargo. A nucleophilic cargo-releasing moiety in the cyclization precursor compound (e.g., as a hydroxyl group or an amine) can be positioned within a suitable distance from an electrophile in the cleavable linker (e.g., a carbonyl group in an ester linker, amide linker, carbonate linker, or carbamate linker) for release of the cargo upon cyclization. For example, the cargo-releasing moiety and the cleavable linker may be positioned such that a stable five-membered, six-membered, or seven-membered ring is formed upon the unimolecular cyclization reaction.

Scheme 1 sets forth non-limiting examples of bioorthogonal reactive pairs: i.e., tetrazine/alkyne (Ii/IIi), tetrazine/alkene (Ii/IIIi), thiophene 1,1-dioxide/alkene (Iii/IIii), and cyclopentadienone/alkyne (Iiii/IIi). In Scheme 1, $R^1$ and $R^4$ are the first and second enrichment moieties, respectively, $R^3$ is a tethered cargo moiety, and $R^5$ is a cargo-releasing moiety.

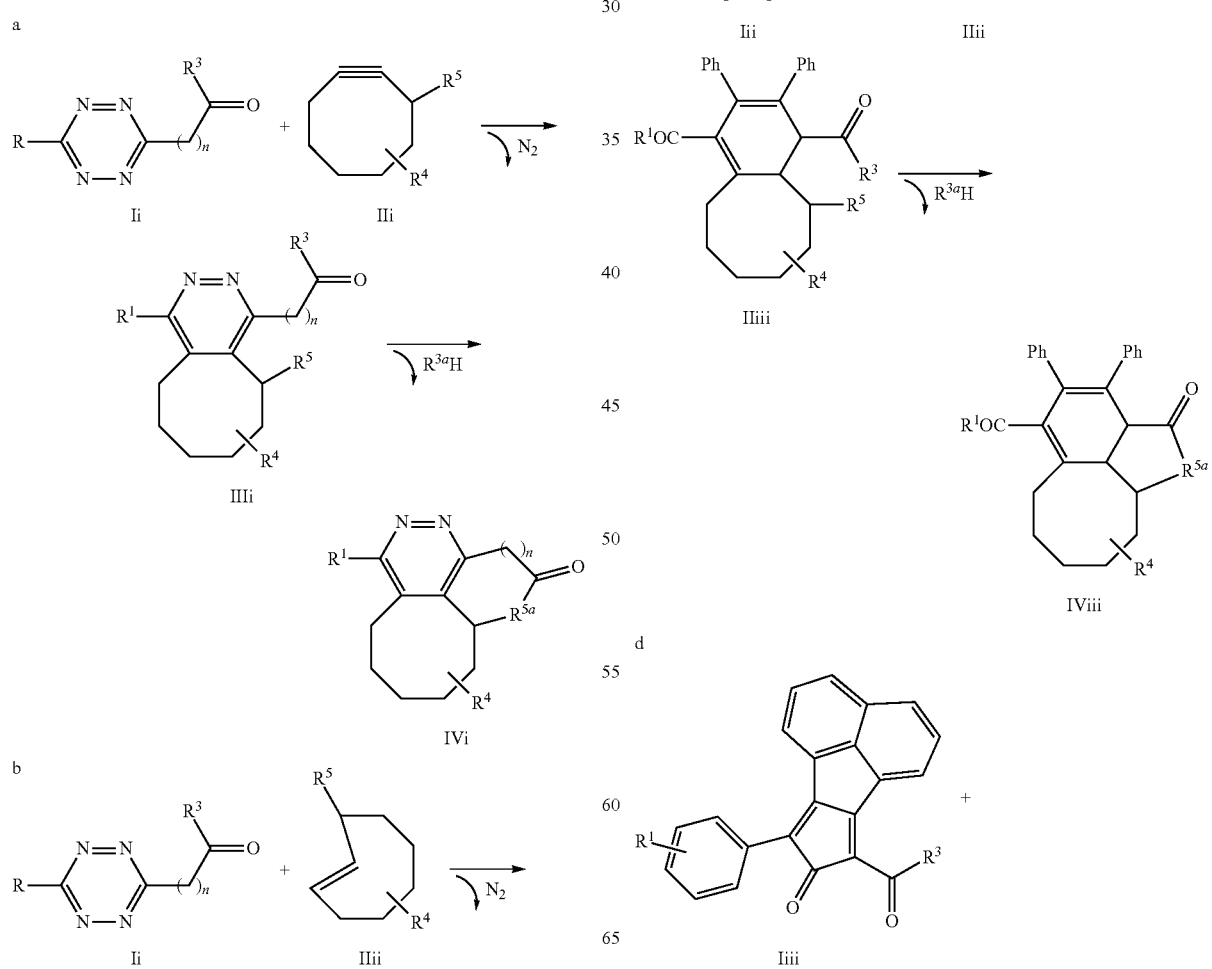

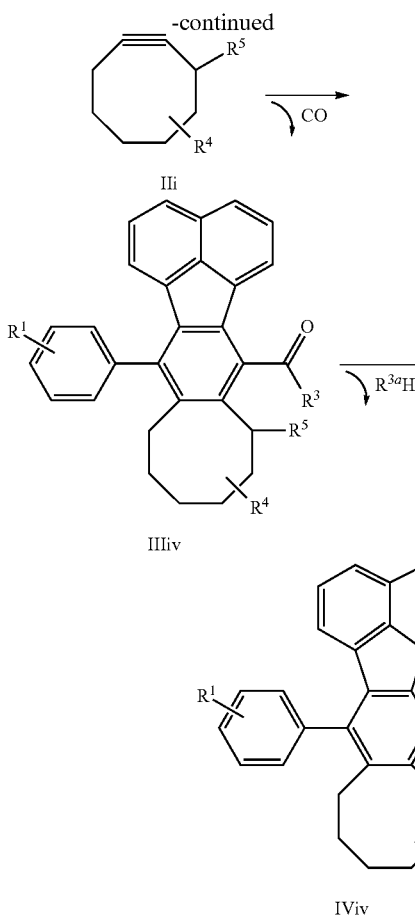

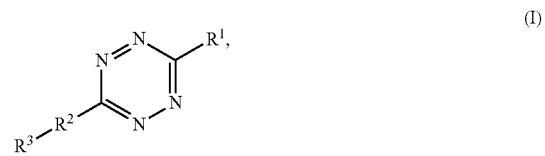

wherein $R^1$ is the first targeting moiety, $R^2$ is the cleavable linker, and $R^3$ is the tethered cargo moiety.

In some embodiments, the cargo compound has a structure according to Formula Ia:

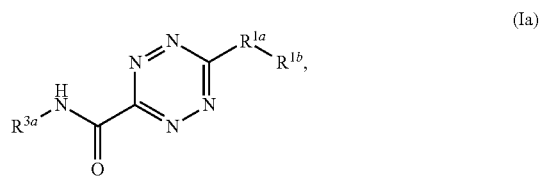

wherein $R^{1a}$ is a linking diradical, $R^{1b}$ is a targeting radical, and $R^{3a}$ is a cargo radical.

In some embodiments, the cargo compound has a structure according to Formula Ib:

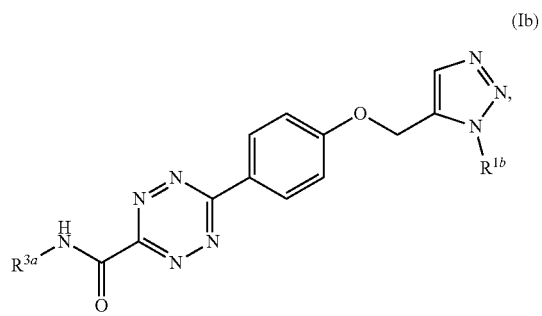

In some embodiments, the cargo compound has a structure according to Formula II:

wherein $R^4$ is the second targeting moiety and $R^5$ is the cargo-releasing moiety.

The bimolecular click reaction results in the loss of nitrogen, carbon monoxide, or sulfur dioxide and formation of a cyclization precursor compound (intermediate IIIi-IIIiv) containing tethered cargo moiety $R^3$ and cargo-releasing moiety $R^5$ properly situated for subsequent unimolecular cyclization and cargo release. For example, when an $R^5$ group in Scheme 1 is —OH, —SH, or —NH$_2$, the unimolecular cyclization reaction will result in the formation of a lactone, a thiolactone, or a lactam, respectively (e.g., compounds IVi-IViv in Scheme 1, where $R^{5a}$ is —O—, —S—, or —NH—). The lactone, thiolactone, or lactam generally contains 5-8 ring members. For example, subscript n in Scheme 1 can be 0, 1, 2, or 3. In some embodiments, the thiolactone, or the lactam comprises a five-membered ring or a six-membered ring. Typically, the cargo moiety will be released from the cleavable linker in the cargo compound in the form $R^{3a}H$, as shown in Scheme 1. Cargo molecules containing amine groups (e.g., doxorubicin or another amine containing drugs as set forth below) are advantageously tethered as amides $R^{3b}NHC(O)$—, wherein $R^{3b}$ is the non-amine portion of the cargo, and then released as free amines $R^{3b}NH_2$. Alternatively, amine-containing cargo can be tethered as a carbamate or a urea. Cargo molecules containing alcohol groups (e.g., paclitaxel or another alcohol containing drugs as set forth below) are advantageously tethered as esters $R^{3b}OC(O)$—, wherein $R^{3b}$ is the non-alcohol portion of the cargo, and then released as free alcohols $R^{3b}OH$. Alternatively, alcohol-containing cargo can be tethered as a carbamate or a carbonate. In certain embodiments, carbon monoxide released from a cyclopentadienone reactive moiety can also provide a therapeutic effect as described, for example, in Intl. Pat. Appl. Publ. No. WO 2015/191616. In certain instance, one or both of $R^1$ and $R^4$ can be a non-targeted moiety such as H, alkyl, and the like.

In some embodiments the invention provides a chemical delivery system as described above, wherein the first reactive moiety is selected from the group consisting of a tetrazine, a thiophene 1,1-dioxide, and a cyclopentadienone. In some embodiments, the second reactive moiety is selected from the group consisting of a cyclooctene and a cyclooctyne.

In some embodiments, the cargo compound has a structure according to Formula I:

In some embodiments, the trigger compound has a structure according to Formula IIa:

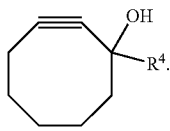
(IIa)

In some embodiments, the trigger compound has a structure according to Formula IIb:

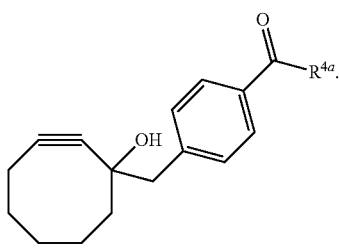
(IIb)

In some embodiments, the cargo compound is:

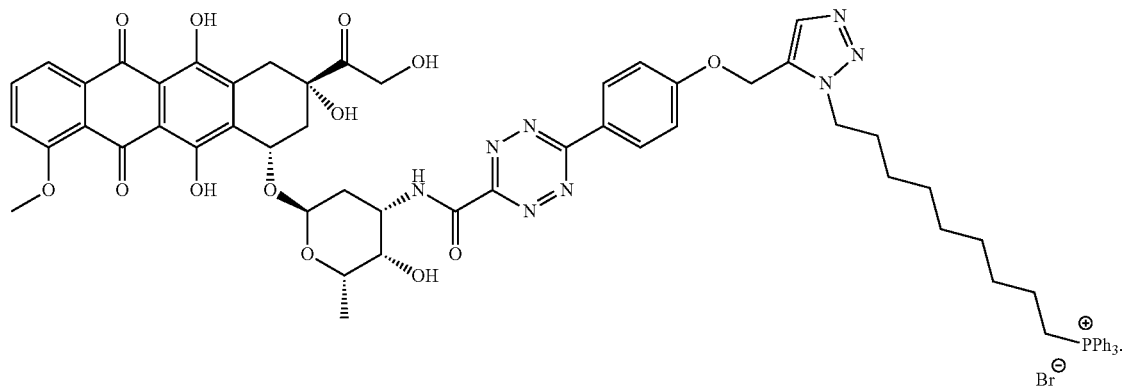

In some embodiments, the trigger compound is:

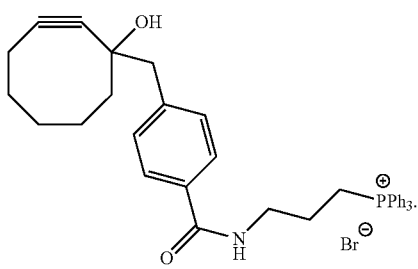

Cargo Moieties

In some embodiments, the cargo moiety is a drug moiety. Parent drugs selected from broad classes of compounds can be incorporated as tethered cargo moieties in the cargo compounds disclosed herein. Examples of such parent drugs include respiratory drugs, including antiasthmatic agents; analgesic agents; antidepressants; antianginal agents; antiarrhythmic agents; antihypertensive agents; antidiabetic agents; antihistamines; anti-infective agents such as antibiotics; anti-inflammatory agents; anti-Parkinson's drugs; antipsychotics; antiproliferative agents, including but not limited to antimetabolites, anti-microtuble agents, and topoisomerase inhibitors; antipyretic agents; antiulcer agents; attention deficit hyperactivity disorder (ADHD) drugs; central nervous system stimulants; cough and cold preparations, including decongestants; and psychostimulants.

Examples of amine-containing drugs include, but are not limited to, acebutalol, acebutolol, adaprolol, adrenolone, adrogolide, aladapcin, alatrofloxacin, albendazole, albuterol, albutoin, alendronate, alestramustine, aletamine, alinidine, aliskiren, alizapride, alniditan, alprafenone, alprenolol, alprenoxime, altromycin A, altromycin C, amantadine, a-methyltryptophan, amidephrine, amifostine, amikacin, amiloride, 21-aminoepothilone B, R-(+)-aminoindane, aminolevulinic acid, aminorex, amlodipine, amosulalol, amoxapine, amphetamine, amphotericin B, amrubicin, amselamine, amthamine, anabasine, angiopeptin, anisperimus, aprinocid, arbekacin, arbutamine, argiopine, arotinolol, aspartame, aspoxicillin, atenolol, avizafone, azoxybacilin, baclofen, bactobolin, balanol, balofloxacin, bambuterol, bamethan, baogongteng A, barusiban, batoprazine, becampanel, befunolol, belactosin A, belactosin C, benanomicin B, benazepril, berlafenone, betahistine, betaxolol, bevantolol, biemnidin, binospirone, bisoprolol, boholmycin, bopindolol, brasilicardin A, brinzolamide, bunolol, bupropion, butabindide, buteranol, butofilolol, butopamine, butoxamine, caldaret, cambendazole, cambrescidins, caprazamycin, capromorelin, capsavanil, carbidopa, carbuterol, cartelolol, carteolol, carvedilol, cefaclor, cefcanel, cefcanel daloxate, cefminox, cefprozil, ceftizoxime, celiprolol, ceranapril, cetefloxacin, chlorotetain, chlortermine, (−)-cicloprolol, cilazapril, cimaterol, cimetidine, cinacalcet, ciprofloxacin, circinamide, cisapride, cispentacin, clonidine, cloranolol, clorprenaline, colterol, cyclobenzadole, cyclothialidine, cystamine, cystocin, cytaramycin, dabelotine, dactimicin, dalargin, dalbavancin, daunorubicin, D-cycloserine, decaplanin, deferoxamine, delapril, delavirdine, delfaprazine, delucemine, demexiptiline, denopamine, deoxymethylspergualin, deoxynegamycin, deoxynojirimycin, deoxyspergualin, desipramine, desloratadine, deterenol, dexpropanolol, diacetolol, dihydrexidine, dilevalol, dimethoxyphenethylamine, dinapsoline, dirithromycin, dobutamine, donitriptan, dopamine, dopexamine, doripenem, dorzolamide, doxorubicin, droxidopa, droxinavir, duloxetine, duramycin, ecenofloxacin, ecteinascidins, efegatran, efegatrin, eflornithine, eglumegad, elarofiban, enalapril, enalkiren, enkastins, enoxacin, enviroxime, ephrinephrine, epibatidine, epirubicin, epithalon, eremomycin, ersentilide, ertapenem, esafloxacin, esmolol, esperamicin A1, etintidine, etryptamine, examorelin, exaprolol, exatecan, exprenolol, ezlopitant, fasudil, fenbendazole, fenfluramine, fenmetazole, fenoldopam, fenoterol, fenyripol, fepradinol, ferulinolol, flecamide, flubendazole, fludorex, fluoxetine, fluparoxan, fluvirucin B2, fluvoxamine, formoterol, fortimicin A, fosopamine, frovatriptan, fudosteine, gabapentin, gaboxadol, galarubicin, galnon, garenoxacin, garomefrine, gatifloxacin, gemifloxacin, gilatide, giracodazole, gludopa, halofuginone, helvecardin A, helvecardin B, hispidospermidin, histaprodifen, hydrostatin A, ibopamine, ibutamoren, icadronate, icatibant, icofungipen, idarubicin, imidapril, immepip, immepyr, immucillin-H, impentamine, indeloxazine, inogatran, (+)-isamoltan, isodoxorubicin, isofagomine, janthinomycins, kahalalide F, kaitocephalin, kanamycin, ketamine, L-4-oxalysine, labetalol, labotolol, ladostigil, lagatide, landiolol, lanicemine, lanomycin, lapatinib, lazabemide, L-dopa, lenapenem, lerisetron, leurubicin, leustroducsin A, leustroducsin B, leustroducsin C, leustroducsin H, levobunolol, L-histidinol, L-homothiocitrulline, lisinopril, litoxetine, lobendazole, lobophorin A, loracarbef, lotrafiban, L-thiocitrulline, lubazodone, lysobactin, mabuterol, manzamines, maprotiline, maropitant, mebendazole, mecamylamine, mefloquine, melagatran, meluadrine, memantine, mepindolol, meropenem, mersacidin, metaproterenol, metaraminol, metazoline, methoctramine, methotrexate, methyldopa, methyldopamine, α-methylepinephrine, methylphenidate, metoclopramide, metolol, metoprolol, metyrosine, mexiletine, michellamine B, micronomicin, midafotel, midaxifylline, mideplanin, milacamide, milnacipran, mitoxantrone, moexipril, mofegiline, moxifloxacin, mureidomycins, mycestericin E, nadolol, napsamycins, nardeterol, N-desmethylmilameline, nebivolol, neboglamine, nebracetam, nepicastat, neramexane, neridronate, netamiftide, nifedipine, nimodipine, nipradilol, noberastine, nocodazole, nolomirole, (S)-noremopamil, norepinephrine, norfloxacin, nornicotine, nortopixantrone, nortriptyline, nuvanil, oberadilol, octreotide, olamufloxacin, olcegepant, olradipine, orbifloxacin, orienticins, oritavancin, oseltamivir, osutidine, ovothiol A, ovothiol B, oxfendazole, oxibendazole, oxmetidine, oxolide, 7-oxostaurosporine, oxprenolol, pafenolol, palau'amine, palindore, pamatolol, pamidronate, papuamide A, papuamide B, parbendazole, parodilol, paromomycin, paroxetine, pasireotide, pazufloxacin, pelagiomicin C, penbutalol, penbutolol, perindopril, phendioxan, phospholine, picumeterol, pindolol, p-iodorubidazone, pipedemic acid, pirbuterol, pixantrone, pluraflavin A, pluraflavin B, poststatin, practolol, pradimicin, pradimicin B, pradimicin D, pradimicin E, pradimicin FA-2, pradofloxacin, pramipexole, pranedipine, prazosin, pregabalin, premafloxacin, prenalterol, primidolol, prisotinol, prizidilol, procainamide, procaterol, propafenone, propanolol, propranolol, protriptyline, proxodolol, pseudoephedrine, pyloricidin B, pyridazomycin, quinapril, quinterenol, ralfinamide, ramipril, ramoplanins, ranitidine, rasagiline, ravidomycin, reboxetine, remacemide, repinotan, reproterol, restricticin, rhodopeptins, rilmazafone, rimiterol, rimoterol, risotilide, ritodrine, ruboxyl, sabarubicin, safinamide, safingol, salbostatin, salbutamol, salmeterol, sampatrilat, sarizotan, seglitide, seproxetine, seraspenide, sertraline, setazindol, sezolamide, sibanomicin, sibenadet, silodosin, sitafloxacin, socorromycin, solabegron, solotol, solpecainol, (+)-sotalol, soterenol, sparfloxacin, sperabillins, spinorphin, spisulosine, squalamine, styloguanidine, sulfiniolol, sulfinterol, sulictidil, sulphazocine, sulphostin, sumanirole, tabilautide, tabimorelin, tafenoquine, tageflar, talibegron, tamsulosin, targinine, tazaolol, tecalcet, telavancin, temocapril, terbutaline, tertatolol, tetrafibricin, tetrahydrazoline, tetrindol, theprubicin, thiabendazole, thiofedrine, thrazarine, tiamdipine, tiamenidine, tianeptine, tienoxolol, tigecycline, tilisolol, timolol, tinazoline, tiotidine, tipifarnib, tiprenolol, tipridil, tirofiban, tocamide, tolamolol, tolazoline, tomoxetine, topixantrone, tosufloxacin, tramazoline, trandolapril, tranexamic acid, tranylcypromine, triamterene, trovafloxacin, troxipide, tuftsin, tulathromycin B, tulobuterol, ubestatin, ulifloxacin, utibapfil, vestipitant, vicenistatin, vigabatrin, vildagliptin, viloxazine, vofopitant, voglibose, xamoterol, ximelagatran, xylometazoline, zabiciprilat, zelandopam, ziconotide, zilpaterol, and zorubicin. Amine-containing drug cargo can be tethered as amides, ureas, and carbamates as described above.

Examples of alcohol-containing drugs include, but are not limited to, abiraterone, acarbose, acetohydroxamic acid, acetophenazine, acetyldigitoxin, alprostadil, alvimopan, amcinonide, apomorphine, atazanavir, atorvastatin, atropine, azithromycin, bazedoxfiene, beclomethasone, bentiromide, benzyl alcohol, beractant, betamethasone, bimatoprost, biperiden, bromocriptine, budesonide, buprenorphine, calcifediol, calcipotriene, calcitriol, canagliflozin, capecitabine, capsaicin, captopril, carboprost, carphenazine, cefamandole, cefpiramide, cerivastatin, chenodiol, chlophedianol, chloramphenicol, chlortetracycline, ciclesonide, ciclopirox, ciclosporin, clarithromycin, clavulanate, clidinium bromide, clindamycin, clioquinol, clobetasol, clocortolone, codeine, cortisone, cromoglicic acid, cyclopentolate, cyclosporine, cycrimine, danazol, dapagliflozin, deferasirox, demeclocycline, deslanoside, desogestrel, desonide, desoximetasone, desoxycorticosterone, dexamethasone, dienestrol, diethylstilbestrol, diflorasone, diflunisal, difluprednate, digoxin, dihydrocodeine, dinoprost, dinoprostone, dipyridamole, docetaxel, dolutegravir, doxercalciferol, doxycycline, dromostanolone, dronabinol, dyphylline, edrophonium, eltrombopag, empagliflozin, entacapone, epoprostenol, ergotamine, erythromycin, estradiol, estramustine, estrogen, estrone, ethinyl estradiol, ethylestrenol, ethynodiol diacetate, etonogestrel, etoposide, everolimus, ezetimibe, fexofenadine, finasteride, floxuridine, fludrocortisone, flumetasone, flunisolide, fluocinolone acetonide, fluocinonide, fluorometholone, fluoxymesterone, fluphenazine, flurandrenolide, fluvastatin, fulvestrant, galantamine, ganirelix, glycopyrrolate, guaifenesin, halobetasol, halofantrine, haloperidol, hexocyclium, homatropine, hydrocortamate, hydrocortisone, hydromorphone, hydroquinone, 4-hydroxybutanoic acid, hydroxyprogesterone, hydroxyzine, ibutilide, idoxuridine, iloprost, indinavir, inulin, ipragliflozin, irinotecan, isosorbide, ivacaftor, ivermectin, ixabepilone, lactulose, latanoprost, levocarnitine, levonorgestrel, levorphanol, lincomycin, loperamide, lopinavir, loteprednol, lovastatin, lubiprostone, masoprocol, medroxyprogesterone, megestrol acetate, menadiol, menthol, mepenzolate, meprednisone, mequinol, mestranol, methocarbamol, methyl salicylate, methylergonovine, methylnaltrexone, methylprednisolone, methyltestosterone, metronidazole, micafungin, mifepristone, miglitol, miglustat, minocycline, misoprostol, montelukast, mycophenolate, nabilone, nalbuphine, nalmefene, naloxone, naltrexone, nandrolone, nelfinavir, norelgestromin, norethindrone, norethynodrel, norgestimate, norgestrel, olmesartan, oxandrolone, oxazepam, oxybenzone, oxybutynin, oxycodone, oxymetholone, oxyphenbutazone, oxyrnorphone, oxytetracycline, paclitaxel, paliperidone, paramethasone, paricalcitol, pentazocine, perphenazine, phenprocoumon, piperacetazine, piroxicam, pitavastatin, plicamycin, podofilox, posaconazole, pralidoxime, pravastatin, prednicarbate, prednisolone, prednisone, procyclidine, quetiapine, quinidine, quinine, quinupristin/dalfopristin, raloxifene, raltegravir, ranolazine, remogliflozin, rentiapril, retapamulin, rifampin, rifapentine, rifaximin, rimexolone, risedronate, risedronic acid, ritonavir, rnethscopolamine, rocuronium, rosuvastatin, rotigotine, saquinavir, scopolamine, simvastatin, sirolimus, SN-38, stanozolol, streptozocin, tacrolimus, tapentadol, telbivudine, temsirolimus, teniposide, testosterone, tetracycline, tiotropium, tofogliflozin, tolcapone, tolvaptan, topotecan, tramadol, travoprost, treprostinil, triamcinolone acetonide, tridihexethyl, trifluridine, trihexyphenidyl, trilostane, trospium chloride, tubocurarine, ursodiol, valrubicin, venlafaxine, vinblastine, voriconazole, and warfarin. Alcohol-containing drug cargo can be tethered as esters, carbonates, and carbamates as described above.

In some embodiments, the cargo compound comprises an antiproliferative drug moiety. In some embodiments, the antiproliferative drug is an antimetabolite or a topoisomerase inhibitor. In some embodiments, the antiproliferative drug is selected from irinotecan, topotecan, camptothecin, lamellarin D, etoposide, teniposide, doxorubicin, daunorubicin, mitoxantrone, amsacrine, capecitabine, cytarabine, floxuridine, fludarabine, gemcitabine, methotrexate, and pemetrexed.

The cargo compounds and tethered cargo moieties may also provide diagnostic functionality. A diagnostic agent used in the present invention can include any diagnostic agent known in the art, as provided, for example, in the following references: Armstrong et al., *Diagnostic Imaging*, 5$^{th}$ Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). A diagnostic agent can be detected by a variety of ways, including as an agent providing and/or enhancing a detectable signal that includes, but is not limited to, gamma-emitting, radioactive, echogenic, optical, fluorescent, absorptive, magnetic or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like.

In some embodiments, the diagnostic agents can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives having the general structure of 4,4-difluoro-4-bora-3a,4a-diaza-s-indacene, and/or conjugates and/or derivatives of any of these. Other agents that can be used include, but are not limited to, for example, fluorescein, fluorescein-polyaspartic acid conjugates, fluorescein-polyglutamic acid conjugates, fluorescein-polyarginine conjugates, indocyanine green, indocyanine-dodecaaspartic acid conjugates, indocyanine-polyaspartic acid conjugates, isosulfan blue, indole disulfonates, benzoindole disulfonate, bis(ethylcarboxymethyl)indocyanine, bis(pentylcarboxymethyl)indocyanine, polyhydroxyindole sulfonates, polyhydroxybenzoindole sulfonate, rigid heteroatomic indole sulfonate, indocyaninebispropanoic acid, indocyaninebishexanoic acid, 3,6-dicyano-2,5-[(N,N,N',N'-tetrakis(carboxymethyl)amino] pyrazine, 3,6-[(N,N,N',N'-tetrakis(2-hydroxyethyl)amino]pyrazine-2,5-dicarboxylic acid, 3,6-bis(N-azatedino)pyrazine-2,5-dicarboxylic acid, 3,6-bis(N-morpholino)pyrazine-2,5-dicarboxylic acid, 3,6-bis(N-piperazino)pyrazine-2,5-dicarboxylic acid, 3,6-bis(N-thiomorpholino)pyrazine-2,5-dicarboxylic acid, 3,6-bis(N-thiomorpholino)pyrazine-2,5-dicarboxylic acid S-oxide, 2,5-dicyano-3,6-bis(N-thiomorpholino)pyrazine S,S-dioxide, indocarbocyaninetetrasulfonate, chloroindocarbocyanine, and 3,6-diaminopyrazine-2,5-dicarboxylic acid.

One of ordinary skill in the art will appreciate that particular optical agents used can depend on the wavelength used for excitation, depth underneath skin tissue, and other factors generally well known in the art. For example, optimal absorption or excitation maxima for the optical agents can vary depending on the agent employed, but in general, the optical agents of the present invention will absorb or be excited by light in the ultraviolet (UV), visible, or infrared (IR) range of the electromagnetic spectrum. For imaging, dyes that absorb and emit in the near-IR (~700-900 nm, e.g., indocyanines) can be particular advantageous. For topical visualization using an endoscopic method, any dyes absorbing in the visible range are suitable.

In some embodiments, the diagnostic agents can include magnetic resonance (MR) and x-ray contrast agents that are generally well known in the art, including, for example, iodine-based x-ray contrast agents, superparamagnetic iron oxide (SPIO), complexes of gadolinium or manganese, and the like. (See, e.g., Armstrong et al., *Diagnostic Imaging*, 5$^{th}$ Ed., Blackwell Publishing (2004)). In some embodiments, a diagnostic agent can include a magnetic resonance (MR) imaging agent. Exemplary magnetic resonance agents include but are not limited to paramagnetic agents, superparamagnetic agents, and the like. Exemplary paramagnetic agents can include but are not limited to gadopentetic acid, gadoteric acid, gadodiamide, gadolinium, gadoteridol, mangafodipir, gadoversetamide, ferric ammonium citrate, gadobenic acid, gadobutrol, or gadoxetic acid. Superparamagnetic agents can include but are not limited to superparamagnetic iron oxide and ferristene. Examples of x-ray contrast agents include, without limitation, iopamidol, iomeprol, iohexol, iopentol, iopromide, iosimide, ioversol, iotrolan, iotasul, iodixanol, iodecimol, ioglucamide, ioglunide, iogulamide, iosarcol, ioxilan, iopamiron, metrizamide, iobitridol and iosimenol. In certain embodiments, the x-ray contrast agents can include iopamidol, iomeprol, iopromide, iohexol, iopentol, ioversol, iobitridol, iodixanol, iotrolan and iosimenol.

In some embodiments, the diagnostic agent can include chelators that bind to metal ions to be used for a variety of imaging techniques. Exemplary chelators include but are not limited to ethylenediaminetetraacetic acid (EDTA), [4-(1,4,8,11-tetraazacyclotetradec-1-yl) methyl]benzoic acid (CPTA), cyclohexanediaminetetraacetic acid (CDTA), ethylenebis(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7,10-tetraazacyclododecane-1,4,7,10-tetra (methylene phosphonic acid) (DOTP), 1,4,8,11-tetraazacyclododecane-1,4,8,11-tetraacetic acid (TETA), 1,4,7,10-tetraazacyclododecane-1,4,7,10-tetraacetic acid (DOTA), and derivatives thereof. A radioisotope can be incorporated into some of the diagnostic agents described herein and can include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{123}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{223}$Ra, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In other embodiments, the agents can include DOTA and its various analogs with $^{111}$In, $^{177}$Lu, $^{153}$Sm, $^{88/90}$Y, $^{62/64/67}$Cu, or $^{67/68}$Ga.

Cargo compounds and trigger compounds of the invention, including those described above, can be further substituted in certain instances. A compound according to Formula I may contain, for example, an optionally substituted $R^1$ group, an optionally substituted $R^2$ group, or an optionally substituted $R^3$ group. A compound according to Formula II may contain an optionally-substituted $R^4$ group or an optionally substituted $R^5$ group. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents are generally those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. In general, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and cannot be modified by substitution, in this definition, to become, e.g., a cyclohexyl group.

Suitable monovalent substituents on a substitutable carbon atom of an "optionally substituted" group are independently halogen; —(CH$_2$)$_{0-4}$R$^\alpha$; —(CH$_2$)$_{0-4}$OR$^\alpha$; —O(CH$_2$)$_{0-4}$R$^\alpha$, —O—(CH$_2$)$_{0-4}$C(O)OR$^\alpha$; —(CH$_2$)$_{0-4}$CH(OR$^\alpha$)$_2$; —(CH$_2$)$_{0-4}$SR$^\alpha$; —(CH$_2$)$_{0-4}$Ph, wherein Ph is phenyl which may be substituted with R$^\alpha$; —(CH$_2$)$_{0-4}$O(CH$_2$)$_{0-1}$phenyl, which phenyl may be substituted with R$^\alpha$; —CH═CHPh, wherein Ph is phenyl which may be substituted with R$^\alpha$; —(CH$_2$)$_{0-4}$O(CH$_2$)$_{0-1}$-Py, wherein Py is pyridyl which may be substituted with R$^\alpha$; —NO$_2$; —CN; —N$_3$; —(CH$_2$)$_{0-4}$N(R$^\alpha$)$_2$; —(CH$_2$)$_{0-4}$N(R$^\alpha$)C(O)R$^\alpha$; —N(R$^\alpha$)C(S)R$^\alpha$; —(CH$_2$)$_{0-4}$N(R$^\alpha$)C(O)NR$^\alpha$$_2$; —N(R$^\alpha$)C(S)NR$^\alpha$$_2$; —(CH$_2$)$_{0-4}$N(R$^\alpha$)C(O)OR$^\alpha$; —N(R$^\alpha$)N(R$^\alpha$)C(O)R$^\alpha$; —N(R$^\alpha$)N(R$^\alpha$)C(O)NR$^\alpha$$_2$; —N(R$^\alpha$)N(R$^\alpha$)C(O)OR$^\alpha$; —(CH$_2$)$_{0-4}$C(O)R$^\alpha$; —C(S)R$^\alpha$; —(CH$_2$)$_{0-4}$C(O)OR$^\alpha$; —(CH$_2$)$_{0-4}$C(O)SR$^\alpha$; —(CH$_2$)$_{0-4}$C(O)OSiR$^\alpha$$_3$; —(CH$_2$)$_{0-4}$OC(O)R$^\alpha$; —OC(O)(CH$_2$)$_{0-4}$SR—SC(S)SR$^\alpha$; —(CH$_2$)$_{0-4}$SC(O)R$^\alpha$; —(CH$_2$)$_{0-4}$C(O)NR$^\alpha$$_2$; —C(S)NR$^\alpha$$_2$, —C(S)SR$^\alpha$; —SC(S)SR$^\alpha$, —(CH$_2$)$_{0-4}$OC(O)NR$^\alpha$$_2$; —C(O)N(OR$^\alpha$)R$^\alpha$; —C(O)C(O)R$^\alpha$; —C(O)CH$_2$C(O)R$^\alpha$; —C(NOR$^\alpha$)R$^\alpha$; —(CH$_2$)$_{0-4}$SSR$^\alpha$; —(CH$_2$)$_{0-4}$S(O)$_2$R$^\alpha$; —(CH$_2$)$_{0-4}$S(O)$_2$OR$^\alpha$; —(CH$_2$)$_{0-4}$OS(O)$_2$R$^\alpha$; —S(O)$_2$NR$^\alpha$$_2$; —(CH$_2$)$_{0-4}$S(O)R$^\alpha$; —N(R$^\alpha$)S(O)$_2$NR$^\alpha$$_2$; —N(R$^\alpha$)S(O)$_2$R$^\alpha$; —N(OR$^\alpha$)R$^\alpha$; —C(NH)NR$^\alpha$$_2$; —P(O)$_2$R$^\alpha$; —P(O)R$^\alpha$$_2$; —OP(O)R$^\alpha$$_2$; —OP(O)(OR$^\alpha$)$_2$; SiR$^\alpha$$_3$; —(C$_{1-4}$ straight or branched)alkylene)O—N(R$^\alpha$)$_2$; or —(C$_{1-4}$ straight or branched)alkylene)C(O)O—N(R$^\alpha$)$_2$. Each R$^\alpha$ is independently hydrogen; C$_{1-6}$ alkyl; —CH$_2$Ph, —O(CH$_2$)$_{0-1}$Ph; —CH$_2$-(5- to 6-membered heteroaryl); C$_{3-8}$ cycloalkyl; C$_{6-10}$ aryl; 4- to 10-membered heterocyclyl; or 6- to 10-membered heteroaryl; and each R$^\alpha$ may be further substituted as described below.

Suitable monovalent substituents on R$^\alpha$ are independently halogen, —(CH$_2$)$_{0-2}$R$^\beta$; —(CH$_2$)$_{0-2}$OH; —(CH$_2$)$_{0-2}$OR$^\beta$; —(CH$_2$)$_{0-2}$CH(OR$^\beta$)$_2$; —CN; —N$_3$; —(CH$_2$)$_{0-2}$C(O)R$^\beta$; —(CH$_2$)$_{0-2}$C(O)OH; —(CH$_2$)$_{0-2}$C(O)OR$^\beta$; —(CH$_2$)$_{0-2}$SR$^\beta$; —(CH$_2$)$_{0-2}$SH; —(CH$_2$)$_{0-2}$NH$_2$; —(CH$_2$)$_{0-2}$NHR$^\beta$; —(CH$_2$)$_{0-2}$NR$^\beta$$_2$; —NO$_2$; SiR$^\beta$$_3$; —OSiR$^\beta$$_3$; —C(O)SR$^\beta$; —(C$_{1-4}$ straight or branched alkylene)C(O)OR$^\beta$; or —SSR$^\beta$; wherein each R$^\beta$ is independently selected from C$_{1-4}$ alkyl; —CH$_2$Ph; —O(CH$_2$)$_{0-1}$Ph; C$_{3-8}$ cycloalkyl; C$_{6-10}$ aryl; 4- to 10-membered heterocyclyl; or 6- to 10-membered heteroaryl. Suitable divalent substituents on a saturated carbon atom of R$^\alpha$ include ═O and ═S.

Suitable divalent substituents on a saturated carbon atom of an "optionally substituted" group include the following: ═O; ═S; ═NNR$^\gamma$$_2$; ═NNHC(O)R$^\gamma$; ═NNHC(O)OR$^\gamma$; ═NNHS(O)$_2$R$^\gamma$; ═NR$^\gamma$; ═NOR$^\gamma$; –O(C(R$^\gamma$$_2$))$_{2-3}$O—; or —S(C(R$^\gamma$$_2$))$_{2-3}$S—; wherein each independent occurrence of R$^\gamma$ is selected from hydrogen; C$_{1-6}$ alkyl, which may be substituted as defined below; C$_{3-8}$ cycloalkyl; C$_{6-10}$ aryl; 4- to 10-membered heterocyclyl; or 6- to 10-membered heteroaryl. Suitable divalent substituents that are bound to vicinal substitutable carbons of an "optionally substituted" group include: —O(CR$^\beta$$_2$)$_{2-3}$O—; wherein each independent occurrence of R$^\beta$ is selected from hydrogen; C$_{1-6}$ alkyl which may be substituted as defined below; C$_{3-8}$ cycloalkyl; C$_{6-10}$ aryl; 4- to 10-membered heterocyclyl; or 6- to 10-membered heteroaryl.

Suitable substituents on the alkyl group of R$^\gamma$ include halogen; —R$^\delta$; —OH; —OR$^\delta$; —CN; —C(O)OH; —C(O)OR$^\delta$; —NH$_2$; —NHR$^\delta$; —NR$^\delta$$_2$; or —NO$_2$; wherein each R$^\delta$ is independently C$_{1-4}$ alkyl; —CH$_2$Ph; —O(CH$_2$)$_{0-1}$Ph; 4- to 10-membered heterocyclyl; or 6- to 10-membered heteroaryl.

Suitable substituents on a substitutable nitrogen of an "optionally substituted" group include —R$^\epsilon$; —NR$^\epsilon$$_2$; —C(O)R$^\epsilon$; —C(O)OR$^\epsilon$; —C(O)C(O)R$^\epsilon$; —C(O)CH$_2$C(O)R$^\epsilon$; —S(O)$_2$R$^\epsilon$; —S(O)$_2$NR$^\epsilon$$_2$; —C(S)NR$^\epsilon$$_2$; —C(NH)NR$^\epsilon$$_2$; or —N(R$^\epsilon$)S(O)$_2$R$^\epsilon$; wherein each R$^\epsilon$ is independently hydrogen; C$_{1-6}$ alkyl which may be substituted as defined below; C$_{3-8}$ cycloalkyl; C$_{6-10}$ aryl; 4- to 10-membered heterocyclyl; or 6- to 10-membered heteroaryl.

Suitable substituents on the alkyl group of R$^\epsilon$ are independently halogen; —R$^\delta$; —OH; —OR$^\delta$; —CN; —C(O)OH; —C(O)OR$^\delta$; —NH$_2$; —NHR$^\delta$; —NR$^\delta$$_2$; or —NO$_2$; wherein each R$^\delta$ is independently C$_{1-4}$ alkyl; —CH$_2$Ph; —O(CH$_2$)$_{0-1}$Ph; C$_{6-10}$ aryl; 4- to 10-membered heterocyclyl; or 6- to 10-membered heteroaryl.

IV. PHARMACEUTICAL FORMULATIONS

In another aspect, the invention provides a pharmaceutical composition comprising the chemical delivery system as described herein and a pharmaceutically acceptable excipient.

The compounds can be administered orally, topically, parenterally, by inhalation or spray or rectally in dosage unit formulations. The term "administration by injection" includes intravenous, intramuscular, subcutaneous and parenteral injections, as well as use of infusion techniques. One or more compounds can be present in association with one or more non-toxic pharmaceutically acceptable carriers and if desired other active ingredients.

Parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes. The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride. More details on non-aqueous liquid formulations are disclosed below.

Solutions and dispersions of the cargo compound and/or trigger compound as a free acid or base, or as pharmacologically acceptable salt, can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Compositions intended for oral use can be prepared according to any suitable method known to the art for the manufacture of pharmaceutical compositions. Suitable oral dosage forms include tablets, capsules, solutions, suspensions, syrups, and lozenges. Such compositions can contain one or more agents selected from diluents, sweetening agents, flavoring agents, coloring agents and preserving agents in order to provide palatable preparations. Tablets can be made using compression or molding techniques well known in the art. Gelatin or non-gelatin capsules can be prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition which may include plasticizers, pigments, colorants, stabilizing agents, and glidants. Delayed release dosage formulations may be prepared as described in standard references. These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium carbonate, calcium sulfate, lactose, sucrose, mannitol, sorbitol, cellulose, microcrystalline cellulose, kaolin, sodium chloride, sodium phosphate, sodium carbonate, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrating and granulating agents are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross-linked polymers, such as cross-linked PVP (Polyplasdone® XL from GAF Chemical Corp).

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

The tablets can be uncoated or they can be coated by known techniques to delay disintegration and adsorption in the gastrointestinal tract and thereby provide a sustained action over a longer period. For example, a time delay material such as glyceryl monostearate or glyceryl distearate can be employed. These compounds can also be prepared in solid, rapidly released form.

Compositions for oral use can also be formulated as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the cargo compound and/or the trigger compound in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents can be a naturally occurring phosphatide, for example, lecithin, or condensation products or an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the compounds in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, can also be present.

The compounds can also be in the form of non-aqueous liquid formulations, e.g., oily suspensions which can be formulated by suspending the active ingredients in a vegetable oil, for example arachis oil, olive oil, sesame oil or peanut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide palatable oral preparations. These compositions can be preserved by the addition of an anti-oxidant such as ascorbic acid.

Pharmaceutical compositions of the invention can also be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol or sucrose. Such formulations can also contain a demulcent, a preservative and flavoring and coloring agents.

The compounds can also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

V. Methods of Treatment

In another aspect, the invention provides a method for treating a disease or condition. The method includes administering to a subject in need thereof an effective amount of a chemical delivery system or a pharmaceutical composition as described herein. In some embodiments, the disease or condition is selected from the group consisting of cancer, inflammation, and bacterial infection.

Cancers to be treated with the chemical delivery systems disclosed herein can be carcinomas, sarcomas, adenocarcinomas, lymphomas, leukemias, solid cancers and/or lymphoid cancers. Examples of different types of cancer include, but are not limited to, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma, head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia, and multiple myeloma.

In some embodiments, the chemical delivery system is used for the treatment of cancer. In some embodiments, the cancer is selected from lung, breast, prostate, brain, bone, bladder, cervical, gastric, oral, ovarian, testicular, liver, rectal, retinal, urethral, uterine and vaginal cancer. Chemical delivery systems for treatment of such cancer will generally include cargo moieties derived from anti-proliferative parent drugs including, but not limited to, doxorubicin, etoposide, lapatinib, methotrexate, prednisolone, vincristine, and other anti-proliferative agents described above.

In some embodiments, the chemical delivery system is used for treatment of inflammatory disorders, including but not limited to, acute inflammation, chronic inflammation, arthritis (i.e., rheumatoid arthritis and collagen-induced arthritis), inflammatory bowel disease (IBD), psoriasis, uveitis, mid-ear inflammation, and osteoarthritis. Chemical delivery systems for treatment of such inflammatory conditions will generally include cargo moieties derived from anti-inflammatory parent drugs including, but not limited to, piroxicam, dexamethasone, triamcinolone, and other anti-inflammatory agents described above.

In some embodiments, the chemical delivery system is used for treatment of an infection such as a bacterial infection, fungal infection, or viral infection. For example, the chemical delivery system can be used to treat infection by a bacterium or bacteria such as, e.g., *Staphylococcus epidermidis, Staphylococcus aureus, Pseudomonas aeruginosa, Clostridium difficile, Klebsiella pneumoniae, Enterococcus faecalis, Escherichia coli, Proteus mirabilis, Pseudomonas aeruginosa, Klebsiella pneumoniae, Enterobacter cloacae, Acinetobacter* spp., *Serratia marcescens, Enterobacter aerogenes, Stenotrophomonas maltophilia, Proteus mirabilis, Klebsiella oxytoca,* and *Citrobacter freundii*. Chemical delivery systems for treatment of such infections will generally include cargo moieties derived from antibacterial parent drugs including, but not limited to, amoxicillin, ampicillin, cefaclor, azithromycin, erythromycin, and other antibacterial agents described above.

The specific dose level selected for any particular patient will depend upon a variety of factors, including the activity of the specific compound employed, the age, body weight, general health, sex, diet, time of administration, route of administration, and rate of excretion, drug combination and the severity of the condition undergoing therapy.

Compounds in the chemical delivery system of the invention can be administered at any suitable dose in the methods of the invention. In general, the compounds in the chemical delivery system are administered at a dose ranging from about 0.1 milligrams to about 1000 milligrams per kilogram of a subject's body weight (i.e., about 0.1-1000 mg/kg). The dose of the cargo compound and/or the trigger compound can be, for example, about 0.1-1000 mg/kg, or about 1-500 mg/kg, or about 25-250 mg/kg, or about 50-100 mg/kg. The dose of the cargo compound and/or the trigger compound can be about 10-20 mg/kg, or 5-25 mg/kg, or 1-50 to 17, wherein the lactone, the thiolactone, or the lactam comprises a five-membered ring be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950 or 1000 mg/kg. The cargo compound and/or the trigger compound can be administered at a dose below about 1, below about 2 mg/kg, below about 3 mg/kg, below about 4 mg/kg, below about 5 mg/kg, below about 10 mg/kg, below about 15 mg/kg, below about 20 mg/kg, below about 25 mg/kg, below about 30 mg/kg, below about 35 mg/kg, below about 40 mg/kg, below about 45 mg/kg, below about 50 mg/kg, below about 55 mg/kg, below about 60 mg/kg, below about 65 mg/kg, below about 70 mg/kg, below about 75 mg/kg, below about 85 mg/kg, below about 90 mg/kg, below about 95 mg/kg, below about 100 mg/kg, below about 150 mg/kg, below about 200 mg/kg, below about 250 mg/kg, below about 300 mg/kg, below about 350 mg/kg, below about 400 mg/kg, below about 450 mg/kg, below about 500 mg/kg, below about 550 mg/kg, below about 600 mg/kg, below about 650 mg/kg, below about 700 mg/kg, below about 750 mg/kg, below about 800 mg/kg, below about 850 mg/kg, below about 900 mg/kg, below about 950 mg/kg, or below about 1000 mg/kg.

The dosages can be varied depending upon the needs of the patient, the particular formulation being administered, and other factors. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to administer the desired amount of the cargo moiety to the subject.

Administration of the chemical delivery system can be conducted for a period of time which will vary depending upon the nature of the particular cargo moiety, the severity of the disease or condition being treated, and the overall physical condition of the patient. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months.

Following treatment, a patient can be monitored for changes in his or her condition and for alleviation of the symptoms of the disease or condition. The dosage of the cargo compound and/or the trigger compound can either be increased in the event the patient does not respond significantly to a particular dosage level, or the dose can be decreased if an alleviation of the symptoms of the disease or condition is observed, or if the disease or condition has been ablated, or if unacceptable side effects are seen with a particular dosage.

A therapeutically effective amount of the chemical delivery system can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 168, 192, 216, or 240 hours, or the equivalent amount of days. The dosage regimen can consist of two or more different interval sets. For example, a first part of the dosage regimen can be administered to a subject multiple times daily, daily, every other day, or every third day. The dosing regimen can start with dosing the subject every other day, every third day, weekly, biweekly, or monthly. The first part of the dosing regimen can be administered, for example, for up to 30 days, such as 7, 14, 21, or 30 days. A subsequent second part of the dosing regimen with a different interval administration administered weekly, every 14 days, or monthly can optionally follow, continuing for 4 weeks up to two years or longer, such as 4, 6, 8, 12, 16, 26, 32, 40, 52, 63, 68, 78, or 104 weeks. Alternatively, if the disease or condition improves, the dosage may be maintained or kept at lower than maximum amount. If the disease or condition worsens, the first dosage regimen can be resumed until an improvement is seen, and the second dosing regimen can be implemented again. This cycle can be repeated multiple times as necessary.

VI. Examples

In general, all reagents and solvents used in the each step of the synthetic procedure of the enrichment-triggered chemical delivery compounds of the invention were of reagent grade and were purchased from Aldrich. Nuclear magnetic resonance (NMR) spectra were recorded at 400 MHz for $^1$H-NMR and 100 MHz for $^{13}$C-NMR on a Bruker Avance instrument. Chemical shifts (δ values) and coupling constants (J values) are given in ppm and hertz, respectively, using the respective solvent ($^1$H NMR, $^{13}$C NMR) as the internal reference. Column chromatography was carried out when necessary using High Performance Liquid Chromatography on a Shimadzu Prominence UFLC (column: Waters C18 3.5 μM, 4.6×100 mm). Mass spectral analyses were performed on an ABI API 3200 (ESI-Triple Quadruple) instrument. UV-Vis absorption spectra were recorded on a Shimadzu PharmaSpec UV-1700 UV-Visible spectrophotometer. Fluorescence spectra were recorded on a Shimadzu RF-5301PC fluorometer. 96-Well plates were read and recorded on a PerkinElmer 1420 multi-label counter.

Example 1

Synthesis of Tetrazine-Based Cargo Compounds for Mitochondrial Enrichment

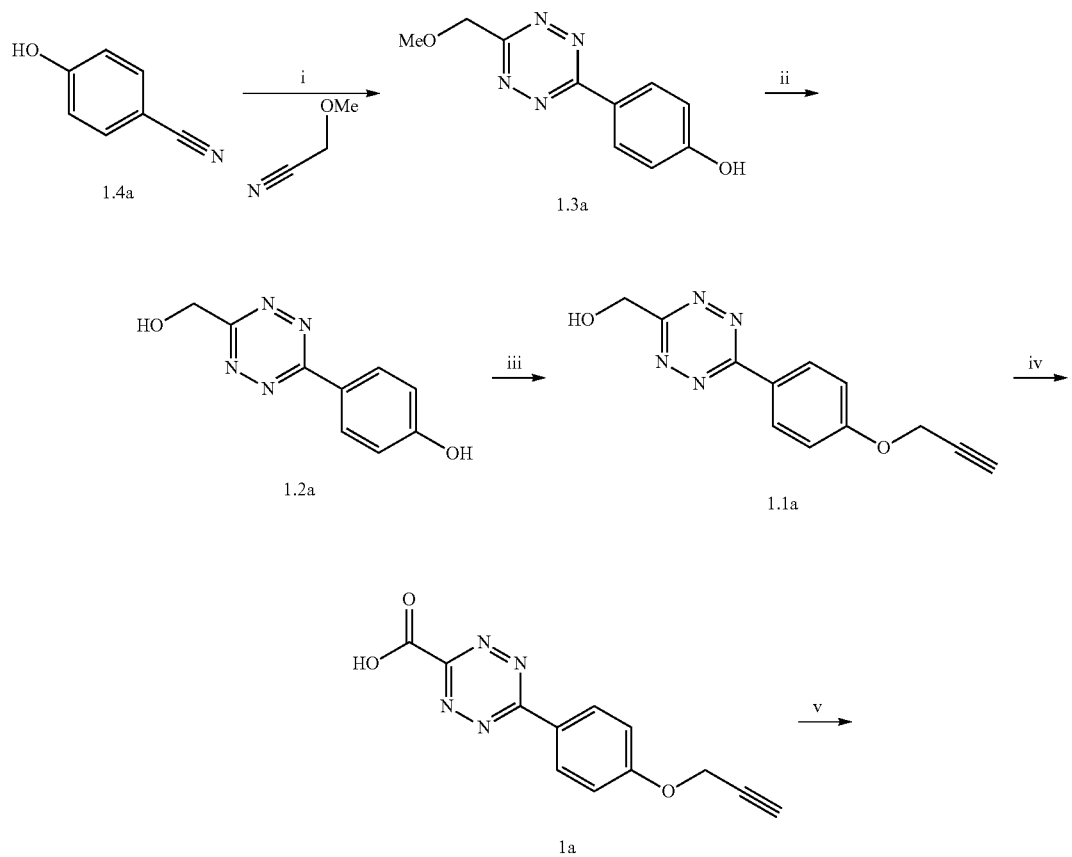

Scheme 2

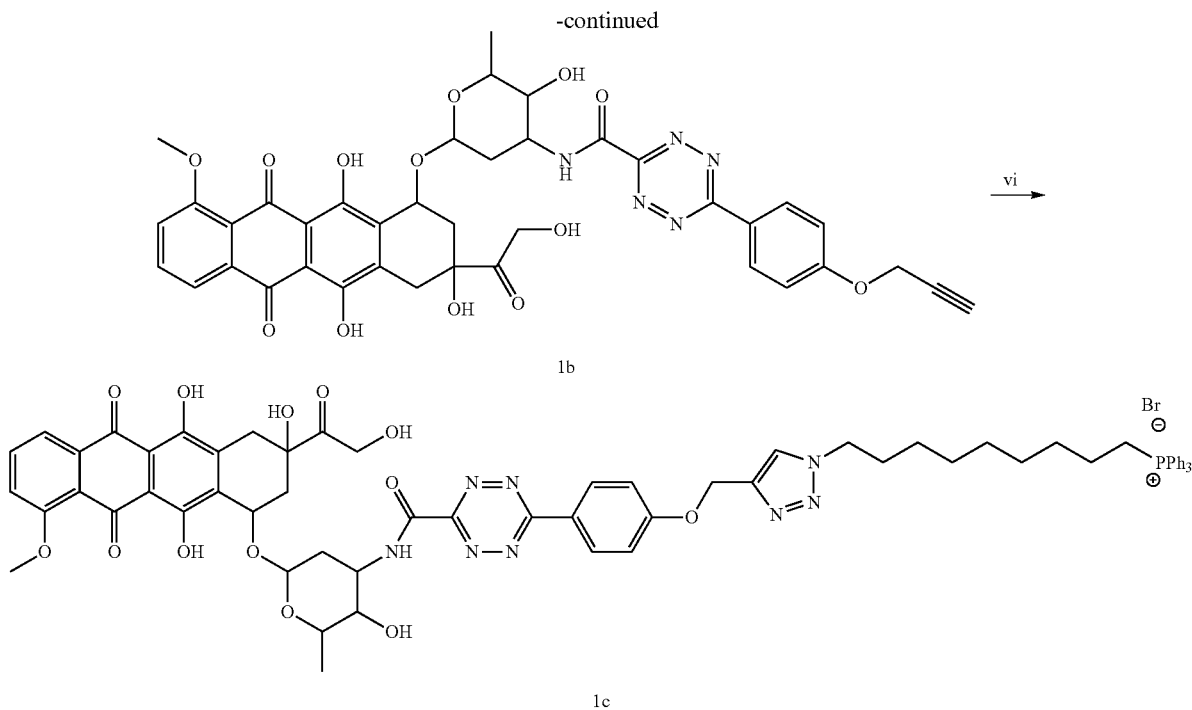

Reagents and conditions: i) N₂H₄, Zn(OTf)₂, 60° C., 24 h; then NaNO₂, H₂O, HCl; ii) dichloromethane (DCM), BBr₃, 0° C., 0.5 h; iii) propargyl bromide, acetonitrile, K₂CO₃, 60° C., 3 h; iv) DCM, Dess-Martin periodinane, r.t., 10 min; then NaClO₂/NaH₂PO₄, 2-methylbut-2-ene, t-BuOH, r.t, 2 h; v) C₂O₂Cl₂, DMF, DCM. r.t.; then NHS, Et₃N, DCM, r.t. 1 h; then Dox, Et₃N, DMF, DCM, r.t.; vi) CuSO₄·5H₂O, sodium ascorbate, DMSO, t-BuOH, N₃(CH₂)₉PPh₃Br, TBTA, 6 h, r.t.

Preparation of 4-(6-(methoxymethyl)-1,2,4,5-tetrazin-3-yl)phenol (1.3a). To a solution of 4-hydroxybenzonitrile (1.4a, 1.785 g, 15.0 mmol) and 2-methoxyacetonitrile (3.195 g, 45.0 mmol) in N₂H₄ (13.5 ml) was added Zn(OTf) (1.812 g, 6 mmol). The reaction mixture was stirred at 60° C. for 24 h and cooled down to the room temperature (r.t). Then 40 mL of ethyl acetate (EtOAc), 20 mL H₂O, and NaNO₂ (10 g, 145 mmol) were added to the mixture. HCl (10 M, 10 ml) was added slowly to the mixture over a period of 1 h. The reaction mixture was extracted with EtOAc (3×40 ml). The combined organic layer was washed with brine (50 mL), and dried over Na₂SO₄. The solvent was removed under reduced pressure to afford the crude product. The compound 1.3a was obtained as a purple solid by recrystallization with hexane and EtOAc (2.18 g, 67%). $^1$H NMR (CD₃OD): δ 8.41 (d, J=8.8 Hz, 2H), 6.96 (d, J=8.8 Hz, 2H), 4.99 (s, 2H), 3.56 (s, 3H). $^{13}$C NMR (CD₃OD): δ166.8, 166.0, 163.5, 131.1, 124.0, 117.2, 73.2, 59.6. HRMS (ESI): m/z [M+H]⁺ calcd for C₁₀H₁₁N₄O₂ 219.0882; found, 219.0898.

Preparation of 4-(6-(hydroxymethyl)-1,2,4,5-tetrazin-3-yl)phenol (1.2a). To a solution of compound 1.3a (410 mg, 1.9 mmol) in dichloromethane (DCM, 20 ml) was added BBr₃ solution (1 M, 5 ml, 5.0 mmol) dropwise. The mixture was stirred at 0° C. for 30 min, and then the reaction was quenched with water (20 ml) and extracted with EtOAc (3×30 ml). The combined organic phase was dried over Na₂SO₄ and evaporated under reduced pressure. The pure compound 1.2a was achieved by chromatography as a purple solid (230 mg, 60%). $^1$H NMR (CD₃OD): δ8.45 (d, J=8.8 Hz, 2H), 7.00 (d, J=8.8 Hz, 2H), 5.14 (s, 2H). $^{13}$C NMR (CD₃OD): δ168.8, 166.1, 163.4, 131.0, 124.2, 117.2, 63.5. HRMS (ESI): m/z [M+H]⁺ calcd for C₉H₉N₄O₂, 205.0726; found, 205.0756.

Preparation of (6-(4-(prop-2-yn-1-yloxy)phenyl)-1,2,4,5-tetrazin-3-yl)methanol (1.1a). To a solution of compound 1.2a (230 mg, 1.1 mmol) in acetonitrile (ACN) (10 ml), 3-bromoprop-1-yne (250 mg, 2.1 mmol) and K₂CO₃ (690 mg, 5.0 mmol) were added at r. t. The reaction was stirred at 60° C. for 2 h, cooled down to r.t, quenched with the HCl solution (1M, 10 ml), and then extracted with EtOAC (2×50 ml). The combined organic phase was dried over Na₂SO₄ and evaporated under reduced pressure. The pure compound 1.1a was achieved by chromatography as a purple solid (230 mg, 86%). $^1$H NMR (CD₃OD): δ 8.46 (d, J=8.8 Hz, 2H), 7.26 (d, J=8.8 Hz, 2H), 5.99 (t, J=6.4 Hz, 1H), 5.02 (d, J=6.4 Hz, 2H), 4.95 (d, J=2.4 Hz, 2H), 3.64 (t, J=2.4 Hz, 1H). $^{13}$C NMR (CD₃OD): δ168.0, 163.7, 160.8, 129.5, 124.7, 115.8, 78.8, 78.7, 62.0, 55.8. [M+H]⁺ calcd for C₁₂H₁₁N₄O₂, 243.0882; found, 243.0895.

Preparation of 6-(4-(prop-2-yn-1-yloxy)phenyl)-1,2,4,5-tetrazine-3-carboxylic acid (1a). To a solution of compound 1.1a (100 mg, 0.41 mmol) in DCM (5 ml) was added Dess-Martin periodinane (260 mg, 0.62 mmol) at r.t. After 20 min, the mixture was loaded into a silica column and eluted with DCM/EtOAC (2/1) to afford a purple solid (98 mg). The solid was dissolved in a solution of t-BuOH (3 mL) and 2-methylbut-2-ene (0.5 mL). Then a solution of NaClO₂ (74 mg, 0.82 mmol) in 0.67M NaH₂PO₄ (0.7 mL) was added slowly to the reaction mixture at r.t. After 2 h, the reaction mixture was quenched with HCl (1 M, 10 mL), and extracted with ethyl acetate (2×20 mL). The combined organic phase was dried over Na₂SO₄ and then evaporated under reduced pressure to give the crude product, which was purified by column chromatography to yield a purple solid (73 mg, 70%). $^1$H NMR (DMSO-D6): δ 8.53 (d, J=8.8 Hz, 2H), 7.29

(d, J=8.8 Hz, 2H), 4.97 (d, J=2.4 Hz, 2H), 3.63 (t, J=2.4 Hz, 1H). $^{13}$C NMR (DMSO-D6): δ 163.5, 163.2., 161.3, 160.2, 130.2, 124.6, 116.0, 78.9, 78.8, 55.9. [M+H]$^+$ calcd for $C_{12}H_9N_4O_3$, 257.0675, found; 257.0689.

Preparation of N-(3-hydroxy-2-methyl-6-43,5,12-trihydroxy-3-(2-hydroxyacetyl)-10-methoxy-6,11-dioxo-1,2,3,4,6,11-hexahydrotetracen-1-yl)oxy)tetrahydro-2H-pyran-4-yl)-6-(4-(prop-2-yn-1-yloxy)phenyl)-1,2,4,5-tetrazine-3-carboxamide (1b). To a solution of 1a (32 mg, 0.125 mmol) in 1.5 ml DCM was added oxalyl chloride (32 mg, 0.25 mmol); then DMF (2 μL) was added. The reaction was stirred at r.t. for 20 min. The solvent was removed by rotavapor. The residue was dissolved in 1 ml DCM. A solution of N-hydroxysuccinimide (NHS, 29 mg, 0.25 mmol) in 2 mL DCM was added to the reaction mixture, followed by triethylamine (Et$_3$N, 16 μL). The reaction mixture was stirred at r.t. for 1 h; then a solution of doxorubicin hydrochloride (68 mg, 0.125 mmol) in 2 mL DMF was added to the reaction mixture. Then Et$_3$N (16 μL) was added to the mixture. The reaction was stirred at r.t. for 20 min and diluted with 20 mL DCM, and washed with H$_2$O (10 mL) and brine (10 mL). The organic layer was dried over Na$_2$SO$_4$, and then evaporated under reduced pressure to give the crude compound 1b, which was purified by column chromatography to yield a red solid (50 mg, 51%). $^1$H NMR (CDCl$_3$): δ 13.97 (s, 1H), 13.21 (s, 1H), 8.56 (d, J=8.8 Hz, 2H), 8.19 (d, J=8.8 Hz, 1H), 8.00 (d, J=8.0 Hz, 1H), 7.76 (t, J=8.0 Hz, 2H), 7.36 (d, J=8.0 Hz, 2H), 7.13 (d, J=8.8 Hz, 2H), 5.57 (d, J=3.2 Hz, 1H), 5.30 (d, J=1.6 Hz, 1H), 4.80-4.79 (m, 4H), 4.54 (s, 1H), 4.52-4.48 (m, 1H), 4.27 (q, J=6.4 Hz, 1H), 4.05 (s, 3H), 3.84 (d, J=5.6 Hz, 1H), 3.26-3.28 (m 1H), 2.98-3.02 (m, 2H), 2.59 (t, J=2.4 Hz, 1H), 2.42-2.37 (m, 2H), 2.22-1.99 (m, 3H), 1.34 (d, J=9.6 Hz, 3H). $^{13}$C NMR (CDCl$_3$): δ 214.0, 187.2, 186.8, 164.9, 162.3, 161.2, 158.7, 157.4, 156.3, 155.8, 135.9, 135.6, 133.8, 133.6, 131.0, 124.1, 121.0 120.0, 118.6, 116.0, 111.8, 111.6, 100.7, 100.1, 77.7, 77.4, 76.8, 76.6, 70.0, 69.3, 67.3, 65.7, 56.8, 56.1, 46.3, 35.8, 34.1, 29.9, 17.0. [M−H]$^-$ calcd for $C_{39}H_{34}N_5O_{13}$. 780.2159; found: 780.2140.

Preparation of (7-(4-((4-(6-((3-hydroxy-2-methyl-6-((3,5,12-trihydroxy-3-(2-hydroxyacetyl)-10-methoxy-6,11-dioxo-1,2,3,4,6,11-hexahydrotetracen-1-yl)oxy)tetrahydro-2H-pyran-4-yl)carbamoyl)-1,2,4,5-tetrazin-3-yl)phenoxy)methyl)-1H-1,2,3-triazol-1-yl)heptyl)triphenylphosphonium bromide (1c). To a solution of 1b (30 mg, 0.038 mmol), (9-azidononyl)triphenylphosphonium bromide (prepared as described below, 39 mg, 0.076 mmol), tris[(1-benzyl-1H-1,2,3-triazol-4-yl)methyl]amine (TBTA, 1 mg) in t-BuOH (1.5 mL), and DMSO (0.5 mL) was added a solution of CuSO$_4$ 5H$_2$O (1 mg) and sodium ascorbate (1.5 mg) in 0.5 mL H$_2$O. The reaction mixture was stirred at r.t. for 6 h, diluted with DCM (20 mL) and H$_2$O (10 mL), and extracted with DCM (2×20 ml). The combined organic layer was washed with EDTA (20 mM, 10 mL) and brine (10 mL), dried over Na$_2$SO$_4$, and then evaporated under reduced pressure to give the crude compound 1c, which was purified by column chromatography (DCM/MeOH=9/1) to yield a red solid (28 mg, 57%). $^1$H NMR (DMSO-D$_6$): δ 14.07 (s, 1H), 13.29 (s, 1H), 8.63 (d, J=8.4 Hz, 1H), 8.48 (d, J=8.0 Hz, 2H), 8.29 (s, 1H), 7.60-7.90 (m, 18H), 7.33 (d, J=8.0 Hz, 2H), 5.57 (s, 1H), 5.25-5.30 (m, 3H), 5.20 (d, J=6.0 Hz, 1H), 4.94-5.02 (m, 1H), 4.89 (t, J=6.0 Hz, 1H), 4.61 (d, J=6.0 Hz, 2H), 4.30-4.37 (m, 3H), 3.97 (s, 3H), 3.50-3.60 (m, 2H), 2.94-3.07 (m, 2H), 2.00-2.33 (m, 4H), 1.71-1.78 (m, 4H), 1.41-1.50 (m, 4H), 1.16-1.23 (m, 11H). $^{13}$C NMR (DMSO-D6): δ 213.9, 186.5, 186.5, 163.9, 162.3, 160.8, 158.9, 158.1, 156.2, 154.6, 142.0, 136.2, 135.5, 134.9 (d, J=3.0 Hz), 134.7, 134.2, 133.6 (d, J=10 Hz), 133.4, 130.2 (d, J=12 Hz), 130.2, 124.7, 123.7, 120.0, 119.8, 118.6 (d, J=85 Hz), 115.9, 110.8, 110.7, 100.1, 75.0, 70.1, 67.8, 66.6, 63.7, 61.5, 56.6, 49.4, 46.0, 36.7, 32.1, 29.8, 29.8, 29.6, 28.5, 28.2, 27.9, 25.7, 21.6(d, J=4 Hz), 20.2 (d, J=50 Hz), 17.0. [M−Br]$^+$ calcd for $C_{66}H_{68}N_8O_{13}P$, 1211.4638; found: 1211.4692.

Preparation of (9-azidononyl)triphenylphosphonium bromide (N$_3$(CH$_2$)$_9$PPh$_3$Br). To a solution of 1,9-dibromononane (2 ml, 10 mmol) in toluene (5 ml) was added triphenylphosphine (262 mg). The reaction with stirred at 110° C. for 24 h, and then cooled down to r.t. The solvent was removed under reduce pressure, and the residue was purified by column (DCM/MeOH=50/1) to afford colorless oil (400 mg). Then the oil was dissolved in ethanol (5 ml), and followed by addition of NaN$_3$ (325 mg, 5 mmol). The reaction was stirred at 70° C. for 48 h, and cooled down to r.t. The solvent was removed under reduce pressure, and the residue was washed with H$_2$O (10 ml), and extracted with EtOAc (3×20 ml). The combined organic phase was washed with brine (10 ml) and dried over Na$_2$SO$_4$, and then evaporated under reduced pressure to give the crude product, which was purified by column chromatography (DCM/MeOH=20/1) to yield a red solid (300 mg, 62%). $^1$H NMR (CDCl$_3$): δ 7.65-7.85 (m, 15H), 3.78-3.70 (m, 2H), 3.20 (t, J=7.0 Hz, 2H), 1.46-1.58 (m, 6H), 1.13-1.25 (m, 8H). $^{13}$C NMR (CDCl$_3$): δ 135.0 (d, J=3 Hz), 133.7 (d, J=10 Hz), 130.5 (d, J=12 Hz), 118.4 (d, J=85 Hz), 51.4, 30.4 (d, J=15 Hz), 29.0, 28.9, 28.8, 26.6, 22.7, 22.6 (d, J=50 Hz) 22.6, [M−Br]$^+$ calcd for $C_{27}H_{33}N_3P$, 430.2407; found: 430.2406.

Scheme 3

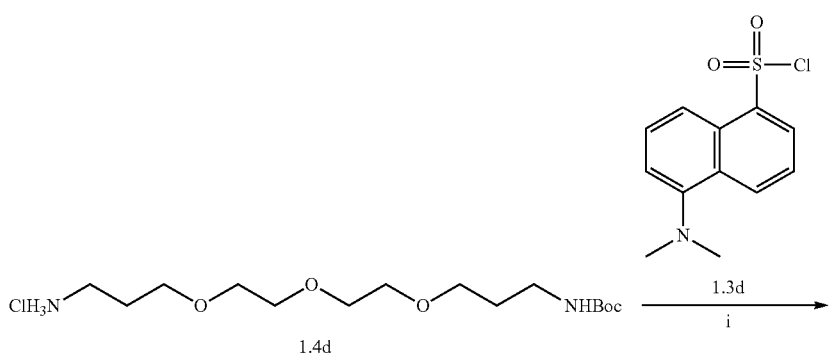

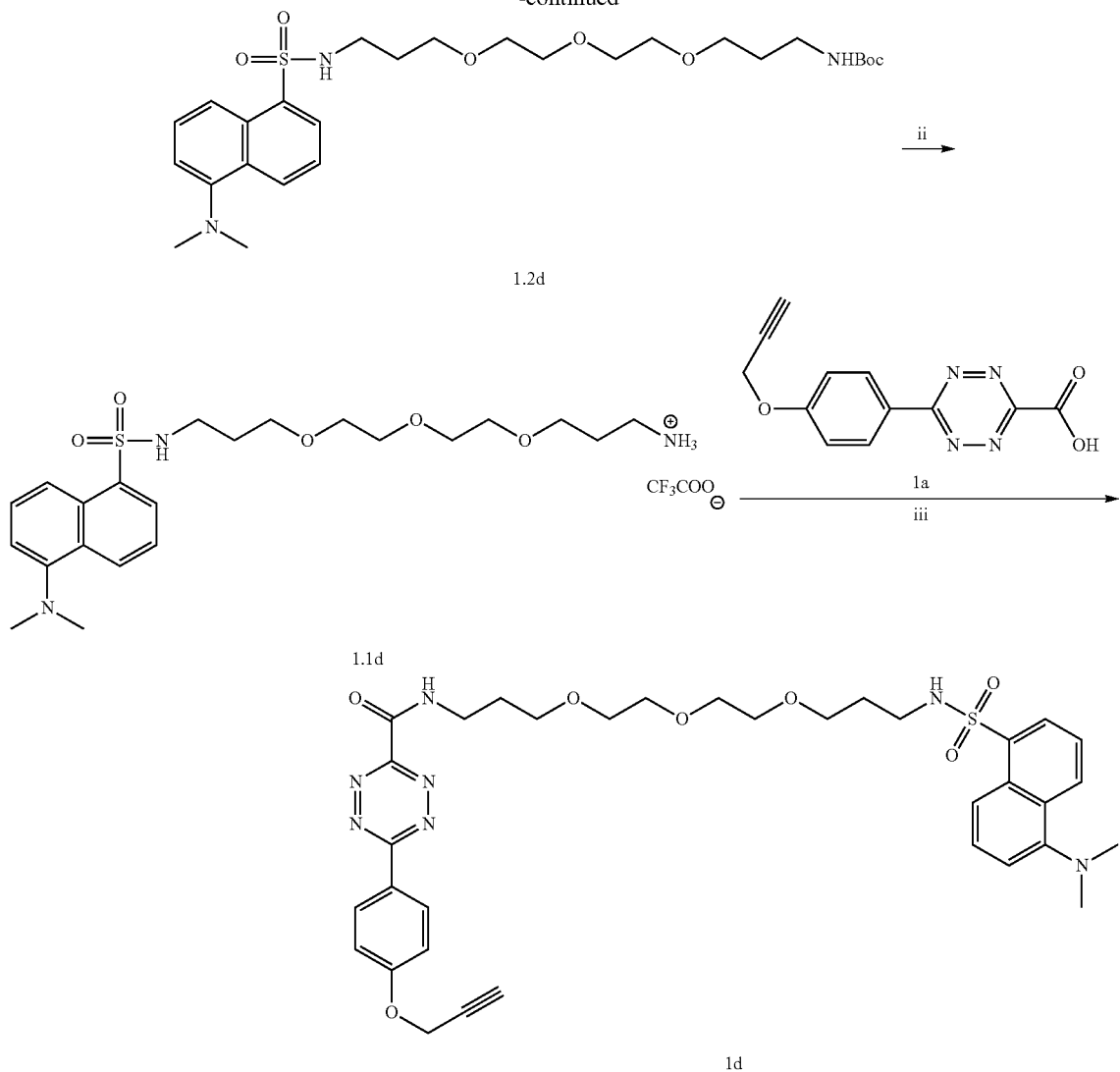

Reagents and conditions: i) DCM, Et₃N, r.t, 1 h; ii) DCM, TFA, 30 min. r.t.; iii) C₂O₂Cl₂, DMF, DCM. r.t. 30 min; then NHS, Et₃N, DCM, 1 h, r.t.; then 1a, Et₃N, DCM, r.t., 20 min.

Preparation of tert-butyl(3-(2-(2-(3-((5-(dimethylamino)naphthalene)-1-sulfonamido)propoxy)-ethoxy)ethoxy)propyl)carbamate (1.2d). To a solution of dansyl chloride (1.3d, 270 mg, 1 mmol) in DCM (2 mL) was added a solution of NH₂-PEG-NHBoc (1.4d, 352 mg, 1.1 mmol) and then Et₃N (180 uL). The reaction mixture was stirred at r.t. for 30 min and evaporated under reduced pressure to give crude compound 1.2d, which was purified by column chromatography (DCM/MeOH=50/1) to give a yellow oil (590 mg). $^1$H NMR (CDCl₃): δ 8.51 (d, J=8.4 Hz, 1H), 8.31 (d, J=8.4 Hz, 1H), 8.22 (dd, J₁=7.2 Hz, J₂=1.2 Hz, 1H), 7.50-7.54 (m, 2H), 7.16 (d, J=7.6 Hz, 1H), 5.70-5.78 (m, 1H), 4.90-4.98(m, 1H), 3.40-3.65 (m, 12H), 3.13-3.23 (m 2H), 3.02(q, J=6.4 Hz), 2.87 (s, 6H), 1.65-1.75 (m, 2H), 1.58-1.64 (m, 2H), 1.44 (s, 9H). $^{13}$C NMR (CDCl₃): δ 156.14 152.0, 135.0, 130.2, 130.0, 129.8, 129.6, 128.3, 123.3, 119.2, 115.2, 78.9, 70.7, 70.7, 70.6, 70.4, 70.2, 70.0, 45.5, 42.2, 38.6, 29.7, 28.8, 28.6. [M+H]⁺ calcd for C₂₇H₄₄N₃O₇S. 554.2894; found: 554.2890.

Preparation of N-(3-(2-(2-(3-aminopropoxy)ethoxy)ethoxy)propyl)-5-(dimethylamino)naphthalene-1-sulfonamide (1.1d). To a solution of 1.2d (300 mg) in DCM (2 mL) was added TFA (2 mL) at r.t. The reaction mixture was stirred at r.t for 30 min and then the solvent was evaporated under reduced pressure to give the crude compound 1.1d, which was purified by column chromatography (DCM/MeOH=10/1) to afford a green oil (292 mg, 95%). $^1$H NMR (CDCl₃): δ 8.51 (d, J=8.4 Hz, 1H), 8.32 (d, J=8.4 Hz, 1H), 8.21 (dd, J₁=7.2 Hz, J₂=0.8 Hz, 1H), 7.82-7.95 (m, 2H), 7.48-7.56 (m, 2H), 7.18 (d, J=7.6 Hz, 1H) 6.48-6.55 (m, 1H), 3.55-3.68 (m, 8H), 3.44-3.50 (m, 4H), 3.15-3.22 (m, 2h), 2.95-3.00 (m 2H), 2.88(s, 6H), 1.90-1.95(m, 2H), 1.62-1.69 (m, 2H). $^{13}$C NMR (CDCl₃) δ 151.6, 135.0, 130.2, 129.9, 129.8, 129.5, 128.4, 123.4, 119.5, 115.5, 70.4, 70.4, 70.0, 69.9, 69.8, 69.6, 45.6, 41.7, 40.0, 28.8, 26.4. [M+H]⁺ calcd for C₂₂H₃₆N₃O₅S 454.2370; found: 454.2359.

Preparation of N-(3-(2-(2-(3-45-(dimethylamino)naphthalene)-1-sulfonamido)propoxy)ethoxy)-ethoxy)propyl)-6-(4-(prop-2-yn-1-yloxy)phenyl)-1,2,4,5-tetrazine-3-carboxamide (1d). To a solution of 1a (16 mg, 0.0625 mmol) in 1 ml DCM was added oxalyl chloride (16 mg, 0.125 mmol)

and DMF (2 µL). The reaction was stirred at r.t for 20 min. Then the solvent was removed by rotavapor. The residue was dissolved in 1 mL DCM. A solution of NHS in 2 mL DCM was added to the reaction mixture, followed by the addition of Et$_3$N (16 µL). The reaction mixture was stirred at r.t for 1 h; then a solution of 1.1d (96 mg, 0.125 mmol) in 2 mL DCM was added, followed by the addition of Et$_3$N (32 µL). The reaction was stirred at r.t for 20 min, diluted with 20 mL DCM, and washed with H$_2$O (10 mL) and brine (10 mL). The organic layer was separated, dried over Na$_2$SO$_4$, and evaporated under reduced pressure. The residue was purified by column (DCM/MeOH=50/1) to afford compound 1d as a purple solid 25 mg (60%). $^1$H NMR (CDCl$_3$): δ 8.63 (dd, J$_1$=6.8 Hz, J$_2$=2 Hz, 2H), 8.55-8.61 (m 1H), 8.49 (d, J=8.4 Hz, 1H), 8.31 (d, J=8.4 Hz, 1H), 8.21 (dd, J$_1$=7.2 Hz, J$_2$=1.2 Hz, 1H), 7.46-7.54 (m, 2H), 7.18 (dd, J$_1$=6.8 Hz, J$_2$=2 Hz, 2H), 7.14 (d, J=7.2 Hz, 1H), 5.73-5.78 (m, 1H), 4.82 (d, J=2.4 Hz, 2H), 3.64-3.76 (m, 10H), 3.47-3.49 (m 2H), 3.40 (t, J=6.4 Hz 2H), 3.02 (q, J=6.0 Hz, 2H), 2.87 (s, 6H), 2.59 (t, J=2.4 Hz, 1H), 1.92-1.99 (m, 2H), 1.58-1.64 (m, 2H). $^{13}$C NMR (CDCl$_3$): δ 164.9, 162.2, 159.32, 157.8, 152.0, 135.1, 131.0, 130.3, 123.0, 129.8, 129.6, 128.3, 124.3, 123.3, 119.3, 116.0, 115.2, 77.4, 76.5, 70.9, 70.7, 70.6, 70.3, 70.2, 70.1, 56.1, 45.5, 42.3, 39.0, 28.9, 28.7. [M+H]$^+$ calcd for C$_{34}$H$_{42}$N$_7$O$_7$S, 692.2861; found: 692.2846.

Example 2

Synthesis of Cyclooctyne-Based Trigger Compounds for Mitochondrial Enrichment

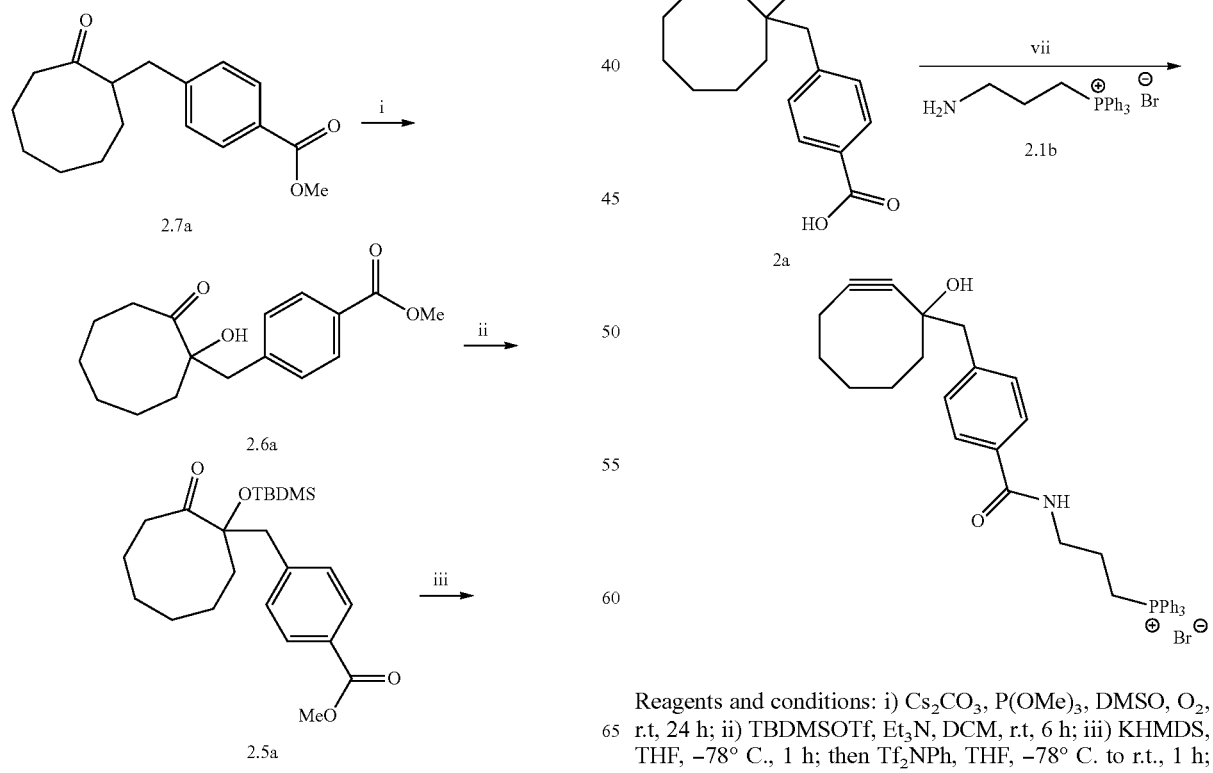

Reagents and conditions: i) Cs$_2$CO$_3$, P(OMe)$_3$, DMSO, O$_2$, r.t, 24 h; ii) TBDMSOTf, Et$_3$N, DCM, r.t, 6 h; iii) KHMDS, THF, −78° C., 1 h; then Tf$_2$NPh, THF, −78° C. to r.t., 1 h; iv) LDA, THF, 0° C., 2.5 h; v) LiOH, dioxane/H$_2$O (5:1), 60° C., 3 h; vi) TBAF, THF, r.t, 2 h; vii) EDC, NHS, DCM, r.t., 1 h; then 2.1b, DCM, Et$_3$N, r.t., 3 h.

Preparation of methyl 4-((1-hydroxy-2-oxocyclooctyl) methyl)benzoate (2.6a). The starting material, 2.7a, was obtained using known procedures as described in Agard, N. J., *ACS Chem. Biol.* 2006, 1, 644-648. To the solution of 2.7a (4.6 g, 16.8 mmol) in 20 ml of DMSO was added Cs$_2$CO$_3$ (821 mg, 2.52 mmol) and P(OMe)$_3$ (5.2 g, 42 mmol). The reaction was stirred at r.t under O$_2$ for 24 h, quenched with H$_2$O (40 mL), and extracted with EtOAc (2×200 ml). The combined organic phase was dried over Na$_2$SO$_4$ and then evaporated under reduced pressure to give the crude compound 2.6a, which was purified by column chromatography to yield a white solid (3.1 g, 64%). See Liang, Y-F, *Angew Chem Int Ed Engl* 2014, 53, 548-552 for details regarding the column chromatography procedures used to purify 2.6a. $^1$H NMR (CDCl$_3$): δ 7.91 (d, J=8.3 Hz, 2H), 7.18 (d, J=8.3 Hz, 2H), 3.88 (s, 3H), 3.84 (d, J=1.2 Hz, 1H), 2.94-2.82 (m, 3H), 2.42-2.31 (m, 1H), 2.22-2.27 (m, 1H), 2.00-1.86 (m, 2H), 1.83-1.54 (m, 4H), 1.47-1.20 (m, 2H), 0.98-0.78 (m, 1H). $^{13}$C NMR (CDCl$_3$): δ 218.1, 167.1, 140.9, 1302, 129.5, 128.9, 81.0, 52.1, 46.3, 36.8, 33.3, 30.5, 25.5, 24.5, 23.0. [M+H]$^+$ calcd for C$_{17}$H$_{23}$O$_4$, 291.1591 found: 291.1586.

Preparation of methyl 4-((1-(((tert-butyldimethylsilyl) oxy)-2-oxocyclooctyl)methyl)-benzoate (2.5a). To a solution of 2.6a (3.1 g, 10.7 mmol) in 50 ml of DCM, was added TBDMSOTf (3.4 g, 12.84 mmol) and Et$_3$N (1.3 g, 12.84 mmol). The reaction was stirred at r.t for 6 h. Then solvent was evaporated under reduced pressure to give the crude compound 2.5a, which was purified by column chromatography to yield a white solid (1.7 g, 33%). $^1$H NMR (CDCl$_3$): δ 7.91 (d, J=7.2 Hz, 2H), 7.16 (d, J=7.6 Hz, 2H), 3.90 (d, J=1.0 Hz, 3H), 3.05 (d, J=13.6 Hz, 1H), 2.90 (d, J=13.6 Hz, 1H), 2.56-2.15 (m, 3H), 1.92-1.20 (m, 8H), 1.11-1.01 (m, 1H), 0.86 (d, J=0.9 Hz, 9H), 0.05 (s, 3H), −0.12 (s, 3H). $^{13}$C NMR (CDCl$_3$): δ 216.3, 167.2, 141.6, 130.8, 129.4, 128.8, 85.1, 52.2, 47.8, 38.7, 35.9, 30.5, 26.6, 25.7, 24.8, 23.4, 19.4, −2.1, −2.4. [M+H]$^+$ calcd for C$_{23}$H$_{37}$O$_4$Si, 405.2456; found: 405.2468.

Preparation of methyl (E)-4-((1-((tert-butyldimethylsilyl) oxy)-2-(((trifluoromethyl)-sulfonyl)oxy)cyclooct-2-en-1-yl) methyl)benzoate (2.4a). To a solution of 2.5a (1.7 g, 4.2 mmol) in 50 ml of THF was added a solution of potassium bis(trimethylsilyl)amide(KHMDS) in THF (0.5 M, 9.2 ml) over a period of 10 min under the protection of argon at −78° C. The reaction was stirred at −78° C. for 1 h, and a solution of N-phenyl-bis(trifluoromethanesulfonimide) (Tf$_2$NPh, 1.6 g, 4.62 mmol) in 20 ml of THF was added slowly over 10 min. The reaction was stirred for another 10 min at −78° C., then warmed to r.t, and then stirred for another 30 min. The solvent was removed by a rotavapor and the residue was purified by chromatography to give compound 2.4a as a colorless oil (1.0 g, 47%). $^1$H NMR (CDCl$_3$): δ 7.93 (d, J=8.1 Hz, 2H), 7.22 (d, J=8.1 Hz, 2H), 5.57 (t, J=9.4 Hz, 1H), 3.91 (s, 3H), 3.36 (d, J=12.4 Hz, 1H), 2.91 (d, J=12.4 Hz, 1H), 1.69-2.01 (m, 6H), 1.53-1.32 (m, 4H), 0.96 (s, 9H), 0.27 (m, 6H). $^{13}$C NMR (CDCl$_3$) δ 167.1, 152.3, 141.6, 130.5, 129.4, 128.7, 120.5, 118. 6(q, J=317 Hz), 80.1, 52.2, 35.9, 26.5, 25.4, 23.5, 23.4, 22.1, 19.0, −1.3, −1.5. [M+H]$^+$ calcd for C$_{24}$H$_{36}$F$_3$O$_6$SSi, 537.1948; found: 537.1970.

Preparation of methyl 4-((1-((tert-butyldimethylsilyl)oxy) cyclooct-2-yn-1-yl)methyl)benzoate (2.3a). To a solution of 2.4a (450 mg, 0.84 mmol) in 10 ml of THF was added a solution of LDA in THF (2M, 0.53 ml) drop-wise over a period of 2.5 h under the protection of argon at 0° C. Then the reaction was quenched with H$_2$O (40 mL), and extracted with ethyl acetate (2×50 ml). The combined organic phase was dried over Na$_2$SO$_4$ and then evaporated under reduced pressure to give the crude compound 2.3a, which was purified by column chromatography to yield a colorless oil (200 mg, 62%). $^1$H NMR (CDCl$_3$): δ 7.93 (d, J=8.0 Hz, 2H), 7.37 (d, J=8.0 Hz, 2H), 3.89 (s. 3H), 2.97 (d, J=13.0 Hz, 1H), 2.78 (d, J=13.0 Hz, 1H), 1.36-2.32 (m, 10H), 0.83 (s, 9H), 0.12 (s, 3H), −0.26 (s, 3H). $^{13}$C NMR (CDCl$_3$): δ 167.6, 143.6, 131.2, 129.0, 128.3, 99.5, 94.9, 75.9, 52.1, 52.0, 48.3, 34.5, 30.1, 27.2, 26.1, 20.7, 18.3, −2.7, −3.6. [M+H]$^+$ calcd C$_{23}$H$_{35}$O$_3$Si 387.2350; found: 387.2365.

Preparation of 4-((1-(((tert-butyldimethylsilyl)oxy)cyclooct-2-yn-1-yl)methyl)benzoic acid (2.2a). To a solution of 2.3a (100 mg, 0.26 mmol) in dioxane (3 mL) and H$_2$O (0.75 mL) was added finely crushed LiOH (200 mg, 8.3 mmol). The suspension was heated to 50° C. and then stirred for 3 h. The dioxane was removed on a rotary evaporator and the reaction mixture was diluted with DCM (20 mL). The organic layer was washed with 1 N HCl (2×10 mL), H$_2$O (3×10 mL), and brine (1×10 mL), and dried over Na$_2$SO$_4$, yielding compound 2.2a as a white solid (86 mg 89%). $^1$H NMR (CDCl$_3$): δ 8.02 (d, J=8.0 Hz, 2H), 7.42 (d, J=8.0 Hz, 2H), 3.00 (d, J=13 Hz, 1H), 2.82 (d, J=13 Hz, 1H), 2.05-2.28 (m, 2H), 1.51-2.01 (m, 6H), 1.26-1.50 (m, 2H), 0.84 (s, 9H), 0.13 (s, 3H), −0.25 (s, 3H). $^{13}$C NMR (CDCl$_3$): δ 172.4, 144.6, 131.3, 129.6, 127.4, 99.6, 94.6, 75.7, 52.1, 48.4, 34.5, 30.1, 27.2, 26.0, 20.7, 18.2, −2.7, −3.6. [M+H]$^+$ calcd C$_{22}$H$_{33}$O$_3$Si 373.2193; found: 373.2204.

Preparation of 4-((1-hydroxycyclooct-2-yn-1-yl)methyl) benzoic acid (2a). To a solution of 2.2a (68 mg, 0.18 mmol) in 0.2 ml of THF was added tetra-n-butylammonium fluoride (TBAF) solution (2M in THF/hexane, 1 mL). The reaction was stirred at r.t for 2 h, and then the solvent was removed under reduced pressure. The residue was purified by chromatography (DCM/EtOAc=2/1) to give compound 2a as a white sticky solid (46 mg, 99%). $^1$H NMR (CDCl$_3$): δ 8.03 (d, J=8.0 Hz, 2H), 7.44 (d, J=8.0 Hz, 2H), 3.01 (d, J=13 Hz, 1H), 2.88 (d, J=13 Hz, 1H), 2.08-2.21(m, 3H), 1.72-2.03 (m, 6H), 1.36-1.44 (m, 1H). $^{13}$C NMR (CDCl$_3$): δ 172.0, 143.6, 130.7, 130.1, 127.9, 100.5, 94.4, 74.4, 50.7, 46.9, 34.5, 29.9, 26.5, 20.7. [M+H]$^+$ calcd C$_{16}$H$_{19}$O$_3$ 259.1329; found: 259.1325.

Preparation of (3-(4-((1-hydroxycyclooct-2-yn-1-yl) methyl)benzamido)propyl)-triphenylphosphonium bromide (2b). To a solution of 3a (38 mg, 0.15 mmol) in DCM, was added N-(3-dimethylaminopropyl)-N-ethylcarbodiimide hydrochloride (EDC 42 mg, 0.225 mmol) and NHS (35 mg, 0.3 mmol). The reaction was stirred at r.t for 1 h, diluted with DCM (10 mL), and then washed with H$_2$O (5 mL) and brine (5 mL). The organic phase was dried over Na$_2$SO$_4$, and evaporated under reduced pressure to afford a white solid. The solid was dissolved in 2 mL DCM, followed by the addition of a solution of 2.1b (90 mg, 0.225 mmol) in 2 mL DCM. Then Et$_3$N (30 mg, 0.3 mmol) was added into the reaction mixture. The reaction was stirred at r.t for 3 h, and diluted with DCM (15 mL). The organic layer was washed with H$_2$O (5 mL) and brine (5 mL), dried over Na$_2$SO$_4$, and evaporated under reduced pressure to afford crude compound 2b, which was purified by chromatography (DCM/ MeOH=10/1) to give a white solid (57 mg, 60%). $^1$H NMR (CDCl$_3$): δ 9.43 (t, J=6.0 Hz, 1H), 8.14 (d, J=8.0 Hz, 2H) 7.69-7.74 (m, 9H), 7.56-7.61 (m, 6H), 7.39 (d, J=8.0 Hz, 2H), 3.89-3.82 (m, 2H), 3.71-3.70 (m, 2H), 2.97 (d, J=13 Hz, 1H), 2.82 (d, J=13 Hz, 1H), 2.16 (t, J=6.0 Hz, 2H), 2.12-1.67 (m, 10H), 1.43-1.38 (m, 1H). $^{13}$C NMR (CDCl$_3$): δ 167.8, 140.6, 135.1 (d, J=3 Hz), 133.5 (d, J=10 Hz), 132.4, 130.6, 130.6 (d, J=12 Hz), 127.9, 118.4 (d, J=85 Hz), 100.1, 99.7, 94.9, 74.3, 50.8, 46.9, 39.4 (d, J=17 Hz), 34.6, 30.0, 26.7, 22.6 (d, J=4 Hz), 20.7, 20.6 (d, J=52 Hz). [M+H]+ calcd: C37H39NO2P, 560.2713 found: 560.2717. Compound 2.1b was obtained using known procedures as described in Zhou, P., *ACS Chem Biol* 2016, 11, 1098-1105.

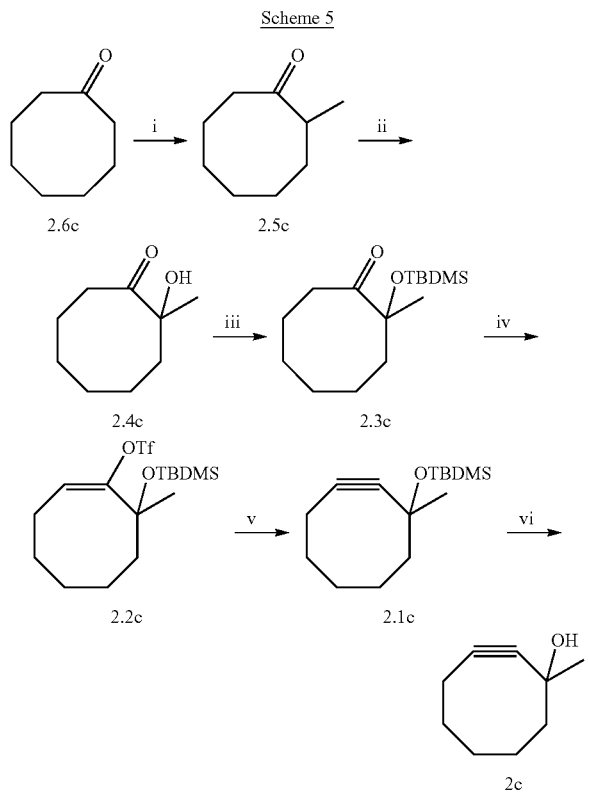

Scheme 5

Reagents and conditions: i) LDA, THF, −78° C., 1h; then methyliodide, THF, r.t, 40 min; ii) Cs2CO3, P(OEt)3, DMSO, O2 (1.0 atm), r.t, 36 h; iii) TBDMSOTf, Et3N, DCM, r.t, 6 h; iv) KHMDS, THF, 46° C., 1 h; then Tf2NPh, THF, r.t, 1 h; v) LDA, THF, 0° C., 2.5 h, 89%; vi) TBAF, THF, r.t, 2 h.

Preparation of 2-methylcyclooctan-1-one (2.5c). To a solution of commercially available cyclooctanone (2.6c, 3.2 g, 25.3 mmol) in 50 ml of THF, a solution of LDA in THF (2M, 15.1 mL) was added dropwise under the protection of argon at −78° C. The reaction was stirred at −78° C. for 1 h, and then methyliodide (1.6 ml, 25.7 mmol) was added slowly over 10 min. The reaction was stirred for another 30 min after being warmed to r.t. The solvent was removed on a rotavapor, and the residue was purified by chromatography to give compound 2.5c as a colorless oil (1.9 g, 56%). 1H NMR (CDCl3): δ2.63-2.52 (m, 1H), 2.43-2.30 (m, 2H), 1.33-1.95 (m, 9H), 1.25-1.12 (m, 1H), 1.01 (d, J=6.8 Hz, 3H). 13C NMR (CDCl3): δ 220.4, 45.3, 40.4, 33.1, 26.9, 26.6, 25.7, 24.6, 16.6. [M+H]+ calcd: C9H17O 141.1274; found: 141.1286

Preparation of 2-hydroxy-2-methylcyclooctan-1-one (2.4c). The mixture of 2.5c (1.9 g, 13.5 mmol), Cs2CO3 (1.3 g, 4.0 mmol) and P(OEt)3 (6.9 ml, 40.5 mmol) in 20 ml of DMSO was stirred at r.t under O2 for 36 h. Then the reaction was quenched with H2O (40 mL), and extracted with EtOAc (2×200 ml). The combined organic phase was dried over Na2SO4 and then evaporated under reduced pressure to give crude compound 2.4c, which was purified by column chromatography to yield a colorless liquid (0.75 g, 35%). 1H NMR (CDCl3): δ 3.91 (s, 1H), 2.83-2.72 (m, 1H), 2.35-2.24 (m, 2H), 1.99-1.83 (m, 2H), 1.82-1.67 (m, 3H), 1.67-1.56 (m, 1H), 1.39-1.28 (m, 2H), 1.27 (s, 3H), 0.96-0.83 (m, 1H). 13C NMR (CDCl3): δ 219.8, 77.8, 35.8, 34.4, 30.3, 27.4, 25.4, 24.3, 23.1. [M+Na]+ calcd: C9H16NaO2, 179.1048 found:179.1055.

Preparation of 2-((tert-butyldimethylsilyl)oxy)-2-methyl-cyclooctan-1-one (2.3c). To a solution of 2.4c (0.75 g, 4.8 mmol) in 50 ml of DCM were added TBDMSOTf (1.6 ml, 7.2 mmol) and Et3N (0.73 ml, 5.3 mmol). The reaction was stirred at r.t for 6 h before solvent evaporation under reduced pressure to give crude compound 2.3c, which was purified by column chromatography to yield a white solid (0.42 g, 33%). 1H NMR (CDCl3): δ 2.71-2.61 (m, 1H), 2.44-2.35 (m, 1H), 2.08-1.99 (m, 1H), 1.96-1.78 (m, 3H), 1.77-1.54 (m, 1H), 1.53-1.37 (m, 2H), 1.37-1.29 (m, 5H), 0.90 (s, 9H), 0.14 (d, J=6.7 Hz, 6H). 13C NMR (CDCl3): δ 217.4, 80.8, 38.6, 36.9, 29.3, 26.2, 25.9, 25.6, 24.6, 23.1, 18.5, −2.3, −2.6. [M+Na]+ calcd: C15H30NaO2Si, 293.1913 found: 293.1913.

Preparation of (E)-8-((tert-butyldimethylsilyl)oxy)-8-methylcycloct-1-en-1-yl trifluoromethanesulfonate (2.2c). To a solution of 2.3c (0.42 g, 1.58 mmol) in 50 ml of THF was added a solution of KHMDS in THF (0.5 M, 3.4 mL) slowly over 10 min under the protection of argon at −78° C. After the reaction was stirred at −78° C. for 1 h, a solution of Tf2NPh, (0.62 g, 1.73 mmol) in 10 ml of THF was added slowly over 10 min. The reaction was stirred for another 1 h after warming to r.t. The solvent was removed on a rotavapor and the residue was purified by column chromatography to give compound 2.2c as a colorless oil (0.32 g, 50%). 1H NMR (CDCl3): δ6.18 (dd, J=12.8, 4.7 Hz, 1H), 2.65-2.47 (m, 1H), 2.30-2.20 (m, 1H), 2.11-1.99 (m, 1H), 1.92-1.65 (m, 4H), 1.57-1.42 (m, 4H), 1.24-1.08 (m, 1H), 0.95 (s, 9H), 0.84-0.71 (m, 1H), 0.15 (d, J=6.6 Hz, 6H). 13C NMR (CDCl3): δ 155.5, 118.6 (q, J=318 Hz), 118.0, 76.6, 40.1, 28.8, 26.3, 26.2, 23.7, 23.5, 22.1, 18.7, −2.0, −2.0. [M+H]+ calcd: C16H30F3O4SSi, 403.1586; found 403.1575.

Preparation of tert-butyldimethyl((1-methylcyclooct-2-yn-1-yl)oxy)silane (2.1c). To a solution of 2.2c (0.32, 0.80 mmol) in 10 ml of THF, a solution of LDA in THF (2 M, 0.8 ml) was added drop-wise over a period of 20 minutes under the protection of argon at 0° C. After being warmed to r.t., the reaction was quenched with H2O (10 mL), and extracted with ethyl acetate (2×30 ml). The combined organic phase was dried over Na2SO4 and then evaporated under reduced pressure to give crude compound 2.1c, which was purified by column chromatography to yield a colorless oil (179 mg, 89%). 1H NMR (CDCl3): δ 2.29-2.10 (m, 2H), 2.08-1.98 (m, 1H), 1.92-1.82 (m, 3H), 1.80-1.68 (m, 2H), 1.61-1.51 (m, 2H), 1.36 (s, 3H), 0.88 (s, 9H), 0.19 (d, J=16.6 Hz, 6H). 13C NMR (CDCl3): δ97.7, 96.8, 71.9, 53.9, 34.8, 30.2, 29.6, 27.1, 25.9, 20.8, 18.1, −3.0, −3.0. [M+H]+ calcd: C15H29OSi, 253.1988, found: 253.1972.

Preparation of 1-methylcycloct-2-yn-1-ol (2c). To a solution of 2.1c (179 mg, 0.71 mmol), TBAF (1 M, 2.1 ml) was added. After stirring at r.t. for 2 h, the solvent was removed under reduced pressure and was purified by chromatography to give compound 2c as a colorless oil (51 mg, 52%). 1H NMR (CDCl3): δ2.29-2.12 (m, 2H), 2.10-2.01 (m, 1H), 1.99-1.75 (m, 5H), 1.74-1.61 (m, 2H), 1.58-1.47 (m, 1H), 1.42(s, 3H). 13C NMR (CDCl3): δ 98.3, 96.1, 70.9, 52.5, 34.7, 30.0, 28.2, 27.0, 20.7. M+H]+ calcd: C9H15O, 139.1117 found 139.1109.

Example 3

Kinetics Assays of Cycloaddition Reactions

Stock solution preparation. Each of the tetrazine prodrugs (compounds 1b, 1c, and 1d) was dissolved in DMSO to afford a 500-µM stock solution. Each of the alkynes (compounds 2a, 2b, 2c, and 2d) was dissolved in DMSO to afford a 50-mM stock solution. Doxorubicin (Dox) and dansylamino compound (DA) 1.1b were each dissolved in DMSO to afford 1-mM stock solutions.

HPLC method A.: mobile phase A (10 mM $NaH_2PO_4$ in water, pH=5.0) and mobile phase B (ACN), flow rate: 1 mL/min, running time: 30 min, the gradient elution method: 25% B from 0 to 6 min, 25% to 50% B from 6 to 8 min, 50% B from 8 to 15 min, 50% to 99% B from 15 to 20 min, 99% B from 20 to 25 min, 99% to 25% B from 25 to 30 min. Detection wavelength: 256 nm. Column: Waters C18 3.5 µM, 4.6×100 mm. Injection volume: 20 µL.

HPLC method B: mobile phase A (10 mM $NaH_2PO_4$ in water, pH=5.0) and mobile phase B (ACN), flow rate: 1 mL/min, running time: 30 min, the gradient elution method: 30% B from 0 to 6 min, 30% to 50% B from 6 to 8 min, 50% B from 8 to 15 min, 50% to 99% B from 15 to 20 min, 99% B from 20 to 25 min. 99% to 30% B from 25 to 30 min. Detection wavelength 1: 256, detection wavelength 2: 337 nm. Column: Waters C18 3.5 µM, 4.6×100 mm. Injection volume: 20 µL.

Standard curve of Dox concentration measurement. To four HPLC vials containing 0.9 mL PBS (size: 1.5 mL) were added 25, 15, 20, 10 µL Dox stock solution (1 mM) respectively. Then defined amounts DMSO (975, 985, 980, and 990 µL) were added to each vial to afford final concentration of four vials were 25, 15, 20, 10 µM in PBS (10% DMSO), respectively. The samples were analyzed with HPLC method A. Dox retention time: 4.0 min.

Standard curve for DA concentration measurement. To four HPLC vials containing 0.9 mL PBS (size: 1.5 mL) were added 25, 15, 20, 10 µL Dox stock solution (1 mM) respectively. Then defined amounts DMSO (975, 985, 980, and 990 µL) were added to each vial to afford final concentration of four vials were 25, 15, 20, 10 µM in PBS (10% DMSO), respectively. The samples were analyzed with HPLC method B. DA retention time: 5.8 min.

General procedures HPLC studies of reaction kinetics. To three 20-ml vials with 9 mL PBS were added a solution of tetrazine prodrug (500 µL, 500 µM). 350 µL, 300 µL and 250 µL DMSO were added to vial respectively, and then 150 µL, 200 µL and 250 µL of the alkyne solution (50 mM in DMSO) were added to the vials to afford final concentrations of alkyne 0.75 mM, 1 mM and 1.25 mM in PBS (10% DMSO, 25 µM prodrug) respectively. The reaction was stirred at r.t or 37° C. respectively. Every 30 min about 500 µL reaction mixtures were taken out and 20 µL of them were injected into the HPLC by the autosampler; the rest of them were poured back to the reaction mixture. (Note: In the cases of prodrugs 1d or 1b reacting with alkyne 2d at 37° C., the final concentrations of 2d in the kinetic studies were 250 µM, 300 µM and 350 µM).

TABLE 1

Retention time from the kinetic studies

| Method | Prodrugs | Alkyne | Prodrugs retention time (min) | Dox/DA retention time (min) | Intermediates retention time (min) |
|---|---|---|---|---|---|
| A | 1b | 2d | 13.7 | 3.9 | 13.9/14.5 |
|  |  | 2c | 13.7 | 3.9 | NO |
|  |  | 2a | 13.7 | 4.0 | 18.5 |
|  |  | 2b | 13.7 | 4.0 | 22.8 |
|  | 1c | 2b | 11.0 | 4.0 | 23.1 |
| B | 1d | 2d | 11.7 | 5.7 | 11.5/12.1 |
|  |  | 2c | 11.7 | 5.7 | no |
|  |  | 2b | 11.7 | 5.7 | 23.5 |

Determination of second-order rate constants. The reaction rate constant, $k_{obs}$, was calculated for each concentration of the alkyne by fitting the prodrug areas versus time using eq. 1:

$$Y = A \exp(-k_{obs} t) \qquad \text{eq. 1}$$

where Y is the prodrug area, and t is time. The pseudo-first-order rate constant, $k_{obs}$, was then plotted against the concentration of alkyne to yield the second-order rate constant using eq 2:

$$k_{obs} = k_2 [\text{Alkyne}] \qquad \text{eq. 2}$$

where $k_2$ is the second-order rate constant. The results are shown in Table 2.

TABLE 2

$K_{obs}$ from the kinetic studies.

| Temp. | Prodrugs (25 µM) | Alkyne | Concentration of Alkyne (mM) | Expt. 1 $K_{obs}$ (h$^{-1}$) | Expt. 2 | Expt. 3 |
|---|---|---|---|---|---|---|
| r.t | 1d | 2d | 0.75 | 0.752 | 0.704 | 0.756 |
|  |  | 2d | 1.00 | 0.980 | 0.802 | 1.01 |
|  |  | 2d | 1.25 | 1.20 | 1.10 | 1.26 |
| 37° C. | 1d | 2d | 0.25 | 1.82 | 1.64 | 1.90 |
|  |  | 2d | 0.3 | 2.15 | 1.94 | 2.26 |
|  |  | 2d | 0.35 | 2.53 | 2.25 | 2.65 |
| r.t | 1d | 2c | 0.75 | 0.0203 | 0.0201 | 0.0217 |
|  |  | 2c | 1.00 | 0.0273 | 0.0269 | 0.0289 |
|  |  | 2c | 1.25 | 0.0339 | 0.0324 | 0.0359 |
| 37° C. | 1d | 2c | 0.75 | 0.0506 | 0.0584 | 0.0599 |
|  |  | 2c | 1.00 | 0.0670 | 0.0781 | 0.0801 |
|  |  | 2c | 1.25 | 0.083 | 0.0978 | 0.101 |
| r.t | 1d | 2b | 0.75 | 0.125 | 0.115 | 0.13 |
|  |  | 2b | 1.00 | 0.155 | 0.148 | 0.175 |
|  |  | 2b | 1.25 | 0.199 | 0.180 | 0.22 |
| 37° C. | 1d | 2b | 0.75 | 0.411 | 0.388 | 0.353 |
|  |  | 2b | 1.00 | 0.548 | 0.511 | 0.453 |
|  |  | 2b | 1.25 | 0.695 | 0.636 | 0.561 |

TABLE 2-continued $K_{obs}$ from the kinetic studies.

| Temp. | Prodrugs (25 μM) | Alkyne | Concentration of Alkyne (mM) | Expt. 1 $K_{obs}$ ($h^{-1}$) | Expt. 2 | Expt. 3 |
|---|---|---|---|---|---|---|
| r.t | 1b | 2d | 0.75 | 0.894 | 0.976 | 0.993 |
|  |  | 2d | 1.00 | 1.18 | 1.30 | 1.34 |
|  |  | 2d | 1.25 | 1.47 | 1.62 | 1.69 |
| 37° C. | 1b | 2d | 0.25 | 1.90 | 1.81 | 1.97 |
|  |  | 2d | 0.3 | 2.28 | 2.15 | 2.38 |
|  |  | 2d | 0.35 | 2.65 | 2.48 | 2.78 |
| r.t | 1b | 2c | 0.75 | 0.0202 | 0.0209 | 0.0207 |
|  |  | 2c | 1.00 | 0.0282 | 0.0262 | 0.0278 |
|  |  | 2c | 1.25 | 0.0353 | 0.0341 | 0.0344 |
| 37° C. | 1b | 2c | 0.75 | 0.0607 | 0.0671 | 0.0696 |
|  |  | 2c | 1.00 | 0.0798 | 0.0895 | 0.0941 |
|  |  | 2c | 1.25 | 0.0986 | 0.112 | 0.119 |
| r.t | 1b | 2b | 0.75 | 0.201 | 0.195 | 0.197 |
|  |  | 2b | 1.00 | 0.261 | 0.257 | 0.261 |
|  |  | 2b | 1.25 | 0.309 | 0.318 | 0.326 |
| 37° C. | 1b | 2b | 0.75 | 0.486 | 0.503 | 0.533 |
|  |  | 2b | 1.00 | 0.635 | 0.672 | 0.622 |
|  |  | 2b | 1.25 | 0.783 | 0.846 | 0.905 |
| r.t | 1b | 2a | 0.75 | 0.183 | 0.191 | 0.185 |
|  |  | 2a | 1.00 | 0.235 | 0.246 | 0.247 |
|  |  | 2a | 1.25 | 0.289 | 0.295 | 0.307 |
| 37° C. | 1b | 2a | 0.75 | 0.418 | 0.438 | 0.495 |
|  |  | 2a | 1.00 | 0.546 | 0.598 | 0.678 |
|  |  | 2a | 1.25 | 0.673 | 0.739 | 0.857 |
| r.t | 1c | 2b | 0.75 | 0.296 | 0.305 | 0.291 |
|  |  | 2b | 1.00 | 0.331 | 0.356 | 0.359 |
|  |  | 2b | 1.25 | 0.445 | 0.465 | 0.474 |
| 37° C. | 1c | 2b | 0.75 | 0.711 | 0.701 | 0.714 |
|  |  | 2b | 1.00 | 0.921 | 0.902 | 0.871 |
|  |  | 2b | 1.25 | 1.21 | 1.15 | 1.09 |

General procedure for the determination of the lactonization rate constants. To a 9 mL PBS in a 20-mL vial was added a solution of the respective tetrazine prodrug (500 μL, 500 μM). Then 1 mL of the respective alkyne (50 mM in DMSO) was added to afford a final concentration of 5 mM in PBS (15% DMSO). The reaction was stirred at r.t. Every 30 min about 500 μL the reaction mixture was taken out and 20 μL of them was injected into the HPLC by an autosampler; the rest of them was poured back to the reaction mixture. The reaction rate constant, $k_1$, was determined by fitting the area in HPLC chromatogram of the intermediate versus time using eq. 3:

$$Y = A\ \exp(-k_1 t) \qquad \text{eq. 3}$$

where Y is the intermediate areas, and t is the time.

TABLE 3

Lactonization rate constants.

| Tetrazines prodrugs | Alkyne | First Data point time* | $k_1$ ($h^{-1}$) Expt 1 | Exp 2 | Expt. 3 |
|---|---|---|---|---|---|
| 1d | 2d | 1 h | 0.0253 | 0.0291 | 0.0332 |
| 1d | 2b | 4 h | 0.162 | 0.184 | 0.142 |
| 1b | 2b | 4 h | 0.223 | 0.179 | 0.196 |
| 1b | 2a | 4 h | 0.185 | 0.206 | 0.229 |
| 1c | 2b | 4 h | 0.225 | 0.191 | 0.265 |

*The time point that more that 90% prodrug were consumed.

Results. The results from the reaction kinetics studies of the tetrazine-cyclooctyne system are summarized below in Table 4. Prodrugs 1d or 1b (25 μM) were treated with alkynes 2d, 2c, 2a, or 2b at different concentrations at room temperature (r.t.) or 37° C., respectively. The prodrug consumption and release of the parent drug were monitored by HPLC (Table 4).

TABLE 4

Evaluation of the reaction kinetics of the CCR system.

| Tetrazine | Alkyne | $k_2$ at r.t ($M^{-1}s^{-1}$) | $k_2$ at 37° C. ($M^{-1}s^{-1}$) | $k_1$ at r.t ($h^{-1}$) | Dox Peak % within 48 h, at r.t (%) |
|---|---|---|---|---|---|
| 1d | 2d | 0.25 ± 0.06 | 1.9 ± 0.4 | 0.029 ± 0.006 | 60 ± 6 (48 h) |
|  | 2c | 0.0075 ± 0.0009 | 0.021 ± 0.005 | * | 90 ± 5 (20 h) |
|  | 2b | 0.042 ± 0.012 | 0.14 ± 0.04 | 0.16 ± 0.04 | 90 ± 3 (16 h) |
| 1b | 2d | 0.36 ± 0.07 | 2.1 ± 0.4 | A | 20 ± 5 (48 h) |
|  | 2c | 0.0078 ± 0.0009 | 0.025 ± 0.006 | * | 85 ± 5 (21 h) |
|  | 2b | 0.065 ± 0.013 | 0.19 ± 0.04 | 0.20 ± 0.04 | 80 ± 5 (18 h) |
|  | 2a | 0.061 ± 0.013 | 0.17 ± 0.05 | 0.21 ± 0.04 | 80 ± 5 (19h) |
| 1c | 2b | 0.091 ± 0.013 | 0.25 ± 0.05 | 0.22 ± 0.05 | 78 ± 6 (18 h) |

All reactions were conducted in PBS containing 10% DMSO.
*not detectable because of the slow second order reaction and fast lactonization reaction. No intermediates were observed.
A: not detectable because of Dox decomposition in PBS.
(n = 3, p = 0.95).

As shown in Scheme 6, the cycloaddition reaction between the cyclooctyne compound (2a, 2b, 2c or 2d) and the tetrazine compound (1a, 1b, 1c, or 1d) yields two possible regioisomeric products (7a and 7b). However, only regioisomeric compound 7b proceeds to lactonization and drug release. Results from the HPLC reaction studies showed that more than 80% Dox or dansyl amine was released within 48 h of treating the tetrazine-prodrug compounds with alkyne 2c, 2a, or 2b (See, Table 4). Such results indicate that the regiochemistry of the Inverse Electron Demand Diels-Alder reaction ($DA_{inv}$) is such that it favors the reaction leading to 7b with the hydroxyl group on the cyclooctyne positioned on the same side of the amide group linked to the parent drug. This allows for subsequent lactonization and drug release.

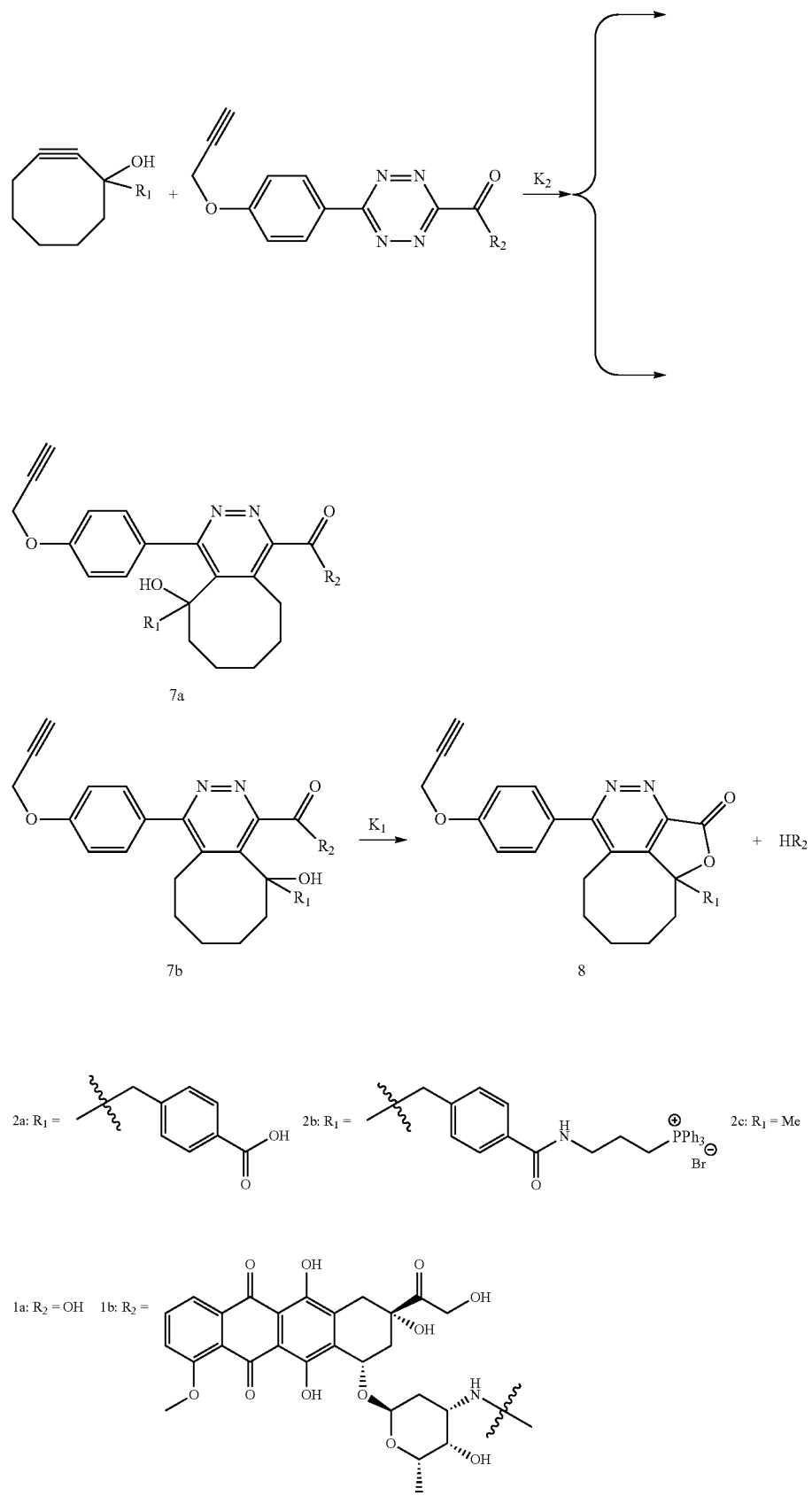

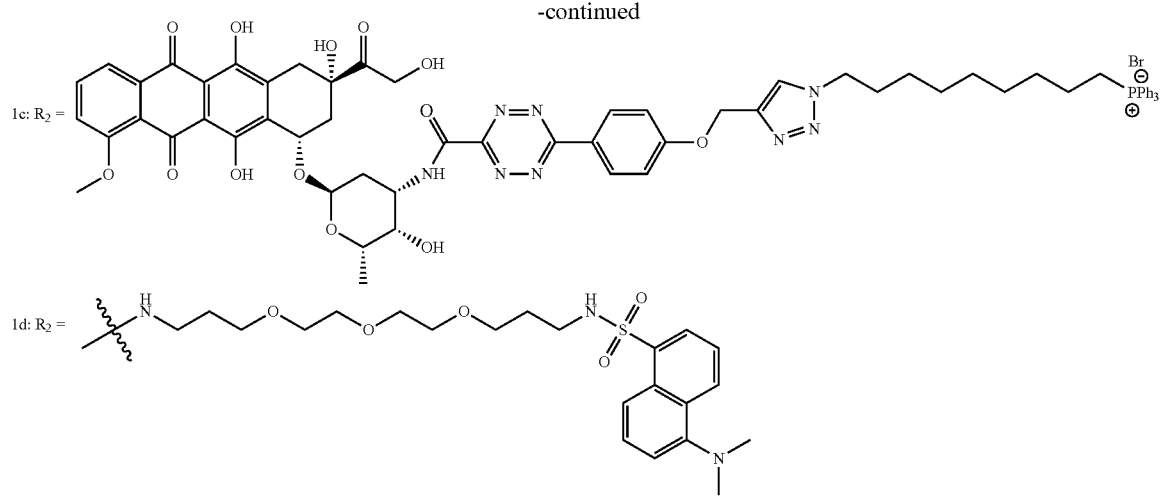

Figure 2:
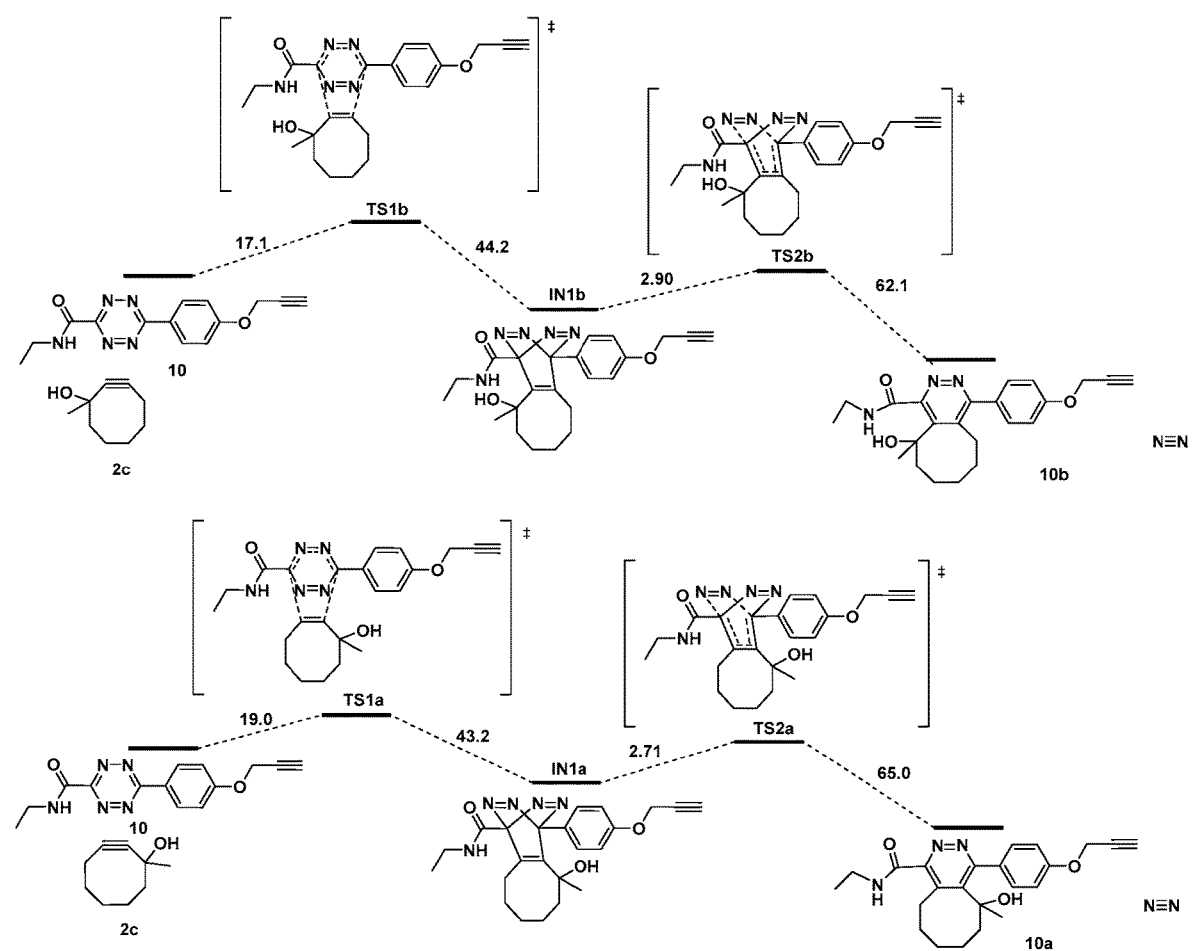
FIG. 2 shows the theoretical transition states of the reaction between model tetrazine compound 10 and cyclooctyne compound 2c. Activation energies and transition state energies are in kcal·mol$^{-1}$.

To acquire initial insight into the observed regiochemistry, theoretical calculations of possible transition state(s) and activation energies for two regioisomers were performed using reported methods. (See Chen, W. et al. *Chem Commun* 2012, 1736-1738). All calculations were performed using the Gaussian 09 program. See, Frisch, M. J., et al. Gaussian 09, Revision C.01. Wallingford, Conn., USA: Gaussian, Inc.; 2009. Initial geometry optimizations were carried out by DFT calculations with use of the B3LYP with the standard 6-31G(d,p) basis set. See, Becke A D. *J Chem Phys* 1993, 98, 5648-5652; Lee C, *Phys Rev B* 1988, 37, 785-789. The transition state geometries were obtained using the QST3 method. Schematic representations of the energy profiles for the tetrazine alkyne reactions are shown in FIG. 2. All of the QM energies are in kcal mol$^{-1}$. To simplify the calculation process, tetrazine 10 and alkyne 2c were used as models. The results showed that the activation energy for the first step of the $DA_{inv}$ between 10 and 2c via transition state TS1b is 17.1 kcal·mol$^{-1}$ as compared to 19.0 kcal·mol$^{-1}$ for the reaction via transition state TS1a. The qualitative difference in activation energy correlates well with the observed regiochemistry outcome.

Results from the CCR kinetics study indicated that the $R_1$ substituent of the cyclooctyne compounds effected the rates of both the $DA_{inv}$ reaction and the subsequent lactonization reaction. It was found that a methyl group or a benzyl group significantly reduced the rate of the $DA_{inv}$ reaction. For example, when $R_1$ was a hydrogen (i.e., compound 2d), the second order rate constant was 0.25 M$^{-1}$s$^{-1}$ at r.t and 1.9 M$^{-1}$s$^{-1}$ at 37° C. when dansyl amine-prodrug 1d was used. In comparison, the second order rate constant was 0.0075 M$^{-1}$s$^{-1}$ and 0.021 M$^{-1}$s$^{-1}$ at r.t and 37° C., respectively, for tetrazine-prodrug 1d and alkyne 2c ($R_1$=methyl); and 0.042 M$^{-1}$s$^{-1}$ and 0.14 M$^{-1}$s$^{-1}$ at r.t and 37° C., respectively, for tetrazine-prodrug 1d and alkyne 2b ($R_1$=phenyl) (See, Table 4). Such results indicate that the $DA_{inv}$ reaction rates can be tuned over a range of more than 30-fold by using different $R_1$ groups on the alkyne. Additionally, varying the temperature from r.t to 37° C. can afford another 3- to 10-fold of reaction rate variations. The reaction rate of 0.25 M$^{-1}$s$^{-1}$ between tetrazine-prodrug 1a and cyclooctyne compound 2b is similar to the reaction rate of 0.17 M$^{-1}$s$^{-1}$ between tetrazine-prodrug 1b and cyclooctyne compound 2a, indicating that the introduction of the TPP moiety did not significantly affect the reaction kinetics. It should also be noted that the $R_1$ substituent accelerated the rate of the lactonization reaction, due to added conformational constraints.

As shown in Table 4, the $R_2$ substituent of the tetrazine-prodrug compound did not cause statistically significant changes in terms of reaction rates for dansylamine-prodrug 1d or Dox-prodrug 1b. For example, the second order rate constant for the reaction of alkyne 2d with tetrazine 1d or 1b at 37° C. was 1.9 or 2.1 M$^{-1}$s$^{-1}$, respectively. Similarly, the second order rate constant for the reaction of alkyne 2b with tetrazine 1d or 1b at 37° C. was 0.14 or 0.19 M$^{-1}$s$^{-1}$, respectively. These results may be due to the "drug" moiety (i.e., $R_2$) of the tetrazine-prodrug compound being positioned away from all reaction centers. Results show that slow lactonization rates may lead to partial drug release within a reasonable period of time. This is the case with alkyne trigger 2d. For example, only 60% dansylamine (compound 1d) and 20% Dox (compound 1b) was detected after treating prodrugs with alkyne 2d (1 mM) for 48 h. The low percentage Dox recovery could be attributed to the slow lactonization rate of 7b ($t_{1/2}$=24 h) when $R_1$ was hydrogen, and decomposition of Dox in PBS ($t_{1/2}$=50 h) (Janssen, M. J. H, et al. *Int J Pharm* 1985, 23, 1-11). In contrast, the lactonization rates were too fast to detect the accumulation of an intermediate via the HPLC method after treating prodrugs 1b or 1d with alkyne 2c (Table 1), which led to 85-90% release of the active drug at the 48-h point. For alkynes 2a and 2b, the situation was similar with 80-90% drug release.

Example 4

Stability of Cargo Compounds

Due to the electron deficient nature of the tetrazine moiety, the stability of the tetrazine-linked prodrugs in the presence of high concentrations of thiol species was studied.

In general, a solution of tetrazine prodrug (500 µL, 500 µM) was added to either 9.5 mL of PBS or 1 mM cysteine solution in PBS in a 20-mL vial. The solution was stirred at r.t. or 37° C. for 24 h. The reaction solution was injected into HPLC, and analyzed with Method A (described above) for prodrugs 1b and 1c, and Method B for prodrug 1d.

Prodrug (1d or 1b, 25 µM in PBS alone or in the presence of 1 mM cysteine (Cys) in PBS was incubated at r.t or 37° C. for 24 h. Then HPLC was used to monitor the concentration of the remaining prodrug (Table 5). No stability problems were observed.

TABLE 5

Stability studies of prodrugs 1d and 1b in PBS (5% DMSO, n = 4, p =0.95).

| Prodrugs remaining | 24 h in PBS at r.t (%) | 24 h in PBS at 37° C. (%) | 24 h in PBS with 1 mM Cys at r.t (%) | 24 h in PBS with 1 mM Cys at 37° C. (%) |
|---|---|---|---|---|
| 1d | 91 ± 5 | 85 ± 5 | 88 ± 5 | 81 ± 5 |
| 1b | 85 ± 5 | 78 ± 5 | 80 ± 5 | 76 ± 5 |

Example 5

Cytotoxicity and Drug Release of Click-Cyclize-Release Delivery System

Cell cultures. HeLa cells (ATCC) were used in the following cell culture studies. HeLa cells were maintained in DMEM (Dulbecco's Modified Eagle's Medium) supplemented with 10% fetal bovine serum (MidSci; S01520HI), and 1% penicillin-streptomycin (Sigma-Aldrich; P4333) at 37° C. with 5% $CO_2$.

Cytotoxicity studies. Test compound was dissolved in DMSO to afford a stock solution. The final concentration of DMSO in the cell culture was 1% (v/v) in PBS. HeLa cells were seeded in 96-well plates one day before the experiment. Different concentrations of prodrug was added into the cell culture. The cells were then incubated for 48 h at 37° C. with 5% $CO_2$. The cell viability was tested by the MTT assay described in Levitz, S. M., et al. *J Infect Dis* 1985, 152, 938-945. Specifically, after 48 h of incubation, 5 mg/mL MTT (3-(4,5-dimethylthiazol-2-yl)-2,5-diphenyltetrazolium bromide) was added into the cell culture. After incubation for 4 h, the supernatant was removed and 100 µL DMSO was added into the wells containing the cells. After shaking gently for 3 min, absorbance at 605 nm was read by a plate reader.

Cytotoxicity studies using crystal violet assay. The test compound was dissolved in DMSO to afford a stock solution. The final concentration of DMSO in cell culture was 1% (v/v) in PBS. HeLa cells were seeded in 96-well plates one day before the experiment. Different concentrations of the test compound were added into the cell culture. The cells were then incubated for 48 h at 37° C. with 5% $CO_2$. Cell viability was tested by the crystal violet assay. Specifically, after 48 h of incubation, the cells were fixed in 100% methanol for 10 min and stained for 20 min with a 1% crystal violet solution in 50% methanol, followed by 5 repeated washings with PBS. 50 µL of DMSO was added to each well. After 20 min of incubation, the plates were analyzed in a microplate reader at 595 nm.

Results. The $IC_{50}$ values from the HeLa cell cytotoxicity studies are shown below in Table 6. The Dox-prodrug 1b lost its activity with $IC_{50}$ well over 100 µM, while the $IC_{50}$ of the parent drug Dox was about 1.0 µM. Such results show that prodrug 1b has little to no cytotoxicity prior to release of Dox through the CCR process. As designed, the $IC_{50}$ of Dox-prodrug 1b is about 1.5 µM in the presence of 50 µM alkyne 2d and 2.0 µM in the presence of 50 µM alkyne 2b. Such results indicate efficient release of the parent drug, Dox, by alkynes 2d and 2b.

TABLE 6

| $IC_{50}$ in Hela cell line (n = 3, p = 0.95) | |
|---|---|
| Compounds | $IC_{50}$ (µM) |
| Dox-prodrug 1b | >100 |
| Alkyne 2d | >100 |
| Alkyne 2b | >50 |
| Dox | 1.0 ± 0.2 |
| Dox-prodrug 1b + 50 µM 2d | 1.5 ± 0.3 |
| Dox-prodrug 1b + 100 µM 2d | 1.3 ± 0.2 |
| Dox-prodrug 1b + 50 µM 2b | 2.3 ± 0.4 |
| Tetrazine 1a + 100 µM 2d | >100 |

Figure 3A:
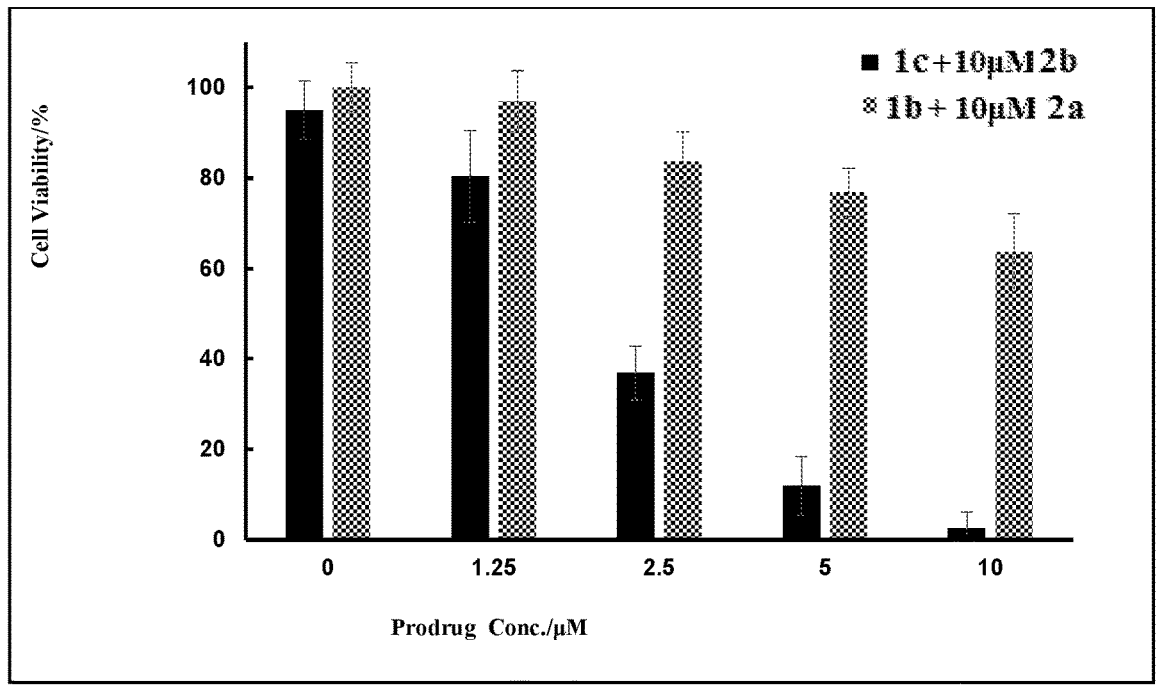
FIG. 3A shows cytotoxicity of various prodrugs with 10 µM cyclooctyne compound.
Figure 3B:
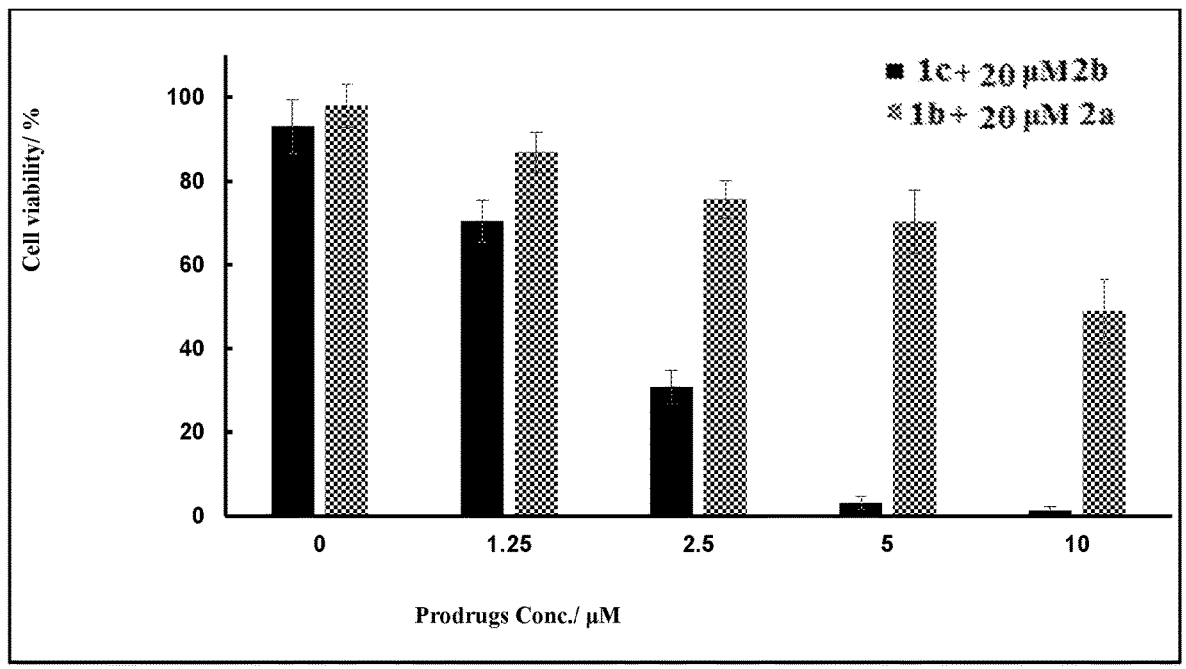
FIG. 3B shows cytotoxicity of various prodrugs with 20 µM cyclooctyne compound.

HeLa cells were treated with 10 µM or 20 µM TPP-alkyne 2b and various concentrations of TPP-Dox-prodrug 1c (0, 1.2, 2.5, 5 and 10 µM) for 48 hours. The $IC_{50}$ (~1.5 µM) for TPP-Dox 1c in the presence of 20 µM of TPP-alkyne 2b was much lower than that of the corresponding non-TPP conjugated Dox prodrug 1b (~10 µM) in the presence of 20 µM alkyne 2a (FIG. 3b). Similar results were observed when the alkyne concentration was decreased to 10 µM. For example, the $IC_{50}$ of TPP-Dox prodrug 1c was about 2 µM in the presence of 2b, while the $IC_{50}$ for Dox prodrug 1b was well over 10 µM in the presence of 10 µM of the alkyne trigger 2a (FIG. 3a). As controls, both the $IC_{50}$ values of 1c and 2b alone were higher than 40 µM, and the treatment of 20 µM of alkyne 2a or 2b alone had no effect on cell viability. Such dose-dependent results indicate that conjugation with TPP (2b and 2a) allows for enhanced release of Dox through enrichment of the prodrug in the mitochondria, subsequently leading to an enhanced bimolecular reaction rate and facilitated CCR-mediated activation of the prodrug. Without such an enrichment, the reaction is expected to be slow, resulting in a lower level of active Dox being released. Specifically, the second order rate constant of the reaction between the Dox-prodrug 1b and alkyne 2a was determined to be 0.17 $M^{-1}s^{-1}$, with the first half-life at 10 µM concentration of 1b and 10 µM concentration of 2a being about 163 h, with only 22% drug-release at 48 h. If the concentrations of both the tetrazine prodrug (1c) and alkyne (2b) were enriched to 500 µM in the mitochondria, the first half-life of the reaction would be 2.0 h (confirmed by experiments), which means almost complete Dox release at the 48-h time point. As a consequence, major differences in the apparent potency of the two prodrugs was observed with and without conjugation to TPP. Thus, mitochondrial enrichment leads to triggered release of the drug. The same concept is applicable to the delivery of drugs through other targeting approaches such as receptor-mediated drug delivery.

VII. Exemplary Embodiments

Embodiments in accordance with the present disclosure include, but are not limited to, those described in the appended claims and the following embodiments:

1. A chemical delivery system comprising:
   i) a cargo compound comprising a first reactive moiety covalently bonded to a first enrichment moiety and a tethered cargo moiety, wherein the first reactive moiety is bonded to the tethered cargo moiety via a cleavable linker; and
   ii) a trigger compound comprising a second reactive moiety covalently bonded to a second enrichment moiety and a cargo-releasing moiety;
   wherein:
   the first enrichment moiety and the second enrichment moiety cause an increase in concentration of the cargo compound and the concentration of the trigger compound at a target site;
   the first reactive moiety and the second reactive moiety are substantially unreactive toward one another without the increase in concentration of the cargo compound and the increase in concentration of the trigger compound at the target site;
   the increase in concentration of the cargo compound and the increase in concentration of the trigger compound at the target site cause a bimolecular reaction between the first reactive moiety and the second reactive moiety to form a cyclization precursor compound; and
   the cargo moiety is released from the cyclization precursor compound in a unimolecular cyclization reaction.

2. The chemical delivery system of embodiment 1, wherein the rate of the bimolecular reaction after the increase in concentration of the cargo compound and the concentration of the trigger compound at the target site is at least 2-500 times the rate of the bimolecular reaction without the increase in concentration.

3. The chemical delivery system of embodiment 2, wherein the rate of the bimolecular reaction after the increase of concentration of the cargo compound and the concentration of the trigger compound at the target site is at least 20-50 times the rate of the bimolecular reaction without the increase in concentration.

4. The chemical delivery system of embodiment 1, wherein the second order rate constant for the bimolecular reaction ranges from about $10^{-5}$ $M^{-1}s^{-1}$ to about 120 $M^{-1}s^{-1}$.

5. The chemical delivery system of embodiment 1, wherein the second order rate constant for the bimolecular reaction ranges from about $1.16 \times 10^{-5}$ $M^{-1}s^{-1}$ to about 116 $M^{-1}s^{-1}$.

6. The chemical delivery system of embodiment 1, wherein the second order rate constant for the bimolecular reaction ranges from about 0.15 $M^{-1}s^{-1}$ to about 0.35 $M^{-1}s^{-1}$.

7. The chemical delivery system of any one of embodiments 1-6, wherein the first enrichment moiety and the second enrichment moiety are independently selected mitochondrion-targeting moieties.

8. The chemical delivery system of embodiment 7, wherein the mitochondrion-targeting moiety is a positively charged phosphine.

9. The chemical delivery system of any one of embodiments 1-6, wherein the first enrichment moiety is selected from the group consisting of a folic acid moiety, a biotin moiety, an RGD peptide, a glucose moiety, an antibody, an aptamer, a prostate specific membrane antigen moiety, and a boronic acid moiety.

10. The chemical delivery system of any one of embodiments 1-6 and 9, wherein the second enrichment moiety is selected from the group consisting of a folic acid moiety, a biotin moiety, an RGD peptide, a glucose moiety, an antibody, an aptamer, a prostate specific membrane antigen moiety, and a boronic acid moiety.

11. The chemical delivery system of any one of embodiments 1-10, wherein the first reactive moiety is selected from the group consisting of a tetrazine, a thiophene 1,1-dioxide, and a cyclopentadienone.

12. The chemical delivery system of any one of embodiments 1-11, wherein the second reactive moiety is selected from the group consisting of a cyclooctyne and a cyclooctene.

13. The chemical delivery system of embodiment 1, wherein the cargo compound has a structure according to Formula I:

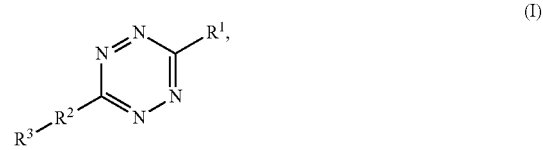

(I)

wherein $R^1$ is the first targeting moiety, $R^2$ is the cleavable linker, and $R^3$ is the tethered cargo moiety.

14. The chemical delivery system of embodiment 13, wherein the cargo compound has a structure according to Formula Ia:

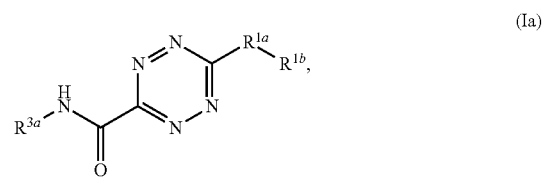

(Ia)

wherein $R^{1a}$ is a linking diradical, $R^{1b}$ is a targeting radical, and $R^{3a}$ is a cargo radical.

15. The chemical delivery system of embodiment 14, wherein the cargo compound has a structure according to Formula Ib:

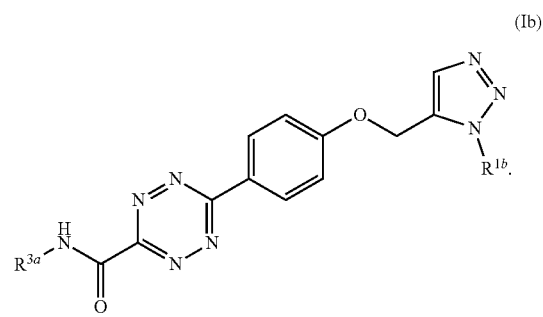

(Ib)

16. The chemical delivery system of embodiment 14 or embodiment 15, wherein the cargo compound is:

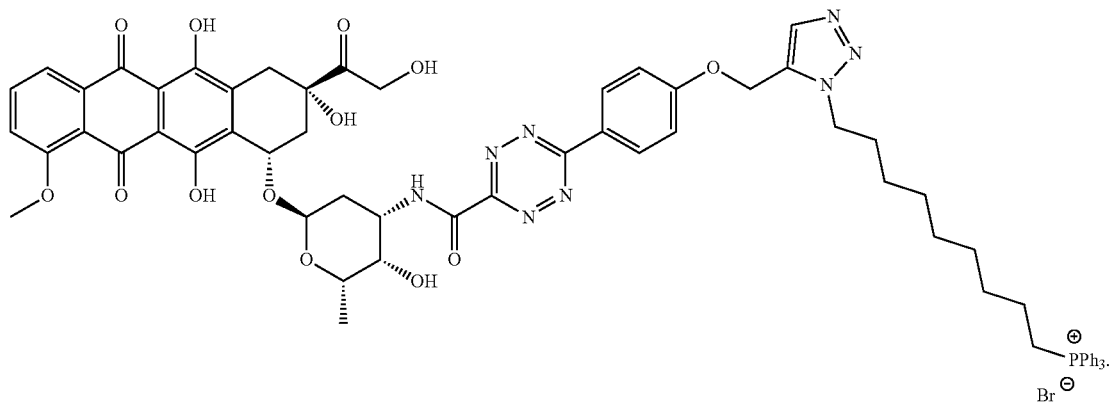

17. The chemical delivery system of any one of embodiments 13-16, wherein the unimolecular cyclization reaction results in the formation of a lactone, a thiolactone, or a lactam.

18. The chemical delivery system of embodiment 17, wherein the lactone, the thiolactone, or the lactam comprises a five-membered ring or a six-membered ring.

19. The chemical delivery system of any one of embodiments 13-18, wherein the cargo compound has a structure according to Formula II:

(II)

wherein $R^4$ is the second targeting moiety and $R^5$ is the cargo-releasing moiety.

20. The chemical delivery system of embodiment 19, wherein $R^5$ is selected from the group consisting of —OH, —SH, and —NH$_2$.

21. The chemical delivery system of embodiment 19 or embodiment 20, wherein the trigger compound has a structure according to Formula IIa:

(IIa)

22. The chemical delivery system of embodiment 21, wherein the trigger compound has a structure according to Formula IIb:

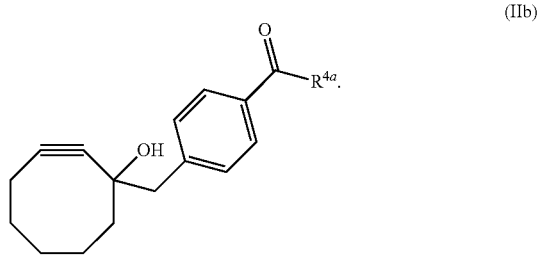

(IIb)

23. The chemical delivery system of embodiment 21 or embodiment 22, wherein the trigger compound is:

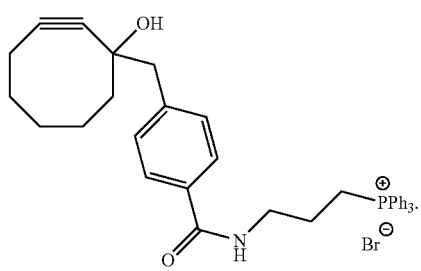

24. The chemical delivery system of any one of embodiments 1-23, wherein the cargo moiety is a drug moiety.

25. A pharmaceutical composition comprising the chemical delivery system of any one of embodiments 1-24 and a pharmaceutically acceptable excipient.

26. A method for treating a disease or condition, the method comprising administering to a subject in need thereof an effective amount of a chemical delivery system according to any one of embodiments 1-24 or an effective amount of a pharmaceutical composition according to embodiment 25.

27. The method of embodiment 26, wherein the disease or condition is selected from the group consisting of cancer, inflammation, and bacterial infection.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A chemical delivery system having:
  i) a cargo compound according to Formula I:

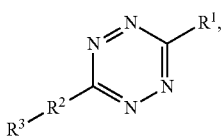

(I)

wherein:
$R^1$ is a first enrichment moiety,
$R^2$ is a cleavable linker, and
$R^3$ is a tethered cargo moiety
  ii) a trigger compound according to Formula II:

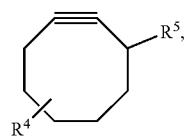

(II)

wherein:
R⁴ is a second enrichment moiety, and
R⁵ is a cargo-releasing moiety selected from the group consisting of —OH, —SH, and —NH₂;
wherein:
the first enrichment moiety and the second enrichment moiety are independently selected from the group consisting of a positively charged phosphine, a folic acid moiety, a biotin moiety, an RGD peptide, a glucose moiety, an antibody, an aptamer, a prostate specific membrane antigen moiety, and a boronic acid moiety;
the tethered cargo moiety is selected from the group consisting of an amine-containing or alcohol-containing antibiotic, an amine-containing or alcohol-containing anti-inflammatory agent, and an amine-containing or alcohol-containing antiproliferative drug;
an increase in concentration of the cargo compound and an increase in concentration of the trigger compound at a target site cause a bimolecular reaction between the cargo compound and the trigger compound to form a cyclization precursor compound; and
the cargo moiety is released from the cyclization precursor compound in a unimolecular cyclization reaction resulting in the formation of a lactone, a thiolactone, or a lactam.

2. The chemical delivery system of claim 1, wherein the rate of the bimolecular reaction after the increase in concentration of the cargo compound and the concentration of the trigger compound at the target site is at least 2-500 times the rate of the bimolecular reaction without the increase in concentration.

3. The chemical delivery system of claim 1, wherein the second order rate constant for the bimolecular reaction ranges from about $10^{-5}$ M⁻¹ s⁻¹ to about 120 M⁻¹s⁻¹.

4. The chemical delivery system of claim 1, wherein the first enrichment moiety and the second enrichment moiety are positively charged phosphines.

5. The chemical delivery system of claim 1, wherein the first enrichment moiety and the second enrichment moiety are selected from the group consisting of a folic acid moiety, a biotin moiety, an RGD peptide, a glucose moiety, an antibody, an aptamer, a prostate specific membrane antigen moiety, and a boronic acid moiety.

6. The chemical delivery system of claim 1, wherein the cargo compound is:

7. The chemical delivery system of claim 1, wherein the trigger compound has a structure according to Formula IIa:

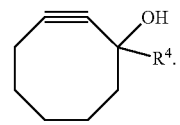

(IIa)

8. The chemical delivery system of claim 7, wherein the trigger compound has a structure according to Formula IIb:

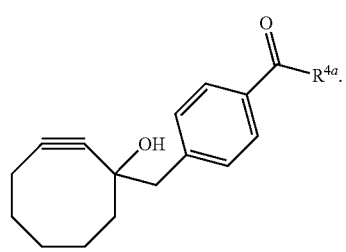

(IIb)

9. The chemical delivery system of claim 7, wherein the trigger compound is:

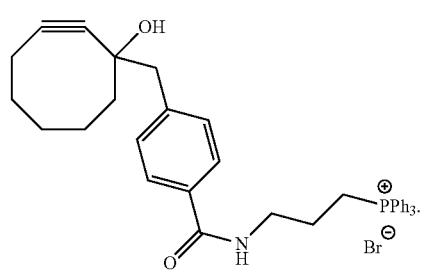

10. A pharmaceutical composition comprising the chemical delivery system of claim 1 and a pharmaceutically acceptable excipient.

11. A method for treating a disease or condition, the method comprising administering to a subject in need thereof an effective amount of a chemical delivery system

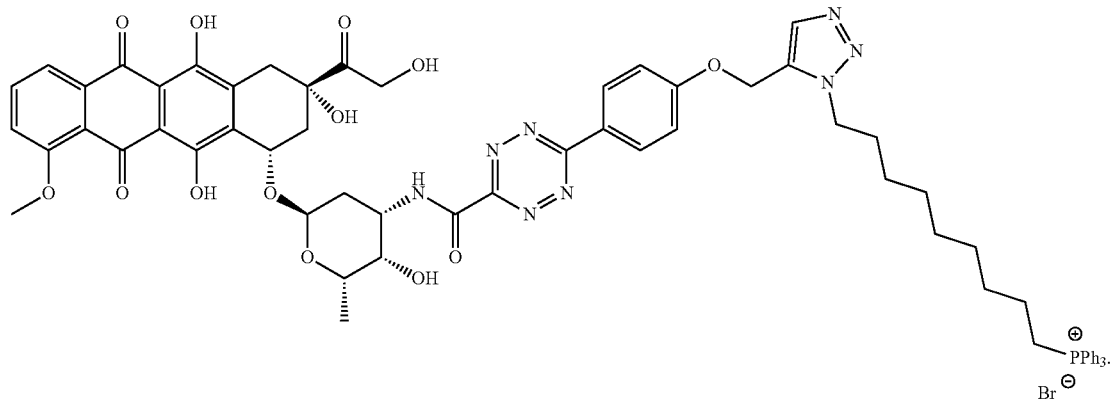

according to claim 1, wherein the disease or condition is selected from the group consisting of cancer, inflammation, and bacterial infection.

* * * * *

UNITED STATES PATENT AND TRADEMARK OFFICE
CERTIFICATE OF CORRECTION

| | |
|---|---|
| PATENT NO. | : 11,607,458 B2 |
| APPLICATION NO. | : 16/758833 |
| DATED | : March 21, 2023 |
| INVENTOR(S) | : Binghe Wang et al. |

It is certified that error appears in the above-identified patent and that said Letters Patent is hereby corrected as shown below:

In the Claims

In Column 70, Line 59, in Claim 1, delete "moiety" and insert -- moiety; and --.

In Column 71, Line 37, in Claim 3, delete "$10^{-5}$ $M^{-1}$ $s^{-1}$" and insert -- $10^{-5}$ $M^{-1}s^{-1}$ --.

Signed and Sealed this
Thirteenth Day of February, 2024

*Katherine Kelly Vidal*

Katherine Kelly Vidal
*Director of the United States Patent and Trademark Office*

SEQUENCE LISTING

<160> NUMBER OF SEQ ID NOS: 14

<210> SEQ ID NO 1
<211> LENGTH: 6
<212> TYPE: PRT
<213> ORGANISM: Simian vacuolating virus 40

<400> SEQUENCE: 1

Lys Lys Lys Arg Lys Val
1               5

<210> SEQ ID NO 2
<211> LENGTH: 17
<212> TYPE: PRT
<213> ORGANISM: Xenopus laevis

<400> SEQUENCE: 2

Lys Arg Pro Ala Ala Thr Lys Lys Ala Gly Gln Ala Lys Lys Lys Lys
1               5                   10                  15

Leu

<210> SEQ ID NO 3
<211> LENGTH: 7
<212> TYPE: PRT
<213> ORGANISM: Simian vacuolating virus 40

<400> SEQUENCE: 3

Pro Lys Lys Lys Arg Lys Val
1               5

<210> SEQ ID NO 4
<211> LENGTH: 6
<212> TYPE: PRT
<213> ORGANISM: Drosophila melanogaster

<400> SEQUENCE: 4

Arg Arg Lys Arg Gln Arg
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(13)
<223> OTHER INFORMATION: Any amino acid

<400> SEQUENCE: 5

Lys Arg Xaa Xaa Xaa Xaa Xaa Xaa Xaa Xaa Xaa Xaa Lys Lys Leu
1               5                   10                  15

Arg

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (6)..(17)
<223> OTHER INFORMATION: Any amino acid

<400> SEQUENCE: 6

Arg Lys Lys Arg Lys Xaa Xaa Xaa Xaa Xaa Xaa Xaa Xaa Xaa Xaa
1               5                   10                  15

Xaa Lys Lys Ser Lys
            20

<210> SEQ ID NO 7
<211> LENGTH: 13
<212> TYPE: PRT
<213> ORGANISM: Saccharomyces cerevisiae

<400> SEQUENCE: 7

Met Asn Lys Ile Pro Ile Lys Asp Leu Leu Asn Pro Gln
1               5                   10

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Leu Thr Gln Glu Thr Asn Lys Val Glu Thr Tyr Lys Glu Gln Pro
1               5                   10                  15

Leu Lys Thr Pro Gly Lys Lys Lys Gly Lys Pro
            20                  25

<210> SEQ ID NO 9
<211> LENGTH: 38
<212> TYPE: PRT
<213> ORGANISM: Homo sapiens

<400> SEQUENCE: 9

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
            35

<210> SEQ ID NO 10
<211> LENGTH: 27
<212> TYPE: PRT
<213> ORGANISM: Saccharomyces cerevisiae

<400> SEQUENCE: 10

Ser Ala Asn Lys Val Thr Lys Asn Lys Ser Asn Ser Ser Pro Tyr Leu
1               5                   10                  15

Asn Lys Arg Lys Gly Lys Pro Gly Pro Asp Ser
            20                  25

<210> SEQ ID NO 11
<211> LENGTH: 43
<212> TYPE: PRT
<213> ORGANISM: Homo sapiens
```

```
<400> SEQUENCE: 11

Val His Ser His Lys Lys Lys Ile Arg Thr Ser Pro Thr Phe Thr
1               5                   10                  15

Thr Pro Lys Thr Leu Arg Leu Arg Arg Gln Pro Lys Tyr Pro Arg Lys
                20                  25                  30

Ser Ala Pro Arg Arg Asn Lys Leu Asp His Tyr
            35                  40

<210> SEQ ID NO 12
<211> LENGTH: 42
<212> TYPE: PRT
<213> ORGANISM: Saccharomyces cerevisiae

<400> SEQUENCE: 12

Asn Ala Pro Ser Ala Lys Ala Thr Ala Ala Lys Lys Ala Val Val Lys
1               5                   10                  15

Gly Thr Asn Gly Lys Lys Ala Leu Lys Val Arg Thr Ser Ala Thr Phe
                20                  25                  30

Arg Leu Pro Lys Thr Leu Lys Leu Ala Arg
            35                  40

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any amino acid

<400> SEQUENCE: 13

Asp Glu Xaa Xaa Xaa Leu Ile
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 14

Asp Xaa Xaa Leu Leu
1               5
```